United States Patent
Rao et al.

(10) Patent No.: US 12,054,742 B2
(45) Date of Patent: Aug. 6, 2024

(54) COMPOSITIONS AND METHODS TO DERIVE MESODERMAL LINEAGE CELLS AND MIXED TISSUE ORGANOIDS FROM EMBRYONIC STEM CELLS

(71) Applicant: THE REGENTS OF THE UNIVERSITY OF MICHIGAN, Ann Arbor, MI (US)

(72) Inventors: Rajesh Rao, Ann Arbor, MI (US); Qiang Li, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 634 days.

(21) Appl. No.: 16/251,740

(22) Filed: Jan. 18, 2019

(65) Prior Publication Data
US 2019/0218510 A1 Jul. 18, 2019

Related U.S. Application Data

(60) Provisional application No. 62/618,937, filed on Jan. 18, 2018.

(51) Int. Cl.
| | | |
|---|---|---|
| C12N 5/0735 | (2010.01) | |
| C12N 5/00 | (2006.01) | |
| C12N 5/077 | (2010.01) | |
| C12N 5/079 | (2010.01) | |
| C12N 5/0793 | (2010.01) | |
| C12N 15/85 | (2006.01) | |
| C12Q 1/02 | (2006.01) | |

(52) U.S. Cl.
CPC ......... *C12N 5/0606* (2013.01); *C12N 5/0037* (2013.01); *C12N 5/062* (2013.01); *C12N 5/0621* (2013.01); *C12N 5/0657* (2013.01); *C12N 15/85* (2013.01); *C12Q 1/025* (2013.01); *C12N 2500/99* (2013.01); *C12N 2501/22* (2013.01); *C12N 2501/2303* (2013.01); *C12N 2501/385* (2013.01); *C12N 2501/998* (2013.01); *C12N 2506/02* (2013.01); *C12N 2510/00* (2013.01); *C12N 2513/00* (2013.01); *C12N 2533/90* (2013.01)

(58) Field of Classification Search
CPC ................ C12Q 1/6881; C12N 5/0657; C12N 2506/02; C12N 2510/00
See application file for complete search history.

(56) References Cited

FOREIGN PATENT DOCUMENTS

WO WO-2013/010965 A1 1/2013

OTHER PUBLICATIONS

Shalem 2014, Science, 343:84-87.*
Li, 2020, Cell Reports, 30:465-480.*
Ang et al., Wdr5 mediates self-renewal and reprogramming via the embryonic stem cell core transcriptional network. *Cell.* 145, 183-197 (2011).
Assawachananont et al., Transplantation of embryonic and induced pluripotent stem cell-derived 3D retinal sheets into retinal degenerative mice, *Stem Cells Reports.* 2:662-72 (2014).
Batzer et al., Enhanced evolutionary PCR using oligonucleotides with inosine at the 3'-terminus, *Nucleic Acids Res.* 19:5081 (1991).
Boheler et al., Differentiation of pluripotent embryonic stem cells into cardiomyocytes, *Circ. Res.* 91:189-201 (2002).
Bruce et al., Dynamic transcription programs during ES cell differentiation towards mesoderm in serum versus serum-freeBMP4 culture, *BMC Genomics.* 8:365 (2007).
Cao et al., Targeting MLL1 H3K4 methyltransferase activity in mixed-lineage leukemia, *Mol. Cell.* 53:247-61 (2014).
Carugo et al., In Vivo Functional Platform Targeting Patient-Derived Xenografts Identifies WDR5-Myc Association as a Critical Determinant of Pancreatic Cancer, *Cell Rep.* 16:133-147 (2016).
Chantada et al., Strategies to manage retinoblastoma in developing countries, Pediatr. *Blood Cancer.* 56:341-8 (2011).
Creighton, Proteins, W.H. Freeman and Company, New York (1984).
Database Uniprot P01106, Accession No. P01106, "Myc proto-oncogene protein" (1987).
Database Uniprot Q9H9L4, Accession No. Q9H9L4, "KAT8 regulatory NSL complex subunit 2" (2010).
Decembrini et al., Derivation of traceable and transplantable photoreceptors from mouse embryonic stem cells, *Stem Cells Reports.* 2:853-65 (2014).
Deng et al., HoxBlinc RNA Recruits Set1/MLL Complexes to Activate Hox Gene Expression Patterns and Mesoderm Lineage Development, *Cell. Rep.* 14:103-114 (2016).
Dias et al., Structural analysis of the KANSL1/WDR5/KANSL2 complex reveals that WDR5 is required for efficient assembly and chromatin targeting of the NSL complex. *Genes Dev.* 28:929-42 (2014).

(Continued)

*Primary Examiner* — Valarie E Bertoglio
(74) *Attorney, Agent, or Firm* — MARSHALL, GERSTEIN & BORUN LLP

(57) ABSTRACT

The disclosure relates to methods for producing mesodermal lineage cells, cardiac lineage cells, hematopoietic lineage cells, retinal lineage cells, and combinations thereof. In some aspects, the disclosure relates to methods of producing mixed tissue organoids comprising retinal lineage cells and cardiac lineage cells. When interaction of WDR5 protein at the binding pocket/interaction surface with RBBP5/MYC/KANSL2 is disrupted in the embryonic stem cell for a set period of time after differentiation of the embryonic stem cell has begun, and the disruption of that interaction is subsequently removed, differentiation of the embryonic stem cell to a mesodermal lineage cell is obtained. Such mesodermal lineage cells may, in some methods of the disclosure, be subsequently differentiated into cardiac lineage cells and hematopoietic lineage cells. The disclosure also relates to method for producing mixed lineage organoids, comprising retinal and mesodermal, including cardiac, lineage cells in a single organoid. The disclosure also relates to cells and organoids obtained by the methods, uses of the cells and organoids, and kits comprising the cells and/or reagents for producing them.

5 Claims, 36 Drawing Sheets

Specification includes a Sequence Listing.

(56) References Cited

OTHER PUBLICATIONS

Dingar et al., BioID identifies novel c-MYC interacting partners in cultured cells and xenograft tumors, *J. Proteomics.* 118:95-111 (2015).
Dou et al., Physical association and coordinate function of the H3 K4 methyltransferase MLL1 and the H4 K16 acetyltransferase MOF, *Cell.* 121:873-85 (2005).
Dou et al., Regulation of MLL1 H3K4 methyltransferase activity by its core components, *Nat. Struct. Mol. Biol.* 13:713-9 (2006).
Ee et al., An Embryonic Stem Cell-Specific NuRD Complex Functions through Interaction with WDR5, *Stem Cell Reports.* 8:1488-96 (2017).
Eiraku et al., Self-organizing optic-cup morphogenesis in three-dimensional culture, *Nature.* 472:51-6 (2011).
Gage et al., Expression of the homeobox gene Pitx2 in neural crest is required for optic stalk and ocular anterior segment development, *Hum. Mol. Genet.* 14:3347-59 (2005).
Gonzalez-Rodriguez et al., Mutational screening of CHX10, GDF6, OTX2, Rax and SOX2 genes in 50 unrelated microphthalmia-anophthalmia-coloboma (MAC) spectrum cases, *Br. J. Ophthalmol.* 94:1100-4 (2010).
Gori et al., Wdr5, a WD-40 protein, regulates osteoblast differentiation during embryonic bone development, *Dev. Biol.* 295:498-506 (2006).
Hadjal et al., A p38MAPK-p53 cascade regulates mesodermal differentiation and neurogenesis of embryonic stem cells, *Cell Death Dis.* 4:e737 (2013).
Heinz et al., Simple combinations of lineage-determining transcription factors prime cis-regulatory elements required for macrophage and B cell identities, *Mol. Cell.* 38:576-89 (2010).
Heng et al., The nuclear receptor Nr5a2 can replace Oct4 in the reprogramming of murine somatic cells to pluripotent cells, *Cell Stem Cell.* 6:167-74 (2010).
Honda et al., N-cadherin is a useful marker for the progenitor of cardiomyocytes differentiated from mouse ES cells in serum-free condition, *Biochem. Biophys. Res. Commun.* 351:877-882 (2006).
Hubert et al., Epigenetic regulation of planarian stem cells by the SET1/MLL family of histone methyltransferases, *Epigenetics.* 8:79-91 (2013).
International Search Report and Written Opinion, PCT/US19/14192 (Apr. 11, 2019).
Jiang et al., Role for Dpy-30 in ES cell-fate specification by regulation of H3K4 methylation within bivalent domains, *Cell.* 144:513-25 (2011).
Kamiya et al., Intrinsic transition of embryonic stem-cell differentiation into neural progenitors, *Nature.* 470:503-9 (2011).
Karatas et al., High-affinity, small-molecule peptidomimetic inhibitors of MLL1/WDR5 protein- protein interaction, *J. Am. Chem. Soc.* 135: 669-82 (2013).
Khan M, et al., Characterization and pharmacologic targeting of EZH2, a fetal retinal protein and epigenetic regulator, in human retinoblastoma, *Laboratory Investigation.* 95:1278-90 (2015).
Kim et al., TopHat2: accurate alignment of transcriptomes in the presence of insertions, deletions and gene fusions, *Genome Biol.* 14:R36 (2013).
Koch et al., Antagonistic Activities of Sox2 and Brachyury Control the Fate Choice of Neuro-Mesodermal Progenitors, *Dev. Cell.* 42:514-26 (2017).
Kokkinopoulos et al., Cardiomyocyte differentiation from mouse embryonic stem cells using a simple and defined protocol, *Dev. Dyn.* 245:157-65 (2016).
Kouskoff et al., Sequential development of hematopoietic and cardiac mesoderm during embryonic stem cell differentiation, *Proc. Natl. Acad. Sci. USA.* 102:13170-5 (2005).
Kovacs et al., Absence of Rybp Compromises Neural Differentiation of Embryonic Stem Cells, *Stem Cells Int.* 2016:4034620 (2016).

Labelle-Dumais et al., Nuclear receptor NR5A2 is required for proper primitive streak morphogenesis, *Dev. Dyn.* 235:3359-69 (2006).
Lancaster et al., Organogenesis in a dish: modeling development and disease using organoid technologies, *Science.* 345:1247125 (2014).
Langmead et al., Fast gapped-read alignment with Bowtie 2, *Nat. Methods.* 9:357-9 (2012).
Li et al., Tet proteins influence the balance between neuroectodermal and mesodermal fate choice by inhibiting Wnt signaling, *Proc. Natl. Acad. Sci. USA.* E8267-76 (2016).
Li et al., The histone acetyltransferase MOF is a key regulator of the embryonic stem cell core transcriptional network, *Cell Stem Cell.* 11:163-78 (2012).
Li et al., The Sequence Alignment/Map format and SAMtools, *Bioinformatics.* 25:2078-9 (2009).
Maltsev et al., Embryonic stem cells differentiate in vitro into cardiomyocytes representing sinusnodal, atrial and ventricular cell types, *Mech. Dev.* 44:41-50 (1993).
Mandai et al., Autologous Induced Stem-Cell-Derived Retinal Cells for Macular Degeneration, *N. Engl. J. Med.* 377:1038-46 (2017).
Merkle et al., Human pluripotent stem cells recurrently acquire and expand dominant negative P53 mutations, *Nature.* 545:229-33 (2017).
Nakano et al., Self-formation of optic cups and storable stratified neural retina from human ESCs, *Cell Stem Cell.* 10:771-85 (2012).
Odho et al., Characterization of a novel WDR5-binding site that recruits RbBP5 through a conserved motif to enhance methylation of histone H3 lysine 4 by mixed lineage leukemia protein-1, *J. Biol. Chem.* 285:32967-76 (2010).
Ohtsuka et al., An alternative approach to deoxyoligonucleotides as hybridization probes by insertion of deoxyinosine at ambiguous codon positions, *J. Biol. Chem.* 260:2605-8 (1985).
Osakada et al., Stepwise differentiation of pluripotent stem cells into retinal cells, *Nat. Protoc.* 4:811-24 (2009).
Patel et al., Structure of WDR5 bound to mixed lineage leukemia protein-1 peptide, *J. Biol. Chem.* 283:32158-61 (2008).
Perera et al., TET3 is recruited by REST for context-specific hydroxymethylation and induction of gene expression, *Cell Rep.* 11:283-94 (2015).
Pirity et al., Rybp, a polycomb complex-associated protein, is required for mouse eye development, *BMC Dev. Biol.* 7:39 (2007).
Quadrato et al., Cell diversity and network dynamics in photosensitive human brain organoids, *Nature.* 545:48-53 (2017).
Quinlan et al., BEDTools: a flexible suite of utilities for comparing genomic features, *Bioinformatics.* 26:841-2 (2010).
Ramirez et al., deepTools2: a next generation web server for deep-sequencing data analysis, *Nucleic Acids Res.* 44:W160-5 (2016).
Ramirez et al., deepTools: a flexible platform for exploring deep-sequencing data, *Nucleic Acids Res.* W187-91 (2014).
Rao et al., Hijacked in cancer: the KMT2 (MLL) family of methyltransferases, *Nat. Rev. Cancer.* 15:334-46 (2015).
Rao et al., Stem Cells for Retinal Disease: A Perspective on the Promise and Perils, *Am. J. Ophthalmol.* 179:32-38 (2017).
Rojas et al., Gata4 expression in lateral mesoderm is downstream of BMP4 and is activated directly by Forkhead and GATA transcription factors through a distal enhancer element, *Development.* 132:3405-17 (2005).
Rose et al., RYBP stimulates PRC1 to shape chromatin-based communication between Polycomb repressive complexes, *Elife.* 5:e18591 (2016).
Rossolini et al., Use of deoxyinosine-containing primers vs degenerate primers for polymerase chain reaction based on ambiguous sequence information, *Mol. Cell Probes.* 8:91-8 (1994).
Sachinidis et al., Generation of cardiomyocytes from embryonic stem cells experimental studies, *Herz.* 27:589-97 (2002).
Schulz et al., Charge and Kabuki syndromes: a phenotypic and molecular link, *Hum. Mol. Genet.* 23:4396-4405 (2014).
Schwartz et al., Embryonic stem cell trials for macular degeneration: a preliminary report, *Lancet.* 379:713-20 (2012).
Schwartz et al., Human embryonic stem cell-derived retinal pigment epithelium in patients with age-related macular degeneration and Stargardt's macular dystrophy: follow-up of two open-label phase 1/2 studies, *Lancet.* 385:509-16 (2015).

(56) References Cited

OTHER PUBLICATIONS

Thomas et al., Interaction with WDR5 promotes target gene recognition and tumorigenesis by MYC, *Mol. Cell.* 58:440-52 (2015).
Thomas et al., The MYC-WDR5 Nexus and Cancer, *Cancer Res.* 75:4012-5 (2015).
Thorvaldsdóttir et al., Integrative Genomics Viewer (IGV): high-performance genomics data visualization and exploration, *Brief Bioinform.* 14:178-92 (2013).
Wang et al., CCCTC-Binding Factor Transcriptionally Targets Wdr5 to Mediate Somatic Cell Reprogramming, *Stem Cells Dev.* 26:743-50 (2017).
Watanabe et al., Directed differentiation of telencephalic precursors from embryonic stem cells, *Nat. Neurosci.* 8:288-96 (2005).
Wysocka et al., WDR5 associates with histone H3 methylated at K4 and is essential for H3 K4 methylation and vertebrate development, *Cell.* 121:859-72 (2005).
Xie et al., WDR5 positively regulates p53 stability by inhibiting p53 ubiquitination, *Biochem. Biophys. Res. Comm.* 487:333-8 (2017).
Yang et al., Essential role of lncRNA binding for WDR5 maintenance of active chromatin and embryonic stem cell pluripotency, *Elife.* 12:e02046 (2014).
Zaidi et al., De novo mutations in histone-modifying genes in congenital heart disease, *Nature.* 498:220-3 (2013).
Zhang et al., Model-based analysis of ChIP-Seq (MACS), *Genome Biol.* 9:R137 (2008).
Gu et al., Histone H3 lysine 4 methyltransferases and demethylases in self-renewal and differentiation of stem cells, *Cell. Biosci.* 3:39 (2013).
Meilhac et al., Cardiac cell lineages that form the heart, *Cold Spring Harbor Perspectives in Medicine.* 4:a013888 (2014).
Velten et al., Human haematopoietic stem cell lineage commitment is a continuous process, *Nature Cell Biology.* 19:271-281 (2017).

* cited by examiner

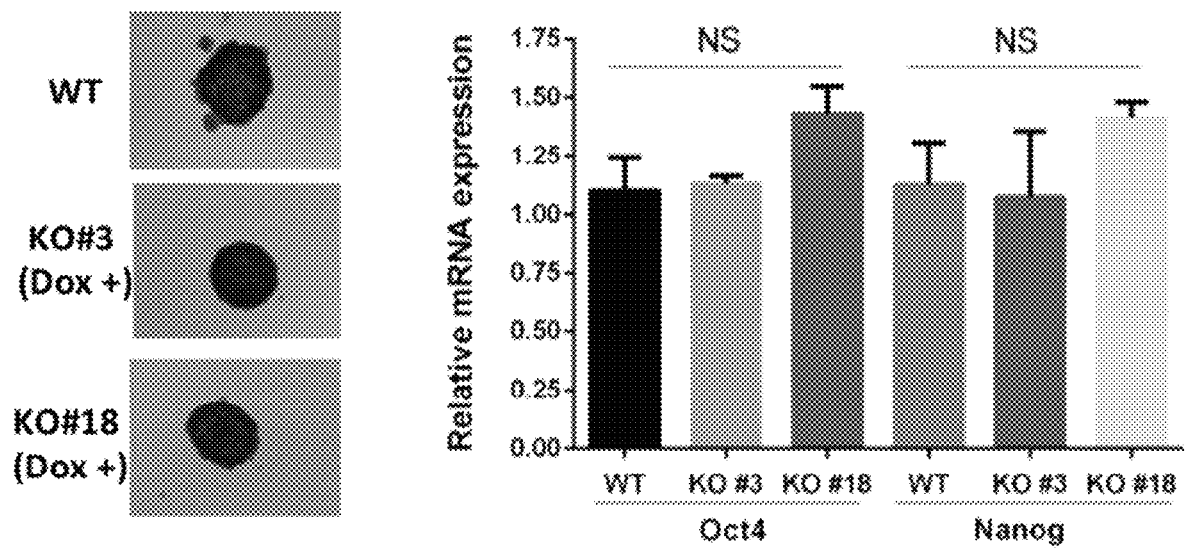
FIGURE 1C
FIGURE 1D
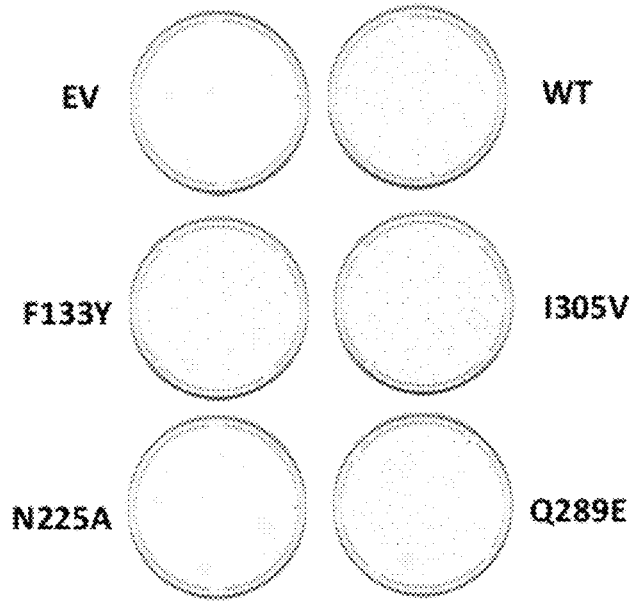
KO#7 rescued with
FIGURE 1E

SEQUENCE LISTING

<160> NUMBER OF SEQ ID NOS: 48

<210> SEQ ID NO 1
<211> LENGTH: 334
<212> TYPE: PRT
<213> ORGANISM: Homo sapiens
<220> FEATURE:
<221> NAME/KEY: MISC_FEATURE
<223> OTHER INFORMATION: WT WDR5

<400> SEQUENCE: 1

```
Met Ala Thr Glu Glu Lys Lys Pro Glu Thr Glu Ala Ala Arg Ala Gln
1               5                   10                  15

Pro Thr Pro Ser Ser Ser Ala Thr Gln Ser Lys Pro Thr Pro Val Lys
            20                  25                  30

Pro Asn Tyr Ala Leu Lys Phe Thr Leu Ala Gly His Thr Lys Ala Val
            35                  40                  45

Ser Ser Val Lys Phe Ser Pro Asn Gly Glu Trp Leu Ala Ser Ser Ser
    50                  55                  60

Ala Asp Lys Leu Ile Lys Ile Trp Gly Ala Tyr Asp Gly Lys Phe Glu
65                  70                  75                  80

Lys Thr Ile Ser Gly His Lys Leu Gly Ile Ser Asp Val Ala Trp Ser
                85                  90                  95

Ser Asp Ser Asn Leu Leu Val Ser Ala Ser Asp Lys Thr Leu Lys
            100                 105                 110

Ile Trp Asp Val Ser Ser Gly Lys Cys Leu Lys Thr Leu Lys Gly His
    115                 120                 125

Ser Asn Tyr Val Phe Cys Cys Asn Phe Asn Pro Gln Ser Asn Leu Ile
130                 135                 140

Val Ser Gly Ser Phe Asp Glu Ser Val Arg Ile Trp Asp Val Lys Thr
145                 150                 155                 160

Gly Lys Cys Leu Lys Thr Leu Pro Ala His Ser Asp Pro Val Ser Ala
                165                 170                 175

Val His Phe Asn Arg Asp Gly Ser Leu Ile Val Ser Ser Ser Tyr Asp
            180                 185                 190

Gly Leu Cys Arg Ile Trp Asp Thr Ala Ser Gly Gln Cys Leu Lys Thr
    195                 200                 205

Leu Ile Asp Asp Asp Asn Pro Pro Val Ser Phe Val Lys Phe Ser Pro
210                 215                 220

Asn Gly Lys Tyr Ile Leu Ala Ala Thr Leu Asp Asn Thr Leu Lys Leu
225                 230                 235                 240

Trp Asp Tyr Ser Lys Gly Lys Cys Leu Lys Thr Tyr Thr Gly His Lys
                245                 250                 255

Asn Glu Lys Tyr Cys Ile Phe Ala Asn Phe Ser Val Thr Gly Gly Lys
            260                 265                 270

Trp Ile Val Ser Gly Ser Glu Asp Asn Leu Val Tyr Ile Trp Asn Leu
    275                 280                 285

Gln Thr Lys Glu Ile Val Gln Lys Leu Gln Gly His Thr Asp Val Val
290                 295                 300

Ile Ser Thr Ala Cys His Pro Thr Glu Asn Ile Ile Ala Ser Ala Ala
305                 310                 315                 320

Leu Glu Asn Asp Lys Thr Ile Lys Leu Trp Lys Ser Asp Cys
                325                 330
```

<210> SEQ ID NO 2
<211> LENGTH: 6

```
<212> TYPE: PRT
<213> ORGANISM: Artificial Sequence
<220> FEATURE:
<223> OTHER INFORMATION: Synthetic Polypeptide

<400> SEQUENCE: 2

Asp Asp Leu Asp Val Val
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 3

Leu Asp Val Val
1

<210> SEQ ID NO 4
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 4

Glu Glu Val Asp Val Thr
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 5

Glu Val Asp Val Thr
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 6

Val Asp Val Thr
1

<210> SEQ ID NO 7
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 7

Glu Glu Ile Asp Val Val
1               5

<210> SEQ ID NO 8
<211> LENGTH: 4
<212> TYPE: PRT
```

<213> ORGANISM: Artificial Sequence
<220> FEATURE:
<223> OTHER INFORMATION: Synthetic Polypeptide

<400> SEQUENCE: 8

Ile Asp Val Val
1

<210> SEQ ID NO 9
<211> LENGTH: 1005
<212> TYPE: DNA
<213> ORGANISM: Homo Sapiens
<220> FEATURE:
<221> NAME/KEY: misc_feature
<223> OTHER INFORMATION: WT WDR5

<400> SEQUENCE: 9

| atggcgacgg aggagaagaa gcccgagacc gaggccgcca gagcacagcc aaccccttcg | 60 |
| tcatccgcca ctcagagcaa gcctacacct gtgaagccaa actatgctct aaagttcacc | 120 |
| cttgctggcc acaccaaagc agtgtcctcc gtgaaattca gcccgaatgg agagtggctg | 180 |
| gcaagttcat ctgctgataa acttattaaa atttggggcg cgtatgatgg gaaatttgag | 240 |
| aaaaccatat ctggtcacaa gctgggaata tccgatgtag cctggtcgtc agattctaac | 300 |
| cttcttgttt ctgcctcaga tgacaaaacc ttgaagatat gggacgtgag ctcgggcaag | 360 |
| tgtctgaaaa ccctgaaggg acacagtaat tatgtctttt gctgcaactt caatccccag | 420 |
| tccaacctta ttgtctcagg atcctttgac gaaagcgtga ggatatggga tgtgaaaaca | 480 |
| gggaagtgcc tcaagacttt gccagctcac tcggatccag tctcggccgt tcattttaat | 540 |
| cgtgatggat ccttgatagt ttcaagtagc tatgatggtc tctgtcgcat ctgggacacc | 600 |
| gcctcaggcc agtgcctgaa gacgctcatc gatgacgaca ccccccccgt gtcttttgtg | 660 |
| aagttctccc cgaacggcaa atacatcctg gccgccacgc tggacaacac tctgaagctc | 720 |
| tgggactaca gcaaggggaa gtgcctgaag acgtacactg ccacaagaa tgagaaatac | 780 |
| tgcatatttg ccaatttctc tgttactggt gggaagtgga ttgtgtctgg ctcagaggat | 840 |
| aaccttgttt acatctggaa ccttcagacg aaagagattg tacagaaact acaaggccac | 900 |
| acagatgtcg tgatctcaac agcttgtcac ccaacagaaa acatcatcgc tctgctgcg | 960 |
| ctagaaaatg acaaaacaat taaactgtgg aagagtgact gctaa | 1005 |

<210> SEQ ID NO 10
<211> LENGTH: 1005
<212> TYPE: DNA
<213> ORGANISM: Homo Sapiens
<220> FEATURE:
<221> NAME/KEY: misc_feature
<223> OTHER INFORMATION: WDR5 MUTANT F133Y

<400> SEQUENCE: 10

| atggcgacgg aggagaagaa gcccgagacc gaggccgcca gagcacagcc aaccccttcg | 60 |
| tcatccgcca ctcagagcaa gcctacacct gtgaagccaa actatgctct aaagttcacc | 120 |
| cttgctggcc acaccaaagc agtgtcctcc gtgaaattca gcccgaatgg agagtggctg | 180 |
| gcaagttcat ctgctgataa acttattaaa atttggggcg cgtatgatgg gaaatttgag | 240 |
| aaaaccatat ctggtcacaa gctgggaata tccgatgtag cctggtcgtc agattctaac | 300 |
| cttcttgttt ctgcctcaga tgacaaaacc ttgaagatat gggacgtgag ctcgggcaag | 360 |
| tgtctgaaaa ccctgaaggg acacagtaat tatgtctttt gctgcaactt caatccccag | 420 |

```
tccaacctta ttgtctcagg atcctttgac gaaagcgtga ggatatggga tgtgaaaaca       480
gggaagtgcc tcaagacttt gccagctcac tcggatccag tctcggccgt tcattttaat       540
cgtgatggat ccttgatagt ttcaagtagc tatgatggtc tctgtcgcat ctgggacacc       600
gcctcaggcc agtgcctgaa gacgctcatc gatgacgaca accccccgt gtcttttgtg        660 aagttctccc cgaacggcaa atacatcctg gccgccacgc tggacaacac tctgaagctc       720
tgggactaca gcaaggggaa gtgcctgaag acgtacactg gccacaagaa tgagaaatac       780
tgcatatttg ccaatttctc tgttactggt gggaagtgga ttgtgtctgg ctcagaggat       840
aaccttgttt acatctggaa ccttgagacg aaagagattg tacagaaact acaaggccac       900
acagatgtcg tgatctcaac agcttgtcac ccaacagaaa acatcatcgc ctctgctgcg       960
ctagaaaatg acaaaacaat taaactgtgg aagagtgact gctaa                      1005

<210> SEQ ID NO 11
<211> LENGTH: 1005
<212> TYPE: DNA
<213> ORGANISM: Homo Sapiens
<220> FEATURE:
<221> NAME/KEY: misc_feature
<223> OTHER INFORMATION: WDR5 MUTANT N225A

<400> SEQUENCE: 11
atggcgacgg aggagaagaa gcccgagacc gaggccgcca gcacagcc aaccccttcg          60 tcatccgcca ctcagagcaa gcctacacct gtgaagccaa actatgctct aaagttcacc       120
cttgctggcc acaccaaagc agtgtcctcc gtgaaattca gcccgaatgg agagtggctg       180
gcaagttcat ctgctgataa acttattaaa atttggggcg cgtatgatgg gaaatttgag       240
aaaaccatat ctggtcacaa gctgggaata tccgatgtag cctggtcgtc agattctaac       300
cttcttgttt ctgcctcaga tgacaaaacc ttgaagatat gggacgtgag ctcgggcaag       360
tgtctgaaaa ccctgaaggg acacagtaat tatgtctttt gctgcaactt caatccccag       420
tccaacctta ttgtctcagg atcctttgac gaaagcgtga ggatatggga tgtgaaaaca       480
gggaagtgcc tcaagacttt gccagctcac tcggatccag tctcggccgt tcattttaat       540
cgtgatggat ccttgatagt ttcaagtagc tatgatggtc tctgtcgcat ctgggacacc       600
gcctcaggcc agtgcctgaa gacgctcatc gatgacgaca accccccgt gtcttttgtg        660 aagttctccc ctgcaggcaa atacatcctg gccgccacgc tggacaacac tctgaagctc       720
tgggactaca gcaaggggaa gtgcctgaag acgtacactg gccacaagaa tgagaaatac       780
tgcatatttg ccaatttctc tgttactggt gggaagtgga ttgtgtctgg ctcagaggat       840
aaccttgttt acatctggaa ccttcagacg aaagagattg tacagaaact acaaggccac       900
acagatgtcg tgatctcaac agcttgtcac ccaacagaaa acatcatcgc ctctgctgcg       960
ctagaaaatg acaaaacaat taaactgtgg aagagtgact gctaa                      1005

<210> SEQ ID NO 12
<211> LENGTH: 1005
<212> TYPE: DNA
<213> ORGANISM: Homo Sapiens
<220> FEATURE:
<221> NAME/KEY: misc_feature
<223> OTHER INFORMATION: WDR5 MUTANT L240K

<400> SEQUENCE: 12
atggcgacgg aggagaagaa gcccgagacc gaggccgcca gcacagcc aaccccttcg          60 tcatccgcca ctcagagcaa gcctacacct gtgaagccaa actatgctct aaagttcacc       120
```

```
cttgctggcc acaccaaagc agtgtcctcc gtgaaattca gcccgaatgg agagtggctg      180
gcaagttcat ctgctgataa acttattaaa atttggggcg cgtatgatgg gaaatttgag      240
aaaaccatat ctggtcacaa gctgggaata tccgatgtag cctggtcgtc agattctaac      300
cttcttgttt ctgcctcaga tgacaaaacc ttgaagatat gggacgtgag ctcgggcaag      360
tgtctgaaaa ccctgaaggg acacagtaat tatgtctttt gctgcaactt caatccccag      420
tccaacctta ttgtctcagg atcctttgac gaaagcgtga ggatatggga tgtgaaaaca      480
gggaagtgcc tcaagacttt gccagctcac tcggatccag tctcggccgt tcatttaat       540 cgtgatggat ccttgatagt ttcaagtagc tatgatggtc tctgtcgcat ctgggacacc      600
gcctcaggcc agtgcctgaa gacgctcatc gatgacgaca accccccgt gtcttttgtg       660 aagttctccc cgaacggcaa atacatcctg gccgccacgc tggacaacac tctgaagaaa      720
tgggactaca gcaaggggaa gtgcctgaag acgtacactg ccacaagaa tgagaaatac       780 tgcatatttg ccaatttctc tgttactggt gggaagtgga ttgtgtctgg ctcagaggat      840
aaccttgttt acatctggaa ccttcagacg aaagagattg tacagaaact acaaggccac      900
acagatgtcg tgatctcaac agcttgtcac ccaacagaaa acatcatcgc ctctgctgcg      960
ctagaaaatg acaaaacaat taaactgtgg aagagtgact gctaa                    1005

<210> SEQ ID NO 13
<211> LENGTH: 1005
<212> TYPE: DNA
<213> ORGANISM: Homo Sapiens
<220> FEATURE:
<221> NAME/KEY: misc_feature
<223> OTHER INFORMATION: WDR5 MUTANT V268E

<400> SEQUENCE: 13
atggcgacgg aggagaagaa gcccgagacc gaggccgcca gagcacagcc aacccttcg       60 tcatccgcca ctcagagcaa gcctacacct gtgaagccaa actatgctct aaagttcacc      120
cttgctggcc acaccaaagc agtgtcctcc gtgaaattca gcccgaatgg agagtggctg      180
gcaagttcat ctgctgataa acttattaaa atttggggcg cgtatgatgg gaaatttgag      240
aaaaccatat ctggtcacaa gctgggaata tccgatgtag cctggtcgtc agattctaac      300
cttcttgttt ctgcctcaga tgacaaaacc ttgaagatat gggacgtgag ctcgggcaag      360
tgtctgaaaa ccctgaaggg acacagtaat tatgtctttt gctgcaactt caatccccag      420
tccaacctta ttgtctcagg atcctttgac gaaagcgtga ggatatggga tgtgaaaaca      480
gggaagtgcc tcaagacttt gccagctcac tcggatccag tctcggccgt tcatttaat       540 cgtgatggat ccttgatagt ttcaagtagc tatgatggtc tctgtcgcat ctgggacacc      600
gcctcaggcc agtgcctgaa gacgctcatc gatgacgaca accccccgt gtcttttgtg       660 aagttctccc cgaacggcaa atacatcctg gccgccacgc tggacaacac tctgaagctc      720
tgggactaca gcaaggggaa gtgcctgaag acgtacactg ccacaagaa tgagaaatac       780 tgcatatttg ccaatttctc tgaaccggt gggaagtgga ttgtgtctgg ctcagaggat       840
aaccttgttt acatctggaa ccttcagacg aaagagattg tacagaaact acaaggccac      900
acagatgtcg tgatctcaac agcttgtcac ccaacagaaa acatcatcgc ctctgctgcg      960
ctagaaaatg acaaaacaat taaactgtgg aagagtgact gctaa                    1005

<210> SEQ ID NO 14
<211> LENGTH: 1005
```

```
<212> TYPE: DNA
<213> ORGANISM: Homo Sapiens
<220> FEATURE:
<221> NAME/KEY: misc_feature
<223> OTHER INFORMATION: WDR5 MUTANT Q289E

<400> SEQUENCE: 14
atggcgacgg aggagaagaa gcccgagacc gaggccgcca gagcacagcc aaccccttcg      60
tcatccgcca ctcagagcaa gcctacacct gtgaagccaa actatgctct aaagttcacc     120
cttgctggcc acaccaaagc agtgtcctcc gtgaaattca gcccgaatgg agagtggctg     180
gcaagttcat ctgctgataa acttattaaa atttggggcg cgtatgatgg gaaatttgag     240
aaaaccatat ctggtcacaa gctgggaata tccgatgtag cctggtcgtc agattctaac     300
cttcttgttt ctgcctcaga tgacaaaacc ttgaagatat gggacgtgag ctcgggcaag     360
tgtctgaaaa ccctgaaggg acacagtaat tatgtctttt gctgcaactt caatccccag     420
tccaacctta ttgtctcagg atcctttgac gaaagcgtga ggatatggga tgtgaaaaca     480
gggaagtgcc tcaagacttt gccagctcac tcggatccag tctcggccgt tcattttaat     540
cgtgatggat ccttgatagt ttcaagtagc tatgatggtc tctgtcgcat ctgggacacc     600
gcctcaggcc agtgcctgaa gacgctcatc gatgacgaca accccccgt gtcttttgtg      660 aagttctccc cgaacggcaa atacatcctg gccgccacgc tggacaacac tctgaagctc     720
tgggactaca gcaaggggaa gtgcctgaag acgtacactg ccacaagaa tgagaaatac      780 tgcatatttg ccaatttctc tgttactggt gggaagtgga ttgtgtctgg ctcagaggat     840
aaccttgttt acatctggaa ccttcagacg aaagagattg tacagaaact acaaggccac     900
acagatgtcg tggtctcaac agcttgtcac ccaacagaaa acatcatcgc tctgctgcg      960 ctagaaaatg acaaaacaat taaactgtgg aagagtgact gctaa                    1005

<210> SEQ ID NO 15
<211> LENGTH: 1005
<212> TYPE: DNA
<213> ORGANISM: Homo Sapiens
<220> FEATURE:
<221> NAME/KEY: misc_feature
<223> OTHER INFORMATION: WDR5 MUTANT I305V

<400> SEQUENCE: 15
atggcgacgg aggagaagaa gcccgagacc gaggccgcca gagcacagcc aaccccttcg      60
tcatccgcca ctcagagcaa gcctacacct gtgaagccaa actatgctct aaagttcacc     120
cttgctggcc acaccaaagc agtgtcctcc gtgaaattca gcccgaatgg agagtggctg     180
gcaagttcat ctgctgataa acttattaaa atttggggcg cgtatgatgg gaaatttgag     240
aaaaccatat ctggtcacaa gctgggaata tccgatgtag cctggtcgtc agattctaac     300
cttcttgttt ctgcctcaga tgacaaaacc ttgaagatat gggacgtgag ctcgggcaag     360
tgtctgaaaa ccctgaaggg acacagtaat tatgtctttt gctgcaactt caatccccag     420
tccaacctta ttgtctcagg atcctttgac gaaagcgtga ggatatggga tgtgaaaaca     480
gggaagtgcc tcaagacttt gccagctcac tcggatccag tctcggccgt tcattttaat     540
cgtgatggat ccttgatagt ttcaagtagc tatgatggtc tctgtcgcat ctgggacacc     600
gcctcaggcc agtgcctgaa gacgctcatc gatgacgaca accccccgt gtcttttgtg      660 aagttctccc cgaacggcaa atacatcctg gccgccacgc tggacaacac tctgaagctc     720
tgggactaca gcaaggggaa gtgcctgaag acgtacactg ccacaagaa tgagaaatac      780
```

```
tgcatatttg ccaatttctc tgttactggt gggaagtgga ttgtgtctgg ctcagaggat    840
aaccttgttt acatctggaa ccttcagacg aaagagattg tacagaaact acaaggccac    900
acagatgtcg tggtctcaac agcttgtcac ccaacagaaa acatcatcgc ctctgctgcg    960
ctagaaaatg acaaaacaat taaactgtgg aagagtgact gctaa                   1005
```

<210> SEQ ID NO 16
<211> LENGTH: 20
<212> TYPE: DNA
<213> ORGANISM: Homo Sapiens
<220> FEATURE:
<221> NAME/KEY: misc_feature
<223> OTHER INFORMATION: MWDR5 GUIDE RNA SEQUENCE

<400> SEQUENCE: 16

```
tgtgaagttc agccccaatg                                                 20
```

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: A-MHC

<400> SEQUENCE: 17

```
gcccagtacc tccgaaagtc                                                 20
```

<210> SEQ ID NO 18
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: A-MHC

<400> SEQUENCE: 18

```
gccttaacat actcctcctt gtc                                             23
```

<210> SEQ ID NO 19
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: B-MHC

<400> SEQUENCE: 19

```
acaacccta cgattatgcg t                                                21
```

<210> SEQ ID NO 20
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: B-MHC

<400> SEQUENCE: 20
acgtcaaagg cactatccgt g                                              21

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: TROPONIN T

<400> SEQUENCE: 21
ggcagaaccg cctggctgaa                                                20

<210> SEQ ID NO 22
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: TROPONIN T

<400> SEQUENCE: 22
ctgccacagc tccttggcct                                                20

<210> SEQ ID NO 23
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MEF2C

<400> SEQUENCE: 23
ctgagcgtgc tgtgcgactg t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MEF2C

<400> SEQUENCE: 24
gctctcgtgc ggctcgttgt a                                              21

<210> SEQ ID NO 25
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MYOCD

<400> SEQUENCE: 25
cgccactgaa aggtccaact                                                20

<210> SEQ ID NO 26

```
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MYOCD

<400> SEQUENCE: 26
gtggaggctt ggagaatgtg                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: RAX

<400> SEQUENCE: 27
cgacgttcac cacttaccaa                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: RAX

<400> SEQUENCE: 28
tcggttctgg aaccatacct                                              20

<210> SEQ ID NO 29
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: SIX3

<400> SEQUENCE: 29
ccggaagagt tgtccatgtt c                                            21

<210> SEQ ID NO 30
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: SIX3

<400> SEQUENCE: 30
cgactcgtgt ttgttgatgg c                                            21

<210> SEQ ID NO 31
<211> LENGTH: 20
<212> TYPE: DNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<223> OTHER INFORMATION: NCAD

<400> SEQUENCE: 31
cagggtggac gtcattgtag                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: NCAD

<400> SEQUENCE: 32
agggtctcca ccactgattc                                              20

<210> SEQ ID NO 33
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: OCT4

<400> SEQUENCE: 33
gtggaggaag ccgacaacaa tga                                          23

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: OCT4

<400> SEQUENCE: 34
caaaagaccc tgagacgatg                                              20

<210> SEQ ID NO 35
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: ACTIN

<400> SEQUENCE: 35
accaactggg acgacatgga gaag                                         24

<210> SEQ ID NO 36
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: ACTIN
```

<400> SEQUENCE: 36
caagctgatt ggcgatgtga g                                      21

<210> SEQ ID NO 37
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: FOXA2

<400> SEQUENCE: 37
ggcccagtca cgaacaaagc                                        20

<210> SEQ ID NO 38
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: FOXA2

<400> SEQUENCE: 38
ttctcatcag ccagaacacc t                                      21

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GATA4

<400> SEQUENCE: 39
ttcctgctcg gacttgggac                                        20

<210> SEQ ID NO 40
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GATA4

<400> SEQUENCE: 40
gcagccaatc atagcagact tgcgt                                  25

<210> SEQ ID NO 41
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GATA6

<400> SEQUENCE: 41
acagcccact tctgtgttcc c                                      21

<210> SEQ ID NO 42
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: GATA6

<400> SEQUENCE: 42
cttctgtttc cgatcagctc ccttg                                25

<210> SEQ ID NO 43
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: NANOG

<400> SEQUENCE: 43
tggtccccac agtttgccta gttc                                 24

<210> SEQ ID NO 44
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: NANOG

<400> SEQUENCE: 44
ggtcgtttga accaagtccc tc                                   22

<210> SEQ ID NO 45
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: SOX2

<400> SEQUENCE: 45
caggagaacc ccaagatgca caa                                  23

<210> SEQ ID NO 46
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: SOX2

<400> SEQUENCE: 46
attaagctcc tgggtcgcaa g                                    21

<210> SEQ ID NO 47
<211> LENGTH: 23

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: T

<400> SEQUENCE: 47
ctctaatgtc ctcccttgtt gcc                                              23

<210> SEQ ID NO 48
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: T

<400> SEQUENCE: 48
ttcccaggca ggtggagaat aag                                              23
```

COMPOSITIONS AND METHODS TO DERIVE MESODERMAL LINEAGE CELLS AND MIXED TISSUE ORGANOIDS FROM EMBRYONIC STEM CELLS

STATEMENT OF GOVERNMENT INTEREST

This invention was made with government support under EY022299 and EY026654, awarded by the National Institutes of Health. The government has certain rights in the invention.

This application contains, as a separate part of the disclosure, a Sequence Listing in computer-readable form (filename: 52352A_Seqlistin.txt, created Jan. 17, 2019; 22,586 bytes—ASCII text file), which is incorporated herein by reference in its entirety.

FIELD

The disclosed subject matter generally relates to the field of stem cell biology and, more specifically, to the differentiation of embryonic stem cells. The disclosure relates to methods for producing mesodermal lineage cells, cardiac lineage cells, hematopoietic lineage cells, retinal lineage cells, and combinations thereof from embryonic stem cells. In some aspects, the disclosure relates to methods of producing mixed tissue organoids comprising retinal lineage cells and cardiac lineage cells. These methods include modulating the interaction of WDR5 protein within WDR5 at a binding site (i.e., the binding pocket or interaction surface within WDR5), wherein WDR5 binds RBBP5/MYC/KANSL2. When WDR5 expression is disrupted at this binding pocket in the embryonic stem cell for a set period of time and the disruption of that interaction is subsequently removed, the differentiation of the embryonic stem cell to a mesodermal lineage cell is obtained. In various aspects, such mesodermal lineage cells are subsequently differentiated into cardiac lineage cells and hematopoietic lineage cells. When mutations occur within WDR5 at this binding pocket, organoids comprising cells of mixed lineage are obtained. The disclosure also relates to cells and organoids obtained by these methods, kits comprising the cells and/or reagents for producing them, and uses of these cells and organoids.

BACKGROUND

The derivation of mesodermal lineage cells from stem cells, such as cardiomyocytes and hematopoietic cells, has clinical and research importance relating to research studies of development, as well as translational (e.g., diagnostic and therapeutic) applications for heart disease and hematological disorders. Typically, the production of these cells requires serum-containing media (e.g., fetal bovine serum and the like) that is both expensive and its composition remains poorly characterized. Likewise, the replacement of serum with growth factors also is expensive and not cost-effective. These aspects create unmet needs that stem from high variability of culture and increased costs using current technologies to generate stem-cell derived mesodermal lineage cells.

The ability to generate a wide spectrum of differentiated cell types from embryonic stem cells in culture offers a powerful approach for studying lineage induction and specification and a promising source of progenitors for cell replacement therapy.

SUMMARY

The disclosure provides methods for serum-free and growth-factor free culture to derive mesodermal lineage cells capable of differentiation to cardiac lineage cells and hematopoietic lineage cells from embryonic stem cells. The disclosure provides methods of serum-free and growth factor-free culture to derive mixed tissue organoids in which one region of the organoid is ectodermal tissue (e.g. brain or retinal tissue) and another portion of the same organoid is mesodermal tissue (e.g. beating cardiac-lineage cells). Mixed tissue organoids, in various aspects, are models for 3-dimensional embryonic development of multiple germ layers within one organoid. The disclosure also provides a 3D-organoid based assay suitable for downstream drug or genetic screening in high throughput culture conditions (e.g., 96 well plates). In various aspects, therefore, the disclosure provides mesodermal lineage cells, cardiac lineage cells, hematopoietic lineage cells, and organoids comprising retinal lineage and cardiac lineage cells for high-throughput and/or content screening, drug discovery, toxicity assessment, and nicheology.

The disclosure provides methods for reducing the cost of culture, without need for serum, or exogenous cytokines, such as bone morphogenic protein 4 (BMP4), activin A, and vascular endothelial growth factor (VEGF), for generation of mesodermal lineage progenitors, such as cardiac cells and hematopoietic cells. The disclosure provides methods for suppressing neuroectodermal differentiation in the presence of neuroectoderm-promoting (serum-free) culture conditions to reduce contamination of non-mesodermal cell types when the intent is to generate mesodermal lineage cells from embryonic stem cells. The disclosure provides improved elucidation of critical genes, proteins, chemicals and other factors related to mesodermal lineage cells due to lack of necessity for poorly defined culture reagents, such as serum. The disclosure provides mixed tissue organoids by introducing a point mutation in a recombinant WDR5 gene transfected into embryonic stem cells. Such mixed tissue organoids may produce a blood supply from the mesoderm region of the organoid toward an ectodermal portion of the same organoid, enabling enhanced maturation of the target tissue (e.g. retinal portion of organoid maturing more fully due to presence of adjacent mesoderm/hematopoietic/blood supply from another region of the mixed organoid).

The disclosure provides methods for modulating WD repeat-containing protein 5 (WDR5) and the WDR5 gene to change or manipulate cell differentiation and cell fate. In one embodiment, WDR5 is modulated in an embryonic stem cell (ESC) to convert the ESC into a mesodermal linage cell. In some aspects, WDR5 is modulated at the binding site to inhibit WDR5 binding with MYC (including c-MYC), retinoblastoma-binding protein 5 (RBBP5) and/or KAT8 regulatory NSL (KANSL) (including KANSL2).

The disclosure provides methods for producing a mesodermal stem cell from an embryonic stem cell comprising turning off WDR5 expression in the embryonic stem cell after embryonic stem cell conditions are removed at EB day 0; turning on WDR5 expression in the now embryonic body cell at a period of time greater than 24 hours and less than 60 hours after WDR5 expression was first turned off, thereby allowing the mesodermal stem cell to be produced. In some aspects, the period of time is about 36 hours to about 48 hours after WDR5 expression was turned off.

In some aspects, the disclosure includes methods for producing a mesodermal lineage cell from an embryonic stem cell comprising a recombinant WDR5 gene under control of an inducible reporter or agent, the method comprising delaying induction of expression of the recombinant WDR5 gene by the embryonic stem cell for a set period of time; and inducing expression of the recombinant WDR5 protein by the embryonic stem cell for subsequent differentiation of the embryonic stem cell into the mesodermal lineage cell by administering an inducing agent to the culture medium, and/or turning off the transient suppression of expression of recombinant WDR5 by the embryonic stem cell.

In some aspects, the disclosure includes methods for producing a mesodermal lineage cell from an embryonic stem cell comprising a recombinant WDR5 gene under control of an inducible reporter or agent, the method comprising delaying interaction of recombinant WDR5 protein with RBBP5 protein, MYC protein, and/or KANSL2 protein in the embryonic stem cell by suppressing expression of WDR5 protein for a set period of time; and inducing expression of the recombinant WDR5 protein by the embryonic stem cell for subsequent differentiation of the embryonic stem cell into the mesodermal lineage cell by administering an inducing agent to the culture medium, or turning off the transient suppression of expression of recombinant WDR5 by the embryonic stem cell, thereby allowing the mesodermal lineage cell to differentiate from the embryonic stem cell.

The disclosure provides methods for producing in culture a mesodermal lineage cell from an embryonic stem cell comprising recombinant WDR5 protein, the method comprising disrupting interaction of recombinant WDR5 protein with RBBP5, MYC, or KANSL2 protein in the embryonic stem cell for a set period of time, wherein the set period of time is greater than 24 hours and less than 60 hours, and removing the disruption of the interaction of recombinant WDR5 protein with RBBP5, MYC, or KANSL2 in the embryonic stem cell to allow the mesodermal lineage cell to differentiate from the embryonic stem cell.

In some aspects, the disrupting step is carried out by silencing recombinant WDR5 protein expression by the embryonic stem cell. In some aspects, silencing recombinant WDR5 protein expression comprises introducing a polynucleotide encoding a recombinant WDR5 protein under control of a transactivator protein into the embryonic stem cell; and limiting the expression of the recombinant WDR5 protein in the embryonic stem cell by controlling the transactivator protein.

In some aspects, the removing step comprises turning on the expression of the transactivator protein allowing expression of the recombinant WDR5 protein in the embryonic stem cell. In some aspects, the method further comprises silencing endogenous WDR5 protein expression in the embryonic stem cell.

In various aspects, the recombinant WDR5 protein is human. In various aspects, the embryonic stem cell is mammalian. In particular aspects, the embryonic stem cell is mouse or human.

In some aspects, the culture comprises a medium, wherein the medium is a serum-free and/or growth factor-free. In some aspects, the growth factor-free medium is free of BMP4, activin A, VEGF, or a combination of any thereof. In some aspects, the method is carried out in retinal culture conditions, as described herein. Such aspects are particularly valuable in lowering the costs involved in culturing embryonic stem cells.

In some aspects, the set period of time starts when the embryonic stem cell is allowed to begin differentiation. In some aspects, the set period of time is about 36 to about 48 hours.

In some aspects, the disrupting step takes place at a WDR5-RBBP5 interaction surface or binding pocket, a WDR5-MYC interaction surface or binding pocket, and/or a WDR5-KANSL2 interaction surface or binding pocket. In some aspects, the interaction surface comprises a polypeptide comprising the amino acid sequence set forth in any of SEQ ID NOs: 2-8. In more particular aspects, the interaction surface comprises the polypeptide comprising the amino acid sequence set forth in SEQ ID NO: 3, 6, or 8.

In some aspects, the mesodermal lineage cell is within an embryoid body. In some aspects, the mesodermal lineage cell is in a monolayer culture. The disclosure includes a mesodermal lineage cell produced according to the methods described herein.

The disclosure provides methods for producing in culture a cardiac lineage cell from a mesodermal lineage cell. In some aspects, the method comprises maintaining the mesodermal lineage cell in culture for at least about six days allowing the cardiac lineage cell to be produced, or allowing the cardiac lineage cell to differentiate. In some aspects, the mesodermal lineage or cardiac lineage cell is maintained in culture for about 16 days. In some aspects, the cardiac lineage cell may be maintained in culture from about 6 days to about 16 days. In some aspects, the culture is carried out in serum-free medium, growth factor-free medium, or serum-free and growth factor-free medium. In some aspects, the culture is carried out in retinal lineage culture conditions, as described herein. The disclosure includes a cardiac lineage cell produced according to the methods described herein.

The disclosure provides methods for producing in culture a hematopoietic lineage cell from a cardiac lineage cell, wherein the method comprises resuspending the cardiac lineage cell in hematopoietic culture conditions allowing the hematopoietic lineage cell to be produced or to differentiate. Such hematopoietic culture conditions are known in the art and also are described herein. The disclosure includes a hematopoietic lineage cell produced according to the methods described herein.

The disclosure provides methods for producing a mixed lineage organoid comprising retinal lineage cells and cardiac lineage cells from an embryonic stem cell in culture, the method comprising introducing into the embryonic stem cell a polynucleotide encoding a mutant recombinant WDR5 protein comprising a mutation which interferes with binding of WDR5 protein to RBBP5, MYC, or KANSL2; also introducing into the embryonic stem cell a polynucleotide encoding a wild type recombinant WDR5 protein; disrupting interaction of the wild type recombinant WDR5 protein with RBBP5, MYC, or KANSL2 protein in the embryonic stem cell for a set period of time greater than 24 hours and less than 60 hours, and removing the disruption of the interaction of the wild type recombinant WDR5 protein with RBBP5, MYC, or KANSL2 in the embryonic stem cell to allow retinal lineage cells and cardiac lineage cells to differentiate from the embryonic stem cell. In some aspects, the mutant recombinant WDR5 protein is constitutively expressed once it is introduced into the embryonic stem cell. In some aspects, this constitutive expression of mutant WDR5 begins prior to differentiation, i.e., prior to EB day 0. In some aspects, the disrupting step is carried out by silencing wild type recombinant WDR5 protein expression by the embryonic stem cell. In some aspects, silencing wild type recombinant WDR5 protein expression comprises inhibiting wild type recombinant WDR5 protein by use of a transactivator protein. In some aspects, this silencing step starts at differentiation, i.e., at EB day 0. In some aspects, the removing step comprises turning on or allowing expression of the wild type recombinant WDR5 protein in the embryonic stem cell.

In some aspects, the wild type recombinant WDR5 protein is human. In some aspects, the mutant recombinant WDR5 protein comprises an amino acid substitution at position 225, 240, or 268 of the amino acid sequence set forth in SEQ ID NO: 1. In some aspects, the mutant recombinant WDR5 protein is hWDR5$^{N225A}$, hWDR5$^{L240K}$, or hWDR5$^{V268E}$.

In some aspects, the methods of the disclosure further include silencing endogenous WDR5 protein expression in the embryonic stem cell. In some aspects, the embryonic stem cell is mammalian. In some aspects, the embryonic stem cell is mouse or human.

In various aspects, the culture comprises a medium, wherein the medium is a serum-free and/or growth factor-free. In some aspects, the growth factor-free medium is free of BMP4, activin A, VEGF, or a combination of any thereof. In some aspects, the methods of the disclosure are carried out in retinal culture conditions. Such culture conditions are valuable, especially when culturing cells without the need for serum and growth factors can provide great cost savings.

In various aspects, the set period of time starts when the embryonic stem cell is allowed to begin differentiation. In some aspects, the set period of time is greater than 24 hours and less than 60 hours. In some aspects, the set period of time is about 36 to about 48 hours.

In various aspects, the disrupting step takes place at a WDR5-RBBP5 interaction surface or binding pocket, a WDR5-MYC interaction surface or binding pocket, and/or a WDR5-KANSL2 interaction surface or binding pocket. In some aspects, the interaction surface or binding pocket comprises a polypeptide comprising the amino acid sequence set forth in any of SEQ ID NOs: 2-8. In some aspects, the interaction surface comprises the polypeptide comprising the amino acid sequence set forth in SEQ ID NO: 3, 6, or 8.

In some aspects, the mesodermal lineage cells and cardiac lineage cells are within an organoid. In some aspects, a combination of mesodermal lineage cells and cardiac lineage cells are produced within a single organoid. The disclosure includes a mixed lineage organoid(s) produced according to the methods described herein. The disclosure also includes a kit or kits comprising reagents for producing any of the methods described herein and, optionally, instructions for use. In some aspects, the kits comprise the cell(s) produced according to any of the methods described herein and, optionally, a diluent, container, or instructions for use. In some aspects, the disclosure includes kits and compositions comprising the cells described herein and an acceptable carrier or diluent.

The disclosure provides uses of the cell(s) made according to the methods described herein. In some aspects, these uses include, but are not limited to, cell replacement therapy, high-throughput and/or content screening, drug discovery, or toxicity screening. In a particular aspect, the disclosure includes the use of cardiac lineage cells to screen a compound or compounds for cardiotoxicity.

Other features and advantages of the disclosure will become apparent from the following detailed description. It should be understood, however, that the detailed description and the specific examples, while indicating embodiments of the disclosed subject matter, are given by way of illustration only, because various changes and modifications within the spirit and scope of the disclosure will become apparent to those skilled in the art from this detailed description.

BRIEF DESCRIPTION OF THE DRAWING

FIGS. 1A-1E. Acute loss of WDR5 leads to impaired ESC self-renewal. (FIG. 1A) mWdr5 mRNA expression in undifferentiated ESCs, GFP (+) retinal progenitor cells (or retinal lineage cells) and GFP (−) neuroectoderm cells. An Rx:GFP reporter ESC line, in which GFP is knocked-in under Rx/Rax gene promoter, was differentiated to Rax-GFP (+) retinal progenitor cells. At day 5, GFP(+) and GFP(−) populations were sorted by FACS. (FIG. 1B) Knockout of endogenous mWdr5 following CRISPR/Cas9 gene editing was determined by RT-qPCR (left) and western blotting (right). Three independently-edited hwDR5$^{Dox}$;mwdr5$^{KO}$ (i.e., mWdr5 KO) ESC lines (KO #3, #13, #18) were cultured with doxycycline (Dox). Left panel: RT-qPCR amplified only mouse WDR5 (endo WDR5), but not human WDR5 mRNA. Right panel: Western blotting was used to distinguish endogenous (lower arrow) and exogenous (upper arrow, exogenous hWDR5 fused to HA tag) WDR5 protein. EV: Cas9 plasmid px459 V2 (empty vector) transfected ESCs. β-actin was used for loading control. (FIGS. 1C and 1D) Wild-type (WT) and two independently-edited m WDR5 KO clonal ESC lines were maintained in the presence of Dox and remained in undifferentiated state as determined by positive alkaline phosphatase staining (FIG. 1C) and comparable expression of pluripotent genes (Oct4 and Nanog) (FIG. 1D). (FIG. 1E) Self-renewal capability of mWDR5 KO ESCs reconstituted with WT or mutant hWDR5. Mouse Wdr5 KO ESCs were stably transfected with empty vector (EV), WT, MLL win motif binding mutants (F133Y and I305V) or RBBP5 binding mutants (N225 and Q289E) in the presence of Dox. To assay self-renewal, ESCs, which harbor an Oct4-dependent blasticidin resistance gene, were plated at clonal density in the absence of Dox, and resulting colonies were counted after 5 day treatment with blasticidin (right panel).

(FIG. 2A) Tight control of exogenous HA-hWDR5 during early time window of ESC differentiation. hWDR5$^{Dox}$;mWdr5$^{KO}$ (i.e., mWdr5 KO) ESCs were maintained in Dox (+) ESC media and Dox was removed upon ESC differentiation (day 0 or EB day 0 (EB0)). At different time points (0 h, 24 h, 36 h, 48 h, 60 h), cells were collected and subjected to probe HA-hWDR5 expression (a-HA). Tubulin: loading control. (FIG. 2B) Dose-dependent induction of exogenous hWDR5 and H3K4me during ESC differentiation. mWdr5 KO ESCs were maintained in Dox (+) ESC media and Dox was removed upon ESC differentiation (day 0). At 12 h post differentiation, different doses of Dox were added to mWdr5 KO EBs. At embryoid body (EB) day 4 (EB4), EBs were collected and extracted histones were subjected to western blotting. Total H3 was used as loading control. (FIGS. 2C and 2D) WDR5 regulates retinal progenitor cell proliferation and differentiation in a dose-dependent manner. WT and mWdr5 KO ESCs were maintained in the Dox-containing media. Upon differentiation (EB day 0), EBs were cultured in Dox-free conditions or with increasing concentrations (ng/ml) of Dox. Cell proliferation was determined at EB day 4 (FIG. 2C) and Rx-GFP positive retinal progenitor cells were scored by flow cytometry at day 5 (FIG. 2D). (FIG. 2E and FIG. 2F) WDR5 regulates retinal progenitor cell differentiation at a critical time window. mWdr5 KO ESCs were maintained in Dox (+) ESC media and Dox was removed upon ESC differentiation (day 0). At different time points, Dox was added to EBs at final concentration of 2.0 µg/ml. Cell proliferation was recorded at EB day 4 (FIG. 2E) and Rx-GFP positive retinal progenitor cells at EB day 5 were scored by flow cytometry (FIG. 2F). (FIG. 2G) Representative images of mWdr5 KO EBs (EB day 5) cultured in retinal differentiation conditions with or without Dox. (FIG. 2H) Wdr5 regulates RPC differentiation in a time-dependent manner as determined by Rx/Rax mRNA RT-qPCR.

(FIGS. 3A and 3B) Volcano plot of differentially expressed genes in WT versus hWDR5$^{Dox}$; mWdr5$^{KO}$ (i.e., mWdr5 KO) EBs with early induction of exogenous hWDR5 (T12h) (FIG. 3A), WT versus late induction of exogenous hWDR5 (T48h) (FIG. 3B) or T12h versus T48h (FIG. 3C). In FIGS. 3A-3C, ≥2-fold higher or lower differentially expressed genes are colored red and blue, respectively (FIG. 3D) Venn diagram of WT versus T12h, WT versus T48h and T12h versus T48h differentially expressed (≥2-fold) genes to compare overlapping and distinct genes among respective groups. (FIG. 3E) Gene ontology and heatmap clustering analysis of differential expressed (≥2-fold) genes in mWdr5 KO EBs with early (T12h) versus late (T48h) induction of exogenous hWDR5.

(FIGS. 4A, 4B, 4C and 4D) RT-qPCR analysis of pluripotent marker (Oct4, FIG. 4A), neuroepithelial marker (N-Cadherin, FIG. 4B), retinal ectoderm marker (Rax/Rx, FIG. 4C) and cardiomyocyte mesoderm marker (cTnT, FIG. 4D) during time-course differentiation of WT, early induction (T12h), late induction (T36h or T48h) of exogenous hWDR5 in hWDR5$^{Dox}$;mWdr5$^{KO}$ (i.e., mWdr5 KO) EBs. (FIGS. 4E, 4F and 4G) Immunohistochemistry staining on day 9 EB sections with neuroepithelial marker (N-Cadherin, FIG. 4E), cardiac specific troponin T (CT3, FIG. 4F) and sarcomere myosin (MF20, FIG. 4G) in WT and mWdr5 KO EB with early (T12h) or late (T36h or T48h) induction of exogenous hWDR5. DAPI was counterstained for nuclei. (FIG. 4H) Critical time points for exogenous hWDR5 linked to cardiomyocyte differentiation were determined by cTnT RT-qPCR. (FIG. 4I) Dose-dependent effect of exogenous hWDR5 during late induction period (T48h) on cardiomyocyte differentiation (cTnT and αMHC) and retinal neuroectoderm inhibition (Pax6 and Rax). (FIG. 4J) Heatmap for Rax and cTnT expression in day 8 mWdr5 KO EBs differentiating with or without the retinoic acid receptor antagonist AGN193109 (AGN), which stimulates retinal differentiation. (FIG. 4K) Switch toward cardiomyocyte differentiation by late induction of exogenous hWDR5 is not dependent to retinal neuroectoderm differentiation culture conditions. WT and mWdr5 KO EBs with early or late induction of exogenous hWDR5 were differentiated using serum-free culture of embryoid-body-like aggregate (SFEB) methods. Induction of early mesoderm marker (T/Brachyury) and cTnT was determined by RT-qPCR.

(FIG. 5A) Genomic distribution of HA-hWDR5 enriched peaks from EB day 6 hWDR5$^{Dox}$;mWdr5$^{KO}$ (i.e., mWdr5 KO) organoids with early (T12h, left panel) and late (T48h, right panel) induction of exogenous hWDR5. (FIGS. 5B and 5C) Heatmaps of clustered HA-hWDR5 ChIP-Seq signals demonstrating overlapping and distinct peaks in T12h and T48h settings. (FIG. 5D) De novo and associated known motif analysis in T12h and T48h conditions. (FIG. 5E) Venn diagram demonstrating overlaps between genes associated with HA-hWDR5 peaks and differentially expressed genes in T12h versus T48h samples. Examples of direct target genes are shown.

(FIGS. 6A and 6B) Proliferation and retinal lineage cell differentiation in hWDR5$^{Dox}$;mWdr5$^{KO}$ (i.e., mWdr5 KO) EBs stably transfected with WT or different hWDR5 mutants. Upon differentiation, Dox was removed (no Dox) or added back at 12 h later (T12h). Cell proliferation was determined at EB day 4 and relative cell proliferation was normalized to respective group with Dox as 1.0 (FIG. 6A). Percentage of Rx-GFP (+) cells at EB day 5 was determined by flow cytometry (FIG. 6B). (FIG. 6C) WT, but not WDR5-RBBP5 interaction mutant Q289E, retained capacity to induce Rx-GFP (+) RPC in mWdr5 KO EBs. Representative day 6 EBs were recorded under microscope using bright field or fluorescence channel. (FIGS. 6D and 6E) Effects of Rbbp5 interaction mutant Q289E WDR5 on RPC and cardiomyocyte differentiation were determined by RT-qPCR analysis of Rax/Rx (FIG. 6D) and cTnT (FIG. 6E).

(FIG. 7A) WT Rx:GFP ESCs were transfected with Dox-inducible HA-hWDR5 Piggybac plasmid and selected with G418 (200 ug/ml) for 5 days to generate stably transfected ESCs. ESCs were induced toward retinal progenitor cell (RPC) fate and different doses of Dox were added to cell suspensions upon differentiation (embryoid body (EB) day 0). At EB day 3, whole cell lysates were harvested for western blotting and determination of HA-hWDR5 induction. Undifferentiated WT Rx:GFP ESCs were used for control. (FIG. 7B) Overexpression of HA-hWDR5 during retinal differentiation did not affect retinal progenitor cell formation. Different doses of Dox were added to cell suspensions at EB day 0 and retinal progenitor cell differentiation was scored by percentage of Rx-GFP (+) cells in day 5 organoids using flow cytometry. (FIG. 7C) Guide RNA design for knockout mouse endogenous Wdr5 using CRISPR/Cas9 gene editing and Sanger sequencing of independent homozygous knockout (mWdr5 KO) clones. (FIG. 7D) Defective self-renewal in mWdr5 KO ESCs was rescued by exogenous hWDR5. Independent mWdr5 KO clones were maintained in Dox containing media. For re-plating, different doses of Dox were added to ES media containing blasticidin (20 ug/ml) to select for Oct4(+) pluripotent stem cells. (FIGS. 7E and 7F) Reconstitution of mWdr5 KO ESCs with different forms of non-Dox inducible, constitutively-expressed Flag-tagged hWDR5: WT, hWDR5 with MLL Win-motif binding mutants (F133Y, I305V) or hWDR5 with RBBP5 binding mutants (N225, L240K, V268E, Q289E). EV: empty vector backbone control. Stably transfected cells were maintained in Dox-containing ESC media and expression of non-inducible Flag-hWDR5 was determined by western blotting. (FIG. 7G) Self-renewal capacity of reconstituted hWDR5 with RBBP5 binding mutants. Stably transfected mWdr5 KO ESCs were maintained in Dox-containing media. ESCs were plated in clonal density (500 cells in 10 cm dish) with (+) or without Dox (−) to ES media and treated with blasticidin to select for Oct4 (+) pluripotent stem cells for 5 days. The resultant colony numbers were counted.

(FIG. 9A) Sample clustering of RNA-Seq data on WT or mWdr5 KO EBs with early (T12h) or late (T48h) induction of exogenous hWDR5. (FIG. 9B) Principal component analysis of RNA-Seq data on mWdr5 KO organoids with early (T12h) or late (T48h) induction of exogenous hWDR5. (FIG. 9C) Heatmap of all differentially expressed genes in mWdr5 KO EBs with early (T12h) or late (T48h) induction of exogenous hWDR5.

(FIGS. 10A, 10B, 10C and 10D) mWdr5 KO ESCs (KO #18) underwent induction of exogenous hWDR5 at early time point (12 h after differentiation, T12h) or late time point (36 h after differentiation, T36h) under retinal differentiation conditions. Expression of pluripotent marker (Oct4, FIG. 10A), neuroepithelial marker (N-cadherin, FIG. 10B), retinal ectoderm marker (Rax, FIG. 10C) and cardiomyocyte mesoderm marker (cTnT, FIG. 10D) during differentiation was determined by RT-qPCR. (FIGS. 10M-10Q) Validation of RNA-Seq data by RT-qPCR analysis of markers for retinal ectoderm (Sox2, FIG. 10M), endoderm (Gata4, FIG. 10N and Foxa2, FIG. 10O) and trophectoderm (Cdx2, P and Gata3, FIG. 10Q) in 2 independent mWdr5 KO clones.

(FIG. 11A) RT-qPCR analysis of Rax and cTnT expression in independently edited hWDR5$^{Dox}$;mWdr5$^{KO}$ (i.e., mWdr5 KO) clones stably transfected with WT or mutant Q289E hWDR5 (embryoid body (EB) day 6). (FIGS. 11B and 11C) RT-qPCR analysis of representative markers for retinal neuroectoderm (Rax, FIG. 11B) and cardiac mesoderm (cTnT, FIG. 11C) on day 6 EBs stably transfected with 3 hWDR5-Rbbp5 binding cultured with or without Dox-inducible WT hWDR5 (Dox added at T12h).

DETAILED DESCRIPTION

Figure 1A:
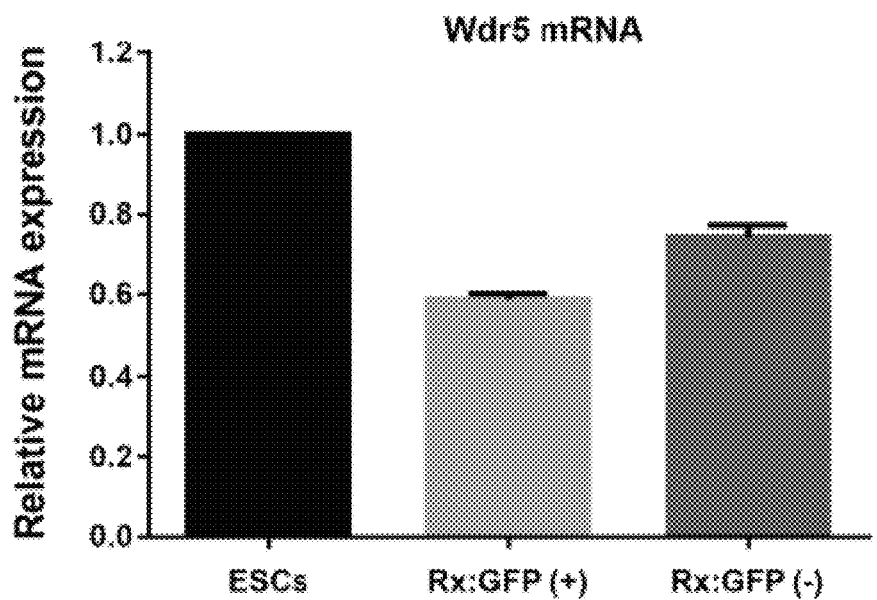

A more complete understanding of the methods and cells disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

As used herein, the following terms have the meanings ascribed to them unless specified otherwise.

The term "gene" refers to a DNA sequence that encodes a sequence of amino acids which comprise all or part of one or more polypeptides, proteins or enzymes, and may or may not include introns, and regulatory DNA sequences, such as promoter or enhancer sequences, 5'-untranslated region, or 3'-untranslated region which affect, for example, the conditions under which the gene is expressed. In the present disclosure, the WDR5 gene is manipulated to modulate differentiation of embryonic stem cells. The term "coding sequence" refers to a DNA sequence that encodes a sequence of amino acids, but does not contain introns or regulatory sequences.

"Nucleic acid" or "nucleic acid sequence" or "nucleic acid molecule" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The terms encompass molecules formed from any of the known base analogs of DNA and RNA such as, but not limited to 4-acetylcytosine, 8-hydroxy-N6-methyladenine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions, in some aspects, are achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

The terms "polypeptide," "peptide," and "protein" are used interchangeably herein to refer to a polymer of amino acid residues linked via peptide bonds. The terms apply to amino acid polymers in which one or more amino acid residue is an artificial chemical mimetic of a corresponding naturally occurring amino acid, as well as to naturally occurring amino acid polymers and non-naturally occurring amino acid polymers. The term "protein" typically refers to large polypeptides. The term "peptide" typically refers to short polypeptides. Synthetic polypeptides can be synthesized, for example, using an automated polypeptide synthesizer.

The terms "identical" or percent "identity" as known in the art refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms"). "Substantial identity" refers to sequences with at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity over a specified sequence. In some aspects, the identity exists over a region that is at least about 50-100 amino acids or nucleotides in length. In other aspects, the identity exists over a region that is at least about 100-200 amino acids or nucleotides in length. In other aspects, the identity exists over a region that is at least about 200-500 amino acids or nucleotides in length. In certain aspects, percent sequence identity is determined using a computer program selected from the group consisting of GAP, BLASTP, BLASTN, FASTA, BLASTA, BLASTX, BestFit and the Smith-Waterman algorithm Various aspects of the disclosure relate to amino acid sequences. As to amino acid sequences, one of skill will recognize that individual substitutions, insertions, deletions, additions, or truncations to a nucleic acid, peptide, polypeptide, or protein sequence which alters, adds or deletes a single amino acid or a small percentage of amino acids in the encoded sequence is a "conservatively modified analog" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
  1) Alanine (A), Glycine (G);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V);
  6) Phenylalanine (F), Tyrosine (Y), Tryptophan (W);
  7) Serine (S), Threonine (T); and
  8) Cysteine (C), Methionine (M) (see, e.g., Creighton, Proteins (1984)).

As used herein, a "variant" refers to a polypeptide, protein or analog thereof that comprises at least one amino acid substitution, deletion, insertion, or modification, provided that the variant retains the biological activity of the native polypeptide. The term "variant," in some aspects, is interchangeably used with the term "mutant."

As used herein, a "fragment" of a polypeptide refers to any portion of the polypeptide smaller than the full-length polypeptide or protein expression product. Fragments are typically deletion analogs of the full-length polypeptide, wherein one or more amino acid residues have been removed from the amino terminus and/or the carboxy terminus of the full-length polypeptide. Accordingly, "fragments" are a subset of deletion analogs described below.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all.

The term "endogenous" refers to a polypeptide or polynucleotide or other compound that is expressed naturally in the host organism, or originates within a cell, tissue or organism. "Exogenous" refers to a polypeptide, polynucleotide or other compound that originates outside a cell, tissue or organism.

The term "agent" or "compound" describes any molecule, e.g., protein or pharmaceutical, with the capability of affecting a biological parameter in the disclosure. In some aspects, the disclosure includes agents which disrupt the interaction of WDR5 protein at the binding pocket or interaction surface within WDR5, wherein WDR5 binds RBBP5/MYC/KANSL2.

A "control," as used herein, can refer to an active, positive, negative or vehicle control. As will be understood by those of skill in the art, controls are used to establish the relevance of experimental results, and provide a comparison for the condition being tested.

The term "effective amount" as used herein means that amount of an agent that elicits the biological or medicinal response in a cell, tissue, organ, system, animal, or human that is being sought.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 1 to 50" is inclusive of the endpoints, 1 and 50, and all the intermediate values).

It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as about 1% to 50%, it is intended that values such as 2% to 40%, 10% to 30%, or 1% to 3%, etc., are expressly enumerated in this specification. The values listed above are only examples of what is specifically intended.

Ranges, in various aspects, are expressed herein as from "about" or "approximately" one particular value and/or to "about" or "approximately" another particular value. When values are expressed as approximations, by use of the antecedent "about," it will be understood that some amount of variation is included in the range.

The disclosure provides methods of producing mesodermal lineage cells, cardiac lineage cells, hematopoietic lineage cells, and retinal lineage cells from embryonic stem cells. In some embodiments, combinations of these cells are produced in mixed tissue organoids. In particular aspects, combinations of retinal lineage cells and cardiac lineage cells are produced together. In some embodiments, uses of such cells for research, compound screening and analysis, and therapeutics are provided. In some embodiments, kits comprising reagents to practice the methods of the disclosure are provided. In some embodiments, kits comprising the cells made by the methods of the disclosure are provided. In some embodiments, kits further comprise reagents for differentiation or use of cells (e.g., buffers, excipients, vials, containers, and the like).

The disclosure reveals a novel role for WDR5 in regulating neuroectoderm and mesoderm cell fate determination. WDR5 acts as a "temporal rheostat" that controls cell fate. When unperturbed or overexpressed, WDR5 promotes cell proliferation and retinal neuroectoderm formation. As this rheostat is adjusted by transient suppression of WDR5 for greater than 24 hours and less than 60 hours, or for about 36 to about 48 hours, and then toggled by re-expression of WDR5, retinal neuroectoderm conversion is blocked. Instead, differentiation skews toward mesoderm differentiation, as noted by formation of contractile cardiac lineage cells. Mechanistically, this rheostat function depends on a protein-protein interaction between WDR5 and RBBP5, between WDR5 and MYC, and/or between WDR5 and KANSL2.

In one embodiment, the disclosure is directed to a method for producing a mesodermal lineage cell from an ESC in culture, the method comprising disrupting the interaction of WDR5 protein with RBBP5, MYC protein, and/or KANSL2 protein in the ESC for a set period of time, and after the set period of time removing the disruption of the interaction of WDR5 protein with RBBP5 protein, MYC protein, and/or KANSL2 protein in the ESC to allow the mesodermal lineage cell to differentiate from the ESC.

In a particular embodiment, the disclosure is directed to a method for producing a mesodermal lineage cell from an ESC in culture, the method comprising disrupting the interaction of WDR5 protein with RBBP5 in the embryonic stem cell for a set period of time, and after the set period of time removing the disruption of the interaction of WDR5 protein with RBBP5 protein in the ESC to allow the mesodermal lineage cell to differentiate from the ESC.

In one embodiment, the disclosure is directed to a method for producing a mesodermal lineage cell from an ESC in culture, the method comprising turning off for a set period of time WDR5 gene expression in an ESC expressing WDR5, and turning back on WDR5 gene expression in the ESC after the set period of time allowing the mesodermal lineage cell to differentiate from the ESC. In some aspects, the set period of time is greater than about 24 hours and less than about 60 hours. In particular aspects, the set period of time is between about 36 hours and about 48 hours.

WD Repeat-Containing Protein 5 (WDR5)

WD repeat-containing protein 5 ("WDR5" or "Wdr5") (UniProtKB-P61964 (WDR5_HUMAN; NP_060058.1); also known as BMP2-induced 3-kb gene protein (SEQ ID NO: 1)), is a human WD40-repeat-containing protein present in multiple chromatin regulatory complexes, including H3K4 methyltransferases. In various aspects, human WDR5 protein is herein referred to as recombinant human WDR5 and is encoded by the nucleic acid sequence set forth in SEQ ID NO: 9. In some aspects, this human WDR5 protein is referred to as "recombinant human WDR5 protein" when it is expressed in an embryonic stem cell after introduction of a polynucleotide encoding the WDR5 protein. In some aspects, this human WDR5 protein is referred to herein as "wild type recombinant human WDR5 protein" to clarify that it is not a "mutant WDR5 protein," which comprises specific mutations in the WDR5 protein which interfere with or inhibit binding of WDR5 protein to RBBP5 protein, MYC protein, and/or KANSL2 protein.

An aspect of the disclosure is drawn to a nucleic acid encoding a human WDR5 polypeptide, e.g., a human WDR5 DNA or polynucleotide, wherein the human WDR5 DNA (e.g., the polynucleotide comprising SEQ ID NO: 9) encodes a protein that is at least 70%, 75%, 80%, 85%, 90%, 95%, 96%, 97%, 98%, 99% or 100% identical to the full length protein comprising the amino acid sequence set forth in SEQ ID NO: 1. In some aspects, the human WDR5 DNA encodes a protein that is a fragment of the WDR5 polypeptide comprising the amino acid sequence set forth in SEQ ID NO: 1, wherein the fragment comprises WDR5 biological activity. The human WDR5 DNA is transfected or transformed into embryonic stem cells in various aspects of the disclosure.

In various aspects, the disclosure includes a "mutant WDR5 protein or polypeptide" or "mutant recombinant WDR5 protein or polypeptide," including a "mutant human WDR5 protein or polypeptide." In various aspects, amino acids are substituted at various positions in the WDR5 protein to make a mutant WDR5 protein that can no longer bind RBBP5 protein, MYC protein, and/or KANSL2 protein. In some aspects, amino acids at positions 225, 240, and 268 of the amino acid sequence set forth in SEQ ID NO: 1 are substituted. In various aspects, the asparagine at position 225 is replaced with another amino acid, and in some aspects, alanine. In various aspects, the leucine at position 240 is replaced with another amino acid, and in some aspects, lysine. In various aspects, the valine at position 268 is replaced with another amino acid, and in some aspects, glutamic acid. In various aspects, therefore, the mutant recombinant WDR5 protein is hWDR5$^{N225A}$, hWDR5$^{L240K}$, or hWDR5$^{V268E}$.

WDR5 is best known as a core subunit of MLL-containing histone methyltransferase (HMT) complexes—which includes the WDR5-RBBP5 subcomplex—that catalyze lysine 4 methylation on histone H3 (H3K4me) (Dou et al., 2006; Rao and Dou, 2015). WDR5 also promotes lysine 16 acetylation on histone 4 (H4K16Ac) through its association with the acetyltransferase MOF (Dou et al., 2005; Li et al., 2012). Both WDR5-mediated H3K4me and H4K16Ac on chromatin are linked to transcription (Dou et al., 2006; Dou et al., 2005; Li et al., 2012).

WDR5 contains two binding surfaces on opposite sides of the protein: one binding surface interacts with H3 N-terminal tail, MLL1, KANSL1, long non-coding RNAs and MBD3C (Dias et al., 2014; Ee et al., 2017; Yang et al., 2014), while the other binds RBBP5, MYC (for example, UniProtKB-P01106) and KAT8 Regulatory NSL Complex Subunit 2 (KANSL2; for example, UniProtKB-Q9H9L4) (Chantada et al., 2011; Dias et al., 2014; Odho et al., 2010). Due to its structural association with MLL in mixed lineage leukemia as well as with MYC oncoproteins, WDR5 has emerged as a druggable therapeutic target in cancer (Cao et al., 2014; Carugo et al., 2016; Thomas et al., 2015b).

An evolutionarily-conserved protein, WDR5 executes cell type-specific roles during development through distinct mechanisms. WDR5 regulates pluripotent stem cell (PSC) self-renewal through interacting with Oct4 or binding to long non-coding RNAs (Ang et al., 2011; Yang et al., 2014). As a downstream target for Oct4 and CCCTC binding protein, forced expression of WDR5 facilitates induced pluripotent stem cell (iPSC) reprogramming (Ang et al., 2011; Wang et al., 2017). WDR5 loss-of-function in *X. laevis* embryos results in defective hematopoietic, gut and somatic development (Wysocka et al., 2005). As a bone morphogenetic protein 2 (BMP-2)-induced protein, overexpression of WDR5 accelerates osteoblast differentiation through activation of WNT pathway during mouse embryonic bone development (Gori et al., 2006).

The retina is an attractive organ to dissect functions of epigenetic regulators including WDR5 for a variety of reasons. WDR5 stimulates adult retinal photoreceptor cell regeneration in planarians (Hubert et al., 2013). Since developmental principles often underlie regeneration, the derivation of relatively pure, 3D retinal organoids from ESCs provides a robust platform to better understand how WDR5 exerts lineage specific effects (Eiraku et al., 2011; Nakano et al., 2012). Improved mechanistic understanding of this phenomenon could have clinical impact. Indeed, the number of individuals in developed countries affected by degenerative retinal diseases such as age-related macular degeneration (AMD) rivals the number affected by all forms of cancer. Unlike cancer, no effective treatments exist for 90% of those affected by AMD. PSC-derived retinal cell transplantation has emerged as the first PSC-based intervention for any human disease (Mandai et al., 2017; Schwartz et al., 2012; Schwartz et al., 2015). However, these interventions continue to linger in the clinical trial phase, efficacy remains unknown, tumor risk is a concern, and some crucial cell types that die in AMD, such as cone photoreceptors, cannot be efficiently derived from human PSCs (Mandai et al., 2017; Merkle et al., 2017; Rao et al., 2017). A better understanding of how WDR5 plays a role in retinal development would expand our mechanistic understanding of how epigenetic proteins function in a lineage-specific manner, and could have translational implications for developing effective and safe PSC-based retinal therapies.

WDR5 controls embryonic stem cell (ESC)-to-retinal progenitor cell (Rx (+) RPC) differentiation. Transient deletion of WDR5 under ESC-to-retinal organoid differentiation conditions leads to an ESC lineage switch from neuroectoderm (retina/RPC) to mesoderm (cardiac, hematopoietic cells). Introduction of WDR5 mutants that disrupt its interaction with RBBP5/MYC/KANSL2 results in a loss of retinal ectoderm differentiation. In one aspect, WDR5 and RBBP5 form a module that stimulates retinal neuroectoderm formation. The disclosure provides a WDR5-driven, tractable stem cell/organoid-based platform that enables interrogation of mechanisms that drive neuroectoderm versus mesoderm fate determination. The disclosure elucidates a cell lineage-specific role for the broadly expressed protein WDR5 during early ESC differentiation.

WDR5 is purported to assemble into a number of chromatin regulatory complexes including the MLL/SET methyltransferases that methylate H3K4 and the MOF/NSL histone acetyltransferases that acetylate histone H4 (Thomas et al., Molecular Cell 58(3):440-452, 2015; "Thomas"). In some aspects, WDR5 is modulated at the binding site to inhibit WDR5 binding with MYC (including c-MYC), RBBP5 and/or KANSL2. In some embodiments, the disclosure includes targeted disruption of WDR5 binding with MbIIIb and/or MYC, KANSL2, and RBBP5, including targeted disruption at particular amino acid sequences including, in some aspects, the LDVV residues of KANSL2, VDVT residues of RBBP5, and IDVV of c-MYC. Id.

MYC binds WDR5 via an evolutionarily conserved "MYC box IIIb" motif that engages a shallow, hydrophobic cleft on the surface of WDR5. Id. Structure-guided mutations in MYC that disrupt interaction with WDR5 attenuate binding of MYC. Id. Conserved hydrophobic residues in the MbMb core mediate interaction with WDR5. Id. In some embodiments, the disclosure includes targeted disruption of WDR5 binding with MbMb and/or MYC, KANSL2, and RBBP5, including targeted disruption of binding at these conserved amino acid residues to modulate the fate of ESCs.

In various aspects, therefore, the amino acid sequences targeted for disruption include the DDLDVV (SEQ ID NO: 2) or LDVV (SEQ ID NO: 3) residues of KANSL2; the EEVDVT (SEQ ID NO: 4), EVDVT (SEQ ID NO: 5), or VDVT (SEQ ID NO: 6) residues of RBBP5, and the EEIDVV (SEQ ID NO: 7) or IDVV (SEQ ID NO: 8) residues of MYC. Id. In more particular aspects, the disclosure includes the targeted disruption of binding at the site comprising amino acids LDVV (SEQ ID NO: 3), VDVT (SEQ ID NO: 6), and/or IDVV (SEQ ID NO: 8).

In various aspects, the methods of the disclosure include the use of mutant WDR5 nucleic acid (encoding mutant WDR5 polypeptide comprising mutations that interfere with binding MbMb and/or MYC, KANSL2, and RBBP5 at the binding pocket) to make single organoids comprising mixed lineage cells, i.e., retinal lineage cells and cardiac lineage cells.

Figure 3A:
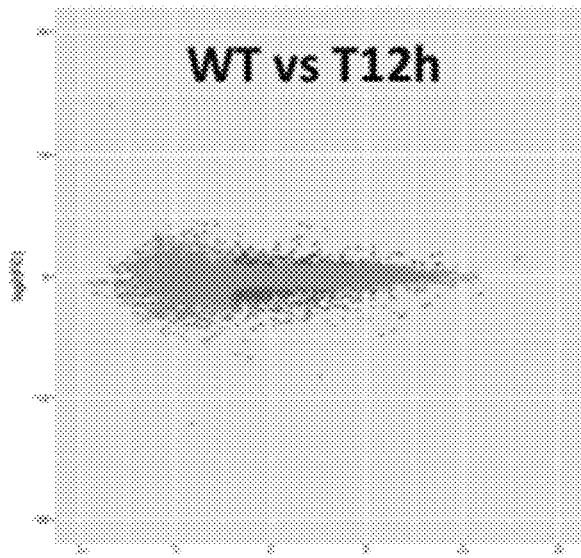
FIGS. 3A-3E. Early and late induction of exogenous hWDR5 in mWdr5 KO EBs regulates distinct global gene transcription profiles.

Thomas (supra) reported the X-ray crystal structure of WDR5 in complex with an MbMb peptide at 1.9 Å resolution. Within the WDR5 cleft are two hydrophobic pockets that mediate critical interactions with residues in the EEIDVV core: pocket 1 is created by tyrosine 228 (Y228), leucine 240 (L240), and leucine 249 (L249) of WDR5, which accommodate isoleucine 262 (I262) of MYC; pocket 2 is created by phenylalanine 266 (F266) and valine 268 (V268) of WDR5, which accommodate side chains of valines 264 and 265 (V264; V265) of MYC (FIG. 3F). The complex is also stabilized by intramolecular hydrogen bonds, including those involving the side chains of asparagine 225 (N225) and glutamine 289 (Q289) of WDR5. Accordingly, mutation of residues N225, L240, or V268 in WDR5 blocks interaction of recombinant WDR5 with recombinant full-length MYC in vitro, demonstrating that the MbMb interaction surface defined in the structure is relevant to interaction of WDR5 with the entire MYC protein. Id.

Thus, the disclosure includes the use various DNA constructs to practice the methods of the invention. These constructs include, but are not limited to, the following:

"hWDR5$^{Mut}$" as used herein is used to represent expression of a mutant (Mut) human WDR5 polypeptide.

"hWDR5$^{Dox}$" as used herein is used to represent expression of a human WDR5 polypeptide that is expressed conditionally when doxycycline (Dox) is added to the culture.

"mWdr5$^{KO}$" as used herein is used to represent a knockout (KO) state of mouse Wdr5 gene, due to inactivation of the endogenous mouse Wdr5 gene. In exemplary aspects, the mWdr5 gene is knocked out using CRISPR/Cas9 mediated inactivation.

"hWDR5$^{Dox}$;mWdr5$^{KO}$ ESC clones" as used herein is used to represent an ESC line(s) in which endogenous mouse Wdr5 has been inactivated (knocked out), and in which expression of a human WDR5 polypeptide is expressed conditionally when doxycycline (Dox) is added to the culture.

"hWDR5$^{Mut}$; hWDR5$^{DOX}$; mWdr5$^{KO}$ ESC clones" as used herein is used to represent an ESC line(s) in which endogenous mouse Wdr5 polypeptide has been inactivated (knocked out); in which expression of a mutant (Mut) human WDR5 polypeptide (as described herein) is expressed constitutively; and in which expression of a recombinant human WDR5 polypeptide (e.g., wild type recombinant human WDR5 polypeptide) is expressed conditionally when doxycycline (Dox) is added to the culture. In aspects of the disclosure, these cells are used to produce an organoid comprising a mixed cell lineage comprising mesodermal lineage cells and cardiac lineage cells within a single organoid, i.e., "hWDR5$^{Mut}$; hwDR5$^{Dox}$; mWdr5$^{KO}$ organoid."

"hWDR5$^{N225A}$" as used herein is used to represent expression of a mutant (Mut) human WDR5 polypeptide that is expressed conditionally when doxycycline (Dox) is added to the culture. Specifically, Dox induces expression of a mutant human WDR5 polypeptide in which Asparagine at position 225 of the hWDR5 polypeptide is replaced with Alanine.

"hWDR5$^{L240K}$" as used herein is used to represent expression of a mutant (Mut) human WDR5 polypeptide that is expressed conditionally when doxycycline (Dox) is added to the culture. Specifically, Dox induces expression of a mutant human WDR5 polypeptide in which Leucine at position 240 of hWDR5 is replaced with Lysine.

"hwDR5$^{V268E}$" as used herein is used to represent expression of a mutant (Mut) human WDR5 peptide that is expressed conditionally when doxycycline (Dox) is added to the culture. Specifically Dox induces expression of a mutant human WDR5 polypeptide in which Valine at position 268 of hWDR5 is replaced with Glutamic Acid.

"hWDR5$^{Q289E}$" as used herein is used to represent expression of a mutant (Mut) human WDR5 polypeptide that is expressed conditionally when doxycycline (Dox) is added to the culture. Specifically, Dox induces expression of a mutant human WDR5 polypeptide in which Glutamine at position 289 of hWDR5 is replaced with Glutamic Acid.

"hWDR5$^{F133Y}$" as used herein is used to represent expression of a mutant (Mut) human WDR5 polypeptide that is expressed conditionally when doxycycline (Dox) is added to the culture. Specifically, Dox induces expression of a mutant human WDR5 polypeptide in which Phenylalanine at position 289 of hWDR5 is replaced with Tyrosine.

Similar abbreviations as set forth above may be used to represent expression of various mutants in the manner described herein above.

Odho et al., (J. Biol. Chem. 285:32967-76, 2010; "Odho") and Dias et al. (Genes & Dev. 28:929-42, 2014; "Dias") also identified this novel WDR5-binding site that recruits RBPP5 through a conserved motif. Odho likewise characterized this interaction by x-ray crystallography and showed that it is fundamental to the assembly of the complex and to the regulation of methyltransferase activity. Because the targeted disruption of the WDR5 binding site is included in an embodiment of the disclosure, Thomas, Odho, and Dias are incorporated herein in their entireties because each of these references provides extensive disclosure regarding the binding pocket targeted for disruption.

The disclosure shows WDR5 controls embryonic stem cell (ESC)-to-retinal progenitor cell (Rx (+) RPC) differentiation. Transient deletion of WDR5 under ESC-to-retinal organoid differentiation conditions leads to an ESC lineage switch from neuroectoderm (retina/RPC) to mesoderm (cardiac, hematopoietic cells). Introduction of WDR5 mutants that disrupt a pocket necessary for interaction with RBBP5, MYC, or KANSL2 results in a loss of retinal ectoderm differentiation. The disclosure provides a WDR5-driven, tractable stem cell/organoid-based platform that enables interrogation of mechanisms that drive neuroectoderm versus mesoderm fate determination. Collectively, the disclosure elucidates a cell lineage-specific role for the broadly expressed WDR5 protein during early ESC differentiation.

Any means for regulating WDR5 expression in a cell may be used, including both direct and indirect modulation. In various aspects, these means include, for example, modulating WDR5 expression at the transcriptional, translational or post-translational level, modulating the persistence or breakdown of messenger RNA, or modulating the persistence or breakdown of protein. In various aspects, these means include the use of WDR5 agonists and compounds which disrupt a WDR5 pocket necessary for WDR5 interaction with RBBP5, MYC, or KANSL2 in the embryonic stem cell. In some aspects, WDR5 interaction with RBB5 is disrupted. In some aspects, WDR5 interaction with MYC is disrupted. In some aspects, WDR5 interaction with KANSL2 is disrupted. In some aspects, WDR5 interaction with a combination of RBBP5, MYC, and/or KANSL2 is disrupted. In some aspects, the disclosure includes, but is not limited to using a transactivator protein to modulate or regulate WDR5 protein expression in a cell. In exemplary aspects, doxycycline (Dox) is modulated to control WDR5 protein expression in the cell. In further exemplary aspects, Dox is used to turn on and turn off WDR5 expression at particular time points in the cell. Such means for regulating WDR5 expression are described in further detail below.

In some embodiments, WDR5 expression in the embryonic stem cell is modulated to affect differentiation of the stem cell towards mesodermal lineages. In some embodiments, WDR5 expression in the embryonic stem cell is modulated to affect differentiation of the stem cell towards differentiating into a combination of cells comprising mesodermal lineages and retinal lineages.

In some aspects of the disclosure, WDR5 expression in embryonic stem cells and embryoid body cells is regulated using an inducible gene expression system.

Gene Transfection, Regulation, and Expression

Transfecting or transfection refers to the process of introducing nucleic acid into a cell or tissue. A "transfected cell" is a host cell into which (or into an ancestor of which) has been introduced, by means of recombinant DNA techniques, a recombinant DNA or the recombinant gene. Transfection of a host cell with recombinant DNA may be carried out by conventional techniques as are well known to those skilled in the art. In various aspects, the polynucleotide comprising the DNA sequence set forth in SEQ ID NO: 9 is introduced into the embryonic stem cell.

Any means for making hWDR5$^{Dox}$; mWdr5$^{KO}$ cells may be used for practicing the methods of the disclosure. In some aspects, the following protocol is used to make hWDR5$^{Dox}$; mWdr5$^{KO}$ cells. Doxycycline (Dox)-inducible PiggyBac plasmids including pPBhCMV1cHApA, pPBCAG-rtTM2-IN and transposase were kindly provided by Dr. Hitoshi Niwa (Kumamoto University, Japan). Full-length human wild type WDR5 are cloned to pPBhCMV1cHApA plasmid. Flag-tagged wild type are sub-cloned into non-inducible piggyBac plasmid (Addgene, #48754). For mESC transfection, 20 µg endotoxins-free plasmid DNA are electroporated to 5×10^6 ESCs using mouse ES cell NUCLEOFECTOR® kit (Lonza). Antibiotic-resistant ESC colonies are selected for 5 days and pooled or single cell derived clones are picked for further characterization. To generate CRISPR-Cas9 mediated mWDR5 knockout (KO) plasmid, mWdr5 guide RNA sequence (TGTGAAGTTCAGCCCCAATG (SEQ ID NO: 16)) was cloned into pSpCas9(BB)-2A-Puro (PX459) V2.0 plasmid (Addgene, #62988). To generate mWdr5 KO ESC clones harboring with inducible exogenous hWDR5 rescue platform)(hWDR5$^{Dox}$;mWdr5$^{KO}$), Dox-inducible hWDR5 pooled ESC populations are subjected to a second round of transfection with mWdr5 KO plasmid and selected with puromycin (2 µg/ml) in the presence of Dox (2 µg/ml). Single cell derived ES clones are picked, expanded, and maintained in presence of Dox. Sanger sequencing is used to determine DNA editing at expected sites and homozygous Indel mutations with frameshift are selected as mWdr5 KO ESC clones.

Any means for making cells expressing mutant WDR5 genes may be used in for practicing the methods of the disclosure. In some aspects, organoids expressing mixed lineage cells are prepared according to the following protocol. Doxycycline (Dox)-inducible PiggyBac plasmids including pPBhCMV1cHApA, pPBCAG-rtTM2-IN and transposase were kindly provided by Dr. Hitoshi Niwa (Kumamoto University, Japan). Full-length human wild type WDR5 is cloned to pPBhCMV1cHApA plasmid. Flag tagged mutant forms of WDR5 (F133Y, N225A, L240K, V268E, Q289E and 1305V; see SEQ ID NOs: 10-15) are sub-cloned into non-inducible piggyBac plasmid (Addgene, #48754). For mESC transfection, 20 µg endotoxin-free plasmid DNA is electroporated to 5×10^6 ESCs using mouse ES cell NUCLEOFECTOR® kit (Lonza). Antibiotic-resistant ESC colonies are selected for five days and pooled or single cell derived clones are picked for further characterization. To generate CRISPR-Cas9 mediated mWDR5 knockout (KO) plasmid, mWdr5 guide RNA sequence (TGTGAAGTTCAGCCCCAATG (SEQ ID NO: 16)) is cloned into pSpCas9(BB)-2A-Puro (PX459) V2.0 plasmid (Addgene, #62988). To generate mWdr5 KO ESC clones harboring an inducible exogenous hWDR5 rescue platform) (hWDR5$^{Dox}$;mWdr5$^{KO}$), Dox-inducible hWDR5 pooled ESC populations are subjected to a second round of transfection with mWdr5 KO plasmid and selected with puromycin (2 µg/ml) in the presence of Dox (2 µg/ml). Single cell derived ES clones are picked up, expanded and maintained in the presence of Dox. Sanger sequencing is used to determine DNA editing at expected sites and homozygous Indel mutations with frameshift are selected as mWdr5 KO ESC clones.

Transformation refers to the process of genetic alteration of a cell resulting from the direct uptake and incorporation of exogenous genetic material into the cell from its surroundings through the cell membrane(s). Transformation may be carried out by conventional techniques as are well known to those skilled in the art.

Any means for regulating gene transcription may be used in the methods of the disclosure. In the context of gene regulation, transactivation is the increased rate of gene expression triggered either by biological processes or by artificial means. The transactivator gene expresses a transcription factor that binds to specific promoter region of DNA. By binding to the promoter region of a gene, the transcription factor causes that gene to be expressed. In the context of receptor signaling, transactivation occurs when one or more receptors activate yet another; receptor transactivation may result from the crosstalk of signaling cascades.

The ability to artificially control gene expression in eukaryotic cells is essential for many applications in basic molecular biology, including cell biology, biochemical or biomedical research. Most currently available gene regulatory systems are based on chemical inducer molecules (e.g. tetracycline) that must enter a cell to bind a target protein and activate its transcriptional activity.

Any means for regulating gene expression in a cell may be used in the methods of the disclosure. In some aspects, the inducible gene expression system is via tetracycline-controlled transcriptional activation. Tetracycline-controlled transcriptional activation is a method of inducible gene expression where transcription is reversibly turned on or off in the presence of the antibiotic tetracycline or one of its derivatives (e.g., doxycycline (Dox)). The methods of the disclosure may include both Tet-On and Tet-Off systems for inducible gene expression. Tet-Off activates expression in the absence of Dox, whereas Tet-On activates in the presence of Dox.

The Tet-Off system makes use of the tetracycline transactivator (tTA) protein. In a Tet-Off system, expression of TRE-controlled genes can be repressed by tetracycline and its derivatives. They bind tTA and render it incapable of binding to TRE sequences, thereby preventing transactivation of TRE-controlled genes. In the Tet-Off system, the removal of Dox from the system initiates transcription of the TRE-controlled genes. A Tet-On system works similarly, but in the opposite fashion. While in a Tet-Off system, tTA is capable of binding the operator only if not bound to tetracycline or one of its derivatives, such as doxycycline, in a Tet-On system, the rtTA protein is capable of binding the operator only if bound by a tetracycline. In the Tet-On system, the introduction of Dox into the system initiates transcription of the TRE-controlled genes. In exemplary aspects, the Tet-On system is used to regulate the expression of recombinant WDR5 in the ESC. Thus, in the presence of Dox in the cell culture medium, recombinant WDR5 is expressed. In some aspects, doxycycline (Dox) is used. In some aspects, Dox is used at a concentration from about 0.5 to about 2.0 micrograms per milliliter.

In exemplary aspects, hWDR5$^{Dox}$;mWdr5$^{KO}$ ESCs are maintained in Dox-containing ESC media. Dox is removed upon differentiation (EB0) and is added back to EBs at 12 h (at T12h or "early induction of exogenous hWDR5") or after 24h, including at 36h and 48h (at T36h or at T48h or "late induction of exogenous hWDR5") after differentiation.

In various aspects, late induction of exogenous WDR5 after differentiation (or after EB0) takes place for a set period of time greater than 24 hours and less than 60 hours. In some aspects, the set period of time is between 25 hours and 59 hours. In some aspects, the set period of time is between 26 hours and 58 hours. In some aspects, the set period of time is between 27 hours and 57 hours. In some aspects, the set period of time is between 28 hours and 56 hours. In some aspects, the set period of time is between 29 hours and 55 hours. In some aspects, the set period of time is between 30 hours and 54 hours. In some aspects, the set period of time is between 31 hours and 53 hours. In some aspects, the set period of time is between 32 hours and 52 hours. In some aspects, the set period of time is between 33 hours and 51 hours. In some aspects, the set period of time is between 34 hours and 50 hours. In some aspects, the set period of time is between 35 hours and 49 hours. In some aspects, the set period of time is between 36 hours and 48 hours.

In some aspects, the set period of time is about 25 hours, about 26 hours, about 27 hours, about 28 hours, about 29 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 49 hours, about 50 hours, about 51 hours, about 52 hours, about 53 hours, about 54 hours, about 55 hours, about 56 hours, about 57 hours, about 58 hours, or about 59 hours.

Gene Silencing

In some aspects of the disclosure, expression of a gene in a cell is silenced. In various aspects, the term "silenced" is interchangeable with "suppressed," or "knocked out." Gene silencing is the interruption or suppression of the expression of a gene at transcriptional or translational levels. A person of ordinary skill in the art is aware of many techniques to selectively turn off or silence specific genes for various reasons, and means for silencing gene expression in a cell may be used in the methods of the disclosure. In other words, the disclosure includes the use of any system known in the art to silence, suppress, or knock out gene expression so that the resulting polypeptide is not expressed by the cell.

Any means for silencing gene expression in a cell may be used in the methods of the disclosure. In some aspects, silencing of recombinant hWDR5 expression is done by the use of an inducible gene expression system. In exemplary aspects, the Tet-On system, as described herein above, is used to silence the expression of recombinant hWDR5 in the embryonic stem cells and/or the embryoid body cells. Tet-On activates in the presence of Dox. Thus, in the absence of Dox, hWDR5 gene is expression is silenced. In other words, Dox is used as an inducible protein to turn on the expression of recombinant hWDR5. In culture conditions where Dox is absent, no hWDR5 expression occurs.

In some aspects, gene silencing is carried out by silencing RNA. In some aspects, RNA is silenced using a short hairpin RNA or small hairpin RNA, wherein the terms "short" or "small" are used interchangeably. shRNA is an artificial RNA molecule with a tight hairpin turn that can be used to silence target gene expression via RNA interference (RNAi). Expression of shRNA in cells is typically accomplished by delivery of plasmids or through viral or bacterial vectors. In some aspects, shRNA sequences are encoded in a DNA vector that can be introduced into cells via plasmid transfection or viral transduction. Once the vector has integrated into the host genome, the shRNA is then transcribed in the nucleus by polymerase II or polymerase III depending on the promoter choice. The product mimics pri-microRNA (pri-miRNA) and is processed by Drosha. The resulting pre-shRNA is exported from the nucleus by Exportin 5. This product is then processed by Dicer and loaded into the RNA-induced silencing complex (RISC). The sense (passenger) strand is degraded. The antisense (guide) strand directs RISC to mRNA that has a complementary sequence. In the case of perfect complementarity, RISC cleaves the mRNA. In the case of imperfect complementarity, RISC represses translation of the mRNA. In both of these cases, the shRNA leads to target gene silencing.

In some aspects, RNA is silenced using small interfering RNA (siRNA), sometimes known as short interfering RNA or silencing RNA. siRNA is a class of double-stranded RNA molecules, 20-25 base pairs in length, similar to miRNA, and operating within the RNA interference (RNAi) pathway. siRNA interferes with the expression of specific genes with complementary nucleotide sequences by degrading mRNA after transcription, preventing translation.

In some aspects, RNA is silenced using CRISPR/Cas genome editing techniques. For example, genome editing, in some aspects, is carried out using the CRISPR-Cas9 system or the CRISPRi-Cas9 system. The CRISPR-Cas9 system uses the protein Cas9 to delete a precise part of the genome by making small cuts in a cell's DNA. By delivering the Cas9 nuclease complexed with a synthetic guide RNA (gRNA) into a cell, the cell's genome can be cut at a desired location, allowing existing genes to be removed and/or new ones added. CRISPRi goes beyond this by using a special deactivated version of the Cas9 protein along with an inhibitor protein, KRAB. The two proteins then sit at the target spot within the genome and suppress gene expression without any cuts. The end result is a more consistent gene suppression compared to cutting it outright.

In some aspects, endogenous mWdr5 is silenced in ESC using the following protocol. Doxcycline (Dox)-inducible PiggyBac plasmids including pPBhCMV1cHApA, pPB-CAG-rtTM2-IN and transposase were kindly provided by Dr. Hitoshi Niwa (Kumamoto University, Japan). Full-length human wild type WDR5 is cloned to pPBhCMV1cHApA plasmid. Flag-tagged mutant forms of WDR5 (F133Y, N225A, L240K, V268E, Q289E and I305V) are sub-cloned into non-inducible piggyBac plasmid (Addgene, #48754). For mESC transfection, 20 µg endotoxin-free plasmid DNA is electroporated to 5×10^6 ESCs using mouse ES cell NUCLEOFECTOR® kit (Lonza). Antibiotic-resistant ESC colonies are selected for 5 days and pooled or single cell derived clones are picked for further characterization. To generate CRISPR-Cas9 mediated mWDR5 knockout (KO) plasmid, mWdr5 guide RNA sequence (TGTGAAGTTCAGCCCCAATG; SEQ ID NO: 16) is cloned into pSpCas9(BB)-2A-Puro (PX459) V2.0 plasmid (Addgene, #62988). To generate mWdr5 KO ESC clones harboring an inducible exogenous hWDR5 rescue platform (hwDR5$^{Dox}$;mwdr5$^{KO}$) Dox-inducible hWDR5 pooled ESC populations are subjected to a second round of transfection with mWdr5$^{KO}$ plasmid and selected with puromycin (2 µg/ml) in the presence of Dox (2 µg/ml). Single cell derived ES clones are picked, expanded, and maintained in the presence of Dox. Sanger sequencing is used to determine DNA editing at expected sites and homozygous Indel mutations with frameshift are selected as mWdr5$^{KO}$ ESC clones.

Embryonic Stem Cells

Embryonic stem cells (ESCs) are pluripotent stem cells derived from the inner cell mass of a blastocyst, an early-stage pre-implantation embryo. As used herein, "embryonic stem cell (ESC)" is interchangeable with "pluripotent stem cell (PSC)," and includes induced PSC and all other kinds of PSCs.

In some aspects, ESCs are derived from embryos of non-human mammalian species. In some aspects, the non-human mammalian species are mouse, rat, hamster, guinea pig, rabbit, dog, cat, cow, pig, sheep, goat, or horse. In some aspects, ESCs are human. In exemplary aspects, ESCs are mouse. In some aspects, ESCs are derived from embryos that develop from eggs that have been fertilized in vitro—in an in vitro fertilization clinic—and then donated for research purposes with informed consent of the donors. In some aspects, such ESCs are made in the lab. In some aspects, such ESCs are commercially available. In exemplary aspects, Rx:GFP K/I EB5 mouse ESCs, a subline of mouse embryonic stem cell line, EB5 (129/Ola), in which GFP gene is knocked-in under Rx/Rax gene promoter, are obtained from RIKEN Cell Bank (Ibaraki, Japan).

ESCs are pluripotent, meaning they are able to grow (i.e. differentiate) into all derivatives of the three primary germ layers: ectoderm, endoderm and mesoderm. In other words, they can develop into each of the more than 200 cell types of the adult body as long as they are specified to do so. ESCs are distinguished by two distinctive properties: their pluripotency, and their ability to replicate indefinitely. Pluripotency distinguishes ESCs from adult stem cells found in adults. While ESCs can generate all cell types in the body, adult stem cells are multipotent and can produce only a limited number of cell types.

Pluripotency is the ability of a cell to differentiate into any cell type. The ability to induce pluripotency in cells from an individual provides a valuable tool for developmental biology studies and disease research studies, and could ultimately be applied to personalized stem cell therapy. Some examples of pluripotency markers include, but are not limited to, Oct4, Klf4, Sox2, c-Myc, Esrrb, Nr5a2, C/EBPa, Lin28, and Nanog. In various aspects of the disclosure, cells are tested for the presence of one or more of these pluripotency markers.

In exemplary aspects, the ESC line used (Rx:GFP K/I EB5 mouse ESCs) carries a blasticidin-S resistance gene at the Oct-3/4 locus for selection of Oct-3/4-expressing undifferentiated cells, thus ensuring pluripotency. Alternatively, ESC lines are stained by immunohistochemistry with antibodies to detect pluripotency markers to ensure a pluripotent state in all cells. In some aspects, these pluripotency markers include, but are not limited to, Oct4 and Nanog.

In some embodiments of the disclosure, ESCs are cultured in adherent culture to form monolayers. In various embodiments of the disclosure, ESCs are cultured in media in non-adherent, suspension, or three dimensional (3D) culture to generate colonies forming organoids or embryoid bodies.

Organoids/Embryoid Bodies

In various embodiments, organoids are produced from the ESCs in the methods of the disclosure. For the purposes of this disclosure, the terms "organoids," "embryoid bodies (EBs)," and "EBs" are used interchangeably. In some embodiments, organoids are necessary intermediates to make mesodermal lineage cells. In some embodiments, mesodermal lineage cells are made in monolayers and do not require organoids.

In various aspects, the organoids of the disclosure comprise mesodermal lineage cells, hematopoietic lineage cells, cardiac lineage cells, retinal lineage cells, or mixed lineage cells. An organoid is a miniaturized and simplified version of an organ produced in vitro in three dimensions that shows realistic micro-anatomy. Organoids are derived from one or a few cells from a tissue, ESCs, or induced pluripotent stem cells, which can self-organize in three-dimensional culture owing to their self-renewal and differentiation capacities.

Organoid formation generally requires culturing the stem cells or progenitor cells in a 3D medium (Lancaster et al., Science. 345 (6194): 1247125, 2014). In some aspects, the 3D medium is made using an extracellular matrix hydrogel Matrigel. In some aspects, organoid bodies are made through embedding stem cells in the 3D medium. Id. In some aspects, when pluripotent stem cells are used for the creation of the organoid, the cells are allowed to form embryoid bodies. Id. Those embryoid bodies are then pharmacologically treated with patterning factors or manipulated according to methods of the disclosure to drive the formation of the desired organoid identity. Id. In some aspects, pluripotent stem cells are used for the creation of the organoid but are not allowed to form embryoid bodies.

Embryoid Body Cells

Embryoid body cells are derived from ESCs. In some embodiments of the disclosure, ESCs are dissociated and plated in serum-free media in the absence of Dox so that expression of WDR5 is silenced or turned off. At that moment, ESCs are transitioned to differentiation into early embryoid body cells, and this is known as EB day 0 ("EB0"). As used herein, EB day 0 is the time at which there is removal of a cytokine maintaining mouse embryonic stem cells at undifferentiated state leukemia inhibitory factor (LIF) and the ESCs are resuspended (5,000 cells in 5% knockout serum replacement containing media in low attachment 96 well plate).

In some aspects, matrigel is added at EB1 to 96 well plates. In some aspects, at greater than 24 and lesser than 60 hours post differentiation, doxycycline is added to 96 well plate to induce WDR5 expression. In various aspects, doxycycline is added at about 0.5 to about 2.0 micrograms per milliliter to turn on expression of recombinant WDR5 in the cell. In some aspects, at about 36 to about 48 hours post differentiation, doxycycline (at about 2 ug/ml) is added to 96 well plate to induce WDR5 expression. In some aspects, at EB6 or EB9, organoids are resuspended in single cell solution and seeded to commercially available secondary hematopoietic cell differentiation colony forming unit assay.

In various aspects, therefore, it follows that EB1 is an embryoid body cell 1 day after EB0, or one day after the ESC is transitioned to differentiation. Accordingly, EB2, EB3, EB4, EB5, EB6, EB7, EBB, EB9, EB10, EB11, EB12, EB13, EB14, EB15, and the like are the terms used for an embryoid body cell 2, 3, 4, 5, 6, 7, 8, 9, 10, 11, 12, 13, 14, and 15 days, respectively, after the ESC is transitioned to differentiation.

Mesodermal Lineage Cells

In various embodiments, the disclosure includes mesodermal lineage cells (alternately referred to herein, in various aspects, as mesodermal progenitor cells) and methods for producing mesodermal lineage cells. The mesoderm is one of the three germinal layers that appears in the third week of embryonic development (in humans), formed through a process called gastrulation. The mesoderm is the middle of the three germ layers, or masses of cells lying between the ectoderm and endoderm, which appears early in the development of an animal embryo. In vertebrates, the mesoderm subsequently gives rise to muscle, connective tissue, cartilage, bone, notochord, blood, bone marrow, lymphoid tissue, and to the epithelia of blood vessels, lymphatic vessels, body cavities, kidneys, ureters, gonads, genital ducts, adrenal cortex, and certain other tissues.

In exemplary aspects, to identify mesodermal lineage cells, Day 9 organoids are harvested and fixed with 4% paraformaldehyde at 4° C. overnight. EBs are sent to ULAM (Unit for Laboratory Animal Medicine) at the University of Michigan for paraffin processing, embedding, and sectioning. Antigen unmasking on slides is carried out using citric acid methods, as prescribed previously (Gage et al, Hum Mol Genet. 2005; 14: 3347-3359). Immuostaining is performed by combining of VECTASTAIN® ABC-HRP kit (Vector Laboratories) and TSA™ Kit #24, with HRP-Streptavidin and Alexa Fluor 568 Tyramide (ThermoFisher Scientific). Primary antibodies used for detecting mesoderm-lineage cells include, but are not limited to, the following: anti-N-cadherin (mouse/monoclonal/1:2000, BD), anti-cardiac troponin T (CT3 clone, mouse/monoclonal/1:100, Developmental Studies Hybridoma Bank), anti-myosin heavy chain antibody (MF20 clone, mouse/monoclonal/1:100, Developmental Studies Hybridoma Bank), and brachyury/T (R&D Systems). Counter nuclear staining is performed with DAPI (Molecular Probes). Control sections are incubated without primary antibodies. Four representative pictures from different fields are taken and recorded under a fluorescence microscope (Olympus DP73).

In some aspects, the mesodermal lineage cells disclosed herein are maintained in culture for at least about 1, about 2, about 3, about 4, about 5, about 6, about 7, about 8, about 9, about 10, about 11, about 12, about 13, about 14, about 15, about 16, about 17, about 18, about 19, or about 20 days. In some aspects, the mesodermal lineage cells are maintained in culture for about six to about nine days. In some aspects, the mesodermal lineage cells are maintained in culture for up to about 9 days, about 10 days, about 11 days, about 12 days, about 13 days, about 14 days, about 15 days, about 16 days, about 17 days, about 18 days, about 19 days, or about 20 days. In some aspects, the mesodermal lineage cells are maintained in culture for about six to about nine days. In some aspects, the mesodermal lineage cells are maintained in culture for up to about 16 days. In some aspects, the mesodermal lineage cells are maintained in culture for about six to about 16 days.

Hematopoietic Lineage Cells

In various embodiments, the disclosure includes hematopoietic lineage cells (alternately referred to herein, in various aspects, as hematopoietic progenitor cells) and methods for producing hematopoietic lineage cells. The term "hematopoietic lineage cell" is meant to encompass all types of immature and mature blood cells. Hematopoietic lineage cells are derived from mesoderm and located in the red bone marrow, which is contained in the core of most bones. Hematopoietic lineage cells give rise to blood cells through the process of hematopoiesis. Hematopoiesis is the process by which all mature blood cells are produced. In vertebrates, the vast majority of hematopoiesis occurs in the bone marrow and is derived from a limited number of hematopoietic lineage cells that are multipotent and capable of extensive self-renewal.

In exemplary aspects, to identify hematopoietic lineage cells and secondary hematopoietic cell differentiation, the following experiments are carried out. Day 6 or 9 organoids, are re-suspended and trypsinized to single cell suspension. $1\times10^5$ cells are seeded to methylcellulose-based semisolid media, M3234 (Stem Cell Technologies), in the presence of IL-3 (10 ng/ml), SCF (10 ng/ml) and GM-CSF (10 ng/ml). After 9 days of differentiation, resultant colony forming units (CFU) are counted under microscope (OLYMPUS IX73).

Cardiac Lineage Cells

In various embodiments, the disclosure includes cardiac lineage cells (alternately referred to herein, in various aspects, as cardiac progenitor cells or cardiomyocyte progenitor cells) and methods for producing cardiac lineage cells. The term "cardiac lineage cell" is meant to encompass all types of immature and mature cardiac cells. The disclosure provides methods of producing cardiac lineage cells by late induction of WDR5 (including hWDR5) expression in embryonic stem cells. Cardiac lineage cells are derived from mesoderm and are detected by the appearance of areas of contracting cells that display characteristics of cardiomyocytes (Boheler et al., Circ. Res. 91: 189-201, (2002)). All of the cardiac cell types have been generated from differentiating organoids, and gene expression analyses suggest that their development in culture recapitulates cardiogenesis in the early embryo (Maltsev et al., Mech. Dev. 44: 41-50 (1993); Sachinidis et al., Herz 27: 589-597 (2002)).

Any means for identifying cardiac lineage cells are included in the methods of the disclosure. In some embodiments, cardiac lineage cells are identified by detecting the expression of markers for cardiomyocyte-specific proteins including, but not limited to, alpha and beta-isoforms of myosin heavy chain (aMHC/Myc6 and βMHC/Myh7), myocardin (Myocd). In some embodiments, cardiac lineage cells are identified by visible contractility of the cells.

In exemplary aspects, the following protocols are used to identify cardiac lineage cells. Day 9 organoids are harvested and fixed with 4% paraformaldehyde at 4° C. overnight. Organoids are sent to ULAM at the University of Michigan for paraffin processing, embedding, and sectioning. Antigen unmasking on slides is carried out using citric acid methods as prescribed previously (Gage et al, Hum Mol Genet. 2005; 14: 3347-3359). Immuostaining is performed by combining of VECTASTAIN® ABC-HRP kit (Vector Laboratories) and TSA™ Kit #24, with HRP-Streptavidin and Alexa Fluor 568 Tyramide (ThermoFisher Scientific). The primary antibodies used for detecting mesodermal lineage cells, as described herein, also are used, for example, as follows: anti-N-cadherin (mouse/monoclonal/1:2000, BD), anti-cardiac troponin T (CT3 clone, mouse/monoclonal/1:100, Developmental Studies Hybridoma Bank), anti-myosin heavy chain antibody (MF20 clone, mouse/monoclonal/1:100, Developmental Studies Hybridoma Bank), and brachyury/T (R&D Systems). Counter nuclear staining is performed with DAPI (Molecular Probes). Control sections are incubated without primary antibodies. Four representative pictures from different fields are taken and recorded under a fluorescence microscope (Olympus DP73).

Retinal Lineage Cells

The production of retinal lineage cells (RLCs) is important in the treatment of various forms of retinal degenerative disease. Retinal degenerative diseases, such as age-related macular degeneration (AMD) and retinitis pimentosa (RP), present an urgent need to develop strategies for retinal cell survival, repair and replacement for these and other retinal disorders. In some aspects, the generation of photoreceptors and retinal pigmented epithelium (RPE) involves the formation of organoids as a first step in the neuroectodermal differentiation process, followed by plating of the suspended organoids to a coated surface. Thereafter, adherent pigmented RPE patches appear over time and are dissected away from unwanted cell types.

In exemplary aspects, the following protocol is used to identify retinal lineage cells. Rx:GFP K/I EB5 mouse ESCs, a subline of mouse embryonic stem cell line, EB5 (129/Ola), in which GFP gene is knocked-in under Rax gene promoter, is obtained from RIKEN Cell Bank (Ibaraki, Japan). Rx:GFP ESCs are maintained in ES media [GMEM supplemented with 2.5 glutamine (Gibco), 10% knockout serum replacement, KSR (Gibco), 1% ES qualified fetal calf serum (FCS), 1 mM sodium pyruvate (Sigma), 0.1 mM non-essential amino acid (Sigma) and 0.1 mM of 2-mercaptoethnal (Sigma)]. Retinal lineage cells (RLC or RPC) are induced to differentiation via 3D organoids using methods as described previously. Briefly, 5,000 cells are re-suspended in 100 μl of GMEM-based differentiation media supplemented with 5% KSR, 1 mM sodium pyruvate, 0.1 mM non-essential amino acid and 0.1 mM of 2-mercaptoethnal and 0.1 μM of retinoic acid receptor antagonist AGN 193109 Sodium Salt (AGN, Santa Cruz), and cells are seeded on each well of a 96U ultralow attachment plate (ThermoFisher Scientific) on day 0. On day 1, 50 μl of 2% Matrigel solution (v/v, Corning) was added to embryonic body (EB) suspension. Retinal lineage cell differentiation is sustained in 96U plate for 6 to 9 days and differentiation efficiency is monitored by GFP via fluorescent microscopy (OLYPUS IX73) and flow cytometry (BD LSR II). For differentiation of ESCs using serum-free culture of embryoid-body-like aggregate (SFEB) method, 5,000 cells are re-suspended in 150 μl of GMEM-based differentiation media with 10% KSR as described elsewhere (Kamiya D, et al. Nature, 2011, 470: 503-509).

Mixed Lineage Cells

In some embodiments, the disclosure includes the production of organoids comprising a combination of mesodermal lineage cells and retinal lineage cells in a single organoid. Such mixed lineage organoids are produced, in various aspects, when ESCs are transfected with a recombinant mutant WDR5 gene with a point mutation in the conserved amino acid sequence.

Cell Culture

The serum and the exogenous cytokines conventionally required to generate ESC-derived cardiomyocytes significantly increase the costs of generating these cells for drug screening, disease modeling, diagnostic and therapeutic purposes. Reagents such as fetal bovine serum are not only expensive but its composition remains undefined and variable, and cannot be scaled for clinical use. For these reasons, strategies to reduce or exclude the use of these reagents, such as our serum-free or exogenous BMP4-free, VEGF-free, Activin A-free and/or Wnt-free method, in conjunction with small molecules that modulate WDR5 activity enjoy several advantages. Thus, the claimed methods are less variable and less expensive, and more amenable to GMP approaches, than current approaches to generate ESC-derived cardiomyocytes (Assawachananont et al., 2014; Bruce et al., 2007; Odho et al., 2010; Thomas et al., 2015a; Thomas et al., 2015b).

In exemplary aspects of the disclosure, 5,000 ESCs are re-suspended in 100 μl of GMEM based differentiation media supplemented with 5% KSR, 1 mM sodium pyruvate, 0.1 mM non-essential amino acid and 0.1 mM of 2-mercaptoethanol and 0.1 μM of retinoic acid receptor antagonist AGN 193109 Sodium Salt (AGN, Santa Cruz) and seeded on each well of 96U ultralow attachment plate (ThermoFisher Scientific) on day 0. On day 1, 50 μl of 2% Matrigel solution (v/v, Corning) is added to organoid/embryonic body (EB) suspension. Retinal lineage cell differentiation is induced in 96U plate for 6 to 9 days and differentiation efficiency was monitored by GFP via fluorescent microscopy (OLYPUS IX73) and flow cytometry (BD LSR II). For secondary hematopoietic cell differentiation, day 6 or 9 organoids are re-suspended and trypsinized to single cell suspension. 1×10^5 cells are seeded to methylcellulose based semisolid media M3234 (Stem Cell Technologies) in the presence of IL-3 (10 ng/ml), SCF (10 ng/ml) and GM-CSF (10 ng/ml). After 9 days of differentiation, resultant colony forming units (CFU) are counted under microscope (OLYMPUS IX73).

As used herein, the term "culturing" refers to the in vitro maintenance, differentiation, growth, proliferation and/or propagation of cells under suitable conditions in a medium. The term "expression" includes any step involved in the production of a recombinant protein in a cell including, but not limited to, transcription, post-transcriptional modification, translation, post-translational modification, and secretion.

Wild Type (WT) Culture Conditions

Rx:GFP K/I EB5 mouse ESCs, a subline of the mouse embryonic stem cell line, EB5 (129/Ola), in which GFP gene is knocked-in under Rax gene promoter, is obtained from RIKEN Cell Bank (Ibaraki, Japan). Rx:GFP ESCs are maintained in ES media [GMEM supplemented with 2.5 glutamine (Gibco), 10% knockout serum replacement, KSR (Gibco), 1% ES qualified fetal calf serum (FCS), 1 mM sodium pyruvate (Sigma), 0.1 mM non-essential amino acid (Sigma) and 0.1 mM of 2-mercaptoethnal (Sigma)]. ESCs are induced to differentiate into retinal progenitor cells (RPC) via 3D organoid methods as described previously. Briefly, 5,000 cells are re-suspended in 100 μl of GMEM based differentiation media supplemented with 5% KSR, 1 mM sodium pyruvate, 0.1 mM non-essential amino acid and 0.1 mM of 2-mercaptoethnal and 0.1 μM of retinoic acid receptor antagonist AGN 193109 Sodium Salt (AGN, Santa Cruz) and seeded on each well of 96U ultralow attachment plate (ThermoFisher Scientific) on day 0. On day 1, 50 μl of 2% Matrigel solution (v/v, Corning) is added to embryoid body (EB) cell suspension. Retinal progenitor cell differentiation is sustained in 96U plate for 6 to 9 days and differentiation efficiency is monitored by GFP via fluorescent microscopy (OLYPUS IX73) and flow cytometry (BD LSR II). For differentiation of ESCs using the serum-free culture of embryoid-body-like aggregate (SFEB) method, 5,000 cells are re-suspended in 150 μl of GMEM-based differentiation media with 10% KSR as described by Kamiya et al. (Nature, 2011, 470: 503-509).

Fetal Bovine Serum-Containing Culture Conditions

For spontaneous ESC differentiation, 5,000 cells are re-suspended in 150 μl of GMEM-based differentiation media with 10% fetal calf serum.

T12h Conditions

T12h conditions are similar to wild-type culture conditions, with the exception that Dox is added at 12 h after differentiation, i.e., at 12 hours after Dox is first removed from the hWDR5$^{Dox}$;mWdr5$^{KO}$ ESCs.

T36h Conditions

T36h conditions are similar to wild-type culture conditions, with the exception that Dox is added at 36 h after differentiation, i.e., at 36 hours after Dox is first removed from the hWDR5$^{Dox}$;mWdr5$^{KO}$ ESCs.

T48h Conditions

T48h conditions are similar to wild-type culture conditions, with the exception that Dox is added at 48 h after differentiation, i.e., at 48 hours after Dox is first removed from the hWDR5$^{Dox}$;mWdr5$^{KO}$ ESCs.

Retinal Culture Conditions

Retinal culture conditions are the same as those described herein-above as wild type (WT) culture conditions.

Hematopoietic Culture Conditions 5,000 ESCs are seeded in 5% knockout serum replacement containing media in low attachment 96 well plates (day 0). At day 1, matrigel is added to the 96 well plates. At 36 to 48 hours post differentiation, Dox (2 ug/ml) is added to 96 well plates to induce recombinant hWDR5 expression. At EB day 6 or day 9, organoids are resuspended in single cell solution and seeded to a commercially available secondary hematopoietic cell differentiation colony forming unit assay. For secondary hematopoietic cell differentiation (after mesodermal differentiation), day 6 or 9 organoids are re-suspended and trypsinized to single cell suspensions. 1×10^5 cells are seeded to methylcellulose-based semisolid media M3234 (Stem Cell Technologies) in the presence of IL-3 (10 ng/ml), SCF (10 ng/ml), and GM-CSF (10 ng/ml). After 9 days of differentiation, resultant colony forming units (CFU) are counted under microscope (OLYPUS IX73).

Neuroectoderm-Permissive Culture Conditions

Neuroectoderm-permissive culture conditions are the same as those described herein-above as wild type (WT) culture conditions.

Suspension Culture

In various aspects, the cells are cultured in suspension. Any means known for culturing cells in suspension are included in the disclosure. In exemplary aspects, suspension culture conditions are the same as those described herein, and as described in more detail in the Examples and figure legends provided herein.

Monolayer Culture

In various aspects, the cells are cultured in monolayers. Any means known for culturing cells in monolayer are included in the disclosure. In some aspects, 1000 cells/cm$^2$ are plated on gelatin-coated culture dishes. At day 0, ESC medium is replaced by knockout serum replacement (KSR) medium: knockout Dulbecco's modified Eagle's medium (Gibco) supplemented with 15% KSR (Invitrogen, Life Technologies, Carlsbad, CA), 2 mM L-glutamine, 100 U/mL penicillin/streptomycin (Lonza), and 0.1 mM beta-mercaptoethanol (Sigma-Aldrich). Medium is replaced every two days until day 13.

Methods of Screening

Any methods for screening known in the art are included for use in the methods of the disclosure. Example 1 discusses some of the screening methods used in exemplary aspects of the disclosure.

Kits

In some embodiments, the disclosure includes kits which comprise the cells made according to the methods described herein. In some embodiments, the disclosure includes kits which comprise reagents for practicing the methods described herein. In some aspects, the cells are packaged in a manner which facilitates their use for research or for administration to a subject.

In one embodiment, such a kit includes cells in a diluent or medium packaged in a container such as a sealed bottle or vessel, with a label affixed to the container or included in the package that describes use of the cells. In one embodiment, the medium comprising the cells is in a container such that the amount of headspace in the container (e.g., the amount of air between the liquid formulation and the top of the container) is very small. Preferably, the amount of headspace is negligible (i.e., almost none).

In some aspects, the formulation comprises a stabilizer. The term "stabilizer" refers to a substance or excipient which protects the formulation from adverse conditions, such as those which occur during heating or freezing, and/or prolongs the stability or shelf-life of the formulation in a stable state. Examples of stabilizers include, but are not limited to, sugars, such as sucrose, lactose and mannose; sugar alcohols, such as mannitol; amino acids, such as glycine or glutamic acid; and proteins, such as human serum albumin or gelatin.

In some aspects, the formulation comprises an antimicrobial preservative. The term "antimicrobial preservative" refers to any substance which is added to the composition that inhibits the growth of microorganisms that may be introduced upon repeated puncture of the vial or container being used. Examples of antimicrobial preservatives include, but are not limited to, substances such as thimerosal, 2-phenoxyethanol, benzethonium chloride, and phenol.

In some aspects, the kit contains a label that describes use of the reagents provided in the kit. In some aspects, the label includes instruction for use.

This entire document is intended to be related as a unified disclosure, and it should be understood that all combinations of features described herein are contemplated, even if the combination of features are not found together in the same sentence, or paragraph, or section of this document. The disclosure also includes, for instance, all embodiments of the disclosure narrower in scope in any way than the variations specifically mentioned above. With respect to aspects of the disclosure described as a genus, all individual species are considered separate aspects of the disclosure. With respect to aspects of the disclosure described or claimed with "a" or "an," it should be understood that these terms mean "one or more" unless context unambiguously requires a more restricted meaning. If aspects of the disclosure are described as "comprising" a feature, embodiments also are contemplated "consisting of" or "consisting essentially of" the feature.

All publications, patents and patent applications cited in this specification are herein incorporated by reference as if each individual publication or patent application were specifically and individually indicated to be incorporated by reference in its entirety to the extent that it is not inconsistent with the disclosure.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Additional aspects and details of the disclosure will be apparent from the following examples, which are intended to be illustrative rather than limiting.

Example 1—Material and Methods

Material and methods used in various aspects of the disclosure are described herein in Example 1.

ESC Maintenance and Induced Differentiation

Rx:GFP K/I EB5 mouse ESCs, a subline of mouse embryonic stem cell line, EB5 (129/Ola), in which green fluorescent reporter (GFP) gene is knocked-in under Rx/Rax gene promoter, was ordered from RIKEN Cell Bank (Ibaraki, Japan). Rx:GFP ESCs were maintained in ESC media [GMEM supplemented with 2.5 glutamine (Gibco), 10% knockout serum replacement, KSR (Gibco), 1% ES qualified fetal calf serum (FCS), 1 mM sodium pyruvate (Sigma), 0.1 mM non-essential amino acid (Sigma) and 0.1 mM of 2-mercaptoethnal (Sigma)]. Induced differentiation to retinal progenitor cells (RPC) via 3D organoid culture was performed as described previously. Briefly, 5,000 cells were re-suspended in 100 µl of GMEM based differentiation media supplemented with 5% KSR, 1 mM sodium pyruvate, 0.1 mM non-essential amino acid and 0.1 mM of 2-mercaptoethnal and 0.1 µM of retinoic acid receptor antagonist AGN 193109 Sodium Salt (AGN, Santa Cruz) and seeded on each well of 96U ultralow attachment plate (ThermoFisher Scientific) on day 0. On day 1, 50 µl of 2% Matrigel solution (v/v, Corning) was added to embryonic body (EB) suspension. Retinal progenitor cell differentiation was induced in 96U plate for 6 to 9 days and differentiation efficiency was monitored by GFP via fluorescent microscopy (OLYMPUS IX73) and flow cytometry (BD LSR II). For differentiation of ESCs using serum-free culture of embryoid-body-like aggregate (SFEB) method, 5,000 cells were re-suspended in 150 µl of GMEM based differentiation media with 10% KSR as described elsewhere (Kamiya D, et al. Nature, 2011, 470: 503-509). For spontaneous ES differentiation, 5,000 cells were re-suspended in 150 µl of GMEM based differentiation media with 10% FCS. For secondary hematopoietic cell differentiation, day 6 or 9 organoids were re-suspended and tripsinized to single cell suspension. 1×10^5 cells were seeded to methylcellulose based semisolid media M3234 (Stem Cell Technologies) in the presence of IL-3 (10 ng/ml), SCF (10 ng/ml) and GM-CSF (10 ng/ml). After 9 days of differentiation, resultant colony forming units (CFU) were counted under microscope (OLYMPUS IX73).

Plasmids and ESC transfection

Doxcycline (Dox) inducible PiggyBac plasmids including pPBhCMV1cHApA, pPBCAG-rtTM2-IN and transposase were kindly provided by Dr. Hitoshi Niwa (Kumamoto University, Japan). Full-length human wild type WDR5 was cloned to pPBhCMV1cHApA plasmid. Flag-tagged wild type or mutant forms of WDR5 (F133Y, N225A, L240K, V268E, Q289E and I305V) were sub-cloned into non-inducible piggyBac plasmid (Addgene, #48754). For mESC transfection, 20 µg endotoxins free plasmid DNA was electroporated to 5×10^6 ESCs using mouse ES cell NUCLEOFECTOR® kit (Lonza). Antibiotic resistant ESC colonies were selected for 5 days and pooled; in addition single cell derived clones were selected for further characterization. To generate CRISPR-Cas9 mediated mWDR5 knockout (KO) plasmid, mWdr5 guide RNA sequence (TGT-GAAGTTCAGCCCCAATG; SEQ ID NO: 16) was cloned into pSpCas9(BB)-2A-Puro (PX459) V2.0 plasmid (Addgene, #62988). To generate mWdr5 KO ESC clones harboring with inducible exogenous hWDR5 rescue platform (hWDR5Dox;mWdr5KO ESC lines), Dox inducible hWDR5 pooled ESC population were subjected to 2nd round of transfection with mWdr5 KO plasmid and selected with puromycin (2 µg/ml) in the presence of Dox (2 µg/ml). Single cell-derived ES clones were picked up, expanded and maintained in presence of Dox. Sanger sequencing was used to determine DNA editing at expected sites and homozygous Indel mutations causing frameshifts were selected as hWDR5Dox;mWdr5KO ESC clones.

Alkaline Phosphatase (AP) Staining and Giemsa Staining

A blasticidin resistance gene was inserted into one of the endogenous Oct4 alleles in the parental EB5 ESC lines from which Rx:GFP ESCs were derived. The undifferentiated status of Rx:GFP ESCs were assessed by AP staining using alkaline phosphatase staining kit II (STEMGENT) following Oct4 (+) colony selection after treatment with blasticidin. For blasticidin selection (20 µg/ml), ESCs were seeded in clonal density (500 to 1,000 cells in 10 ml ESC media in 10 cm dish) and cultured for 5 days. Blasticidin resistant ESC colonies were fixed with 100% methanol and stained with 4% Giemsa buffer in order to count colony number.

RNA Isolation, Reverse Transcription and Quantitative Real-Time PCR (RT-qPCR)

Trizol reagent (ThermoFisher Scientific) and RNeasy mini kit (Qiagen) were utilized for RNA isolation from ESCs or EBs. 1.0 µg total RNA was reverse transcribed to cDNA using high-capacity RNA-to-cDNA™ kit (ThermoFisher Scientific). RT-qPCR was performed using iQ SYBR green supermix (Bio-Rad). Gapdh or β-actin was used as internal control for normalization. Primer sequences for real-time PCR were available upon request. Data were automatically analyzed using Bio-Rad CFX manager software using Δ/ΔCt method.

In various aspects of the disclosure, quantitative reverse transcription PCR (RT-qPCR) is used to analyze results obtained in the examples. Table 1 set out below provides various primer sequences used to screen for the expression of various genes used in identifying cell lineages. In some aspects, RT-qPCR is carried out using iQ SYBR green supermix (Bio-Rad). Gapdh or β-actin was used as an internal control for normalization. Primer sequences used for RT-qPCR are provided in the Table 1 below. Data is automatically analyzed using Bio-Rad CFX manager software using Δ/ΔCt method.

TABLE 1

RT-qPCR primer sequences

| | | | |
|---|---|---|---|
| A-MHC | SEQ ID NO: 17 gcccagtacctccgaaagtc | SEQ ID NO: 18 | gccttaacatactcctccttgtc |
| B-MHC | SEQ ID NO: 19 acaaccctacgattatgcgt | SEQ ID NO: 20 | acgtcaaaggcactatccgtg |
| TROPONIN T | SEQ ID NO: 21 ggcagaaccgcctggctgaa | SEQ ID NO: 22 | ctgccacagctccttggcct |
| MEF2C | SEQ ID NO: 23 ctgagcgtgctgtgcgactgt | SEQ ID NO: 24 | gctctcgtgcggctcgttgta |
| MYOCD | SEQ ID NO: 25 cgccactgaaaggtccaact | SEQ ID NO: 26 | gtggaggcttggagaatgtg |
| RAX | SEQ ID NO: 27 cgacgttcaccacttaccaa | SEQ ID NO: 28 | tcggttctggaaccatacct |

TABLE 1-continued

RT-qPCR primer sequences

| | | | | | |
|---|---|---|---|---|---|
| SIX3 | SEQ ID NO: 29 | ccggaagagttgtccatgttc | SEQ ID NO: 30 | cgactcgtgtttgttgatggc |
| NCAD | SEQ ID NO: 31 | cagggtggacgtcattgtag | SEQ ID NO: 32 | agggtctccaccactgattc |
| OCT4 | SEQ ID NO: 33 | gtggaggaagccgacaacaatga | SEQ ID NO: 34 | caaaagaccctgagacgatg |
| ACTIN | SEQ ID NO: 35 | accaactgggacgacatggagaag | SEQ ID NO: 36 | caagctgattggcgatgtgag |
| FOXA2 | SEQ ID NO: 37 | ggcccagtcacgaacaaagc | SEQ ID NO: 38 | ttctcatcagccagaacacct |
| GATA4 | SEQ ID NO: 39 | ttcctgctcggacttgggac | SEQ ID NO: 40 | gcagccaatcatagcagacttgcgt |
| GATA6 | SEQ ID NO: 41 | acagcccacttctgtgttccc | SEQ ID NO: 42 | cttctgtttccgatcagctcccttg |
| NANOG | SEQ ID NO: 43 | tggtccccacagtttgcctagttc | SEQ ID NO: 44 | ggtcgtttgaaccaagtccctc |
| SOX2 | SEQ ID NO: 45 | caggagaacccaagatgcacaa | SEQ ID NO: 46 | attaagctcctgggtcgcaag |
| T | SEQ ID NO: 47 | ctctaatgtcctcccttgttgcc | SEQ ID NO: 48 | ttcccaggcaggtggagaataag |

Whole Cell Lysate Preparation, Histone Extraction and Western Blotting

ESCs or EBs were lysed with RIPA buffer (Pierce) in the presence of EDTA free protease inhibitor cocktail (Sigma). Histone extraction on EBs was performed using a histone extraction kit (Abcam) as described previously (Khan M, et al. 2015). Protein concentration was determined using Pierce BCA protein assay kit (ThermoFisher Scientific). 1.0 μg of histone extracts or 10 μg of whole cell lysate was resolved on 4-20% precast gel (Bio-Rad) and SDS-PAGE gel was transferred to 0.45 μm PVDF membrane (Millipore). The following primary antibodies were used for probing: anti-HA (1:10,000, Abcam, ab9110), anti-WDR5 (1:5000, R&D), anti-WDR5 (1:5,000, Bethyl), anti-Flag (1:2,000, Sigma), anti-H3 (1:10,000, Abcam), anti-H3K4Me1 (1:5000, Millipore), anti-H3K4Me2 (1:10,000, Millipore), anti-H3K4Me3 (1,10,000, Abcam), anti-Tubulin (1:10,000, Cell signaling), anti-β-Actin (1:10,000, Cell signaling).

Immunohistochemistry

Day 9 EBs were harvested and fixed with 4% paraformaldehyde at 4 degree overnight. Harvested EBs underwent paraffin processing, embedding and sectioning. Antigen unmasking on slides was using citric acid methods as prescribed previously (Gage P, et al, Hum Mol Genet. 2005; 14: 3347-3359.). Immuostaining were performed by combining of VectaStain ABC-HRP kit (Vector laboratories) and TSA™ Kit #24, with HRP-Streptavidin and Alexa Fluor 568 Tyramide (ThermoFisher Scientific). The primary antibodies were used for staining: anti-N-cadherin (mouse/monoclonal/1:2000, BD), anti-cardiac troponin T (CT3 clone, mouse/monoclonal/1:100, Developmental Studies Hybridoma Bank) and anti-myosin heavy chain antibody (MF20 clone, mouse/monoclonal/1:100, Developmental Studies Hybridoma Bank). Nuclear staining was performed with DAPI (Molecular Probes). Control sections were incubated without primary antibodies. 4 representative pictures from different field were recorded under fluorescence microscope (Olympus DP73).

Flow Cytometry 2 to 4 organoids were combined and dissociated to single cell suspension by 0.25% trypsin-EDTA (Invitrogen). DMEM media with 10% FBS (Sigma, v/v) was used to inactivate trypsin and cells were subjected to spin down at 300 g for 5 min. The resulting cell pellet was washed once using D-PBS without calcium and magnesium and re-suspended in 200 μl of D-PBS in V-bottom plate. Cells were immediately transferred to LSR-II flow cytometer (BD) for data recording and analysis. The dead cells in the cell population were gated out and percentage of GFP (+) cells were calculated based on live cell content.

RNA-Seq

RNA isolation for RNA-Seq was performed by combination of Trizol reagent (ThermoFisher Scientific) and RNeasy mini kit (Qiagen). Day 6 EB RNA samples [WT group, mWdr5 KO #3 with early induction (Dox added at 12 h after differentiation, T12h group) and late induction (Dox added at 48 h after differentiation, T48h group) of hWdr5] were sent to University of Michigan DNA Sequencing Core for RNA quality analysis, library construction and sequencing using Illumine HiSeq Libraries platform. Duplicate samples for each group were subjected to two round of independent library preparation and sequencing to avoid sample and batch effect of RNA-Seq.

ChIP-Seq

Chromatin Immunoprecipitation (ChIP) was performed using a slightly modified version of ChIP Assay Kit (Millipore) based protocol as described previously. Day 6 EBs [mWdr5 KO #3 with early induction (Dox added at 12 h after differentiation, T12 group, total cell number $3 \times 10^{7}$) and late induction (Dox added at 48 h after differentiation, T48 group, total cell number $4 \times 10^{7}$) of hWDR5 were fixed with Disuccinimidyl glutarate crosslinker (COVAChem) at final concentration of 2 μM at room temperate for 30 min. Cells were further subjected to crosslink with 1% paraformaldehyde (Sigma) at room temperature at 10 min and the reaction was quenched using glycine at final concentration of 0.125M. The cell pellets were further sonicated to 300-500 bp in SDS lysis buffer by using a Biorupter 300 (Diagenode). 15 μg ChIP grade anti-HA antibody (ab9110, Abcam) was used for ChIP assay. The ChIP-DNA were sent to University of Michigan DNA Sequencing Core for quality control, library preparation and sequencing using Illumina HiSeq Library platform.

Statistical Analysis

All experiments were performed using two or more independently gene edited hWDR5$^{Dox}$;mWdr5$^{KO}$ ESC clonal lines (biological replicates), and repeated at least for two to four times with similar results, and data from one representative experiment are presented unless otherwise stated. Two-sided unpaired Student's t-test was applied using GraphPad Prism (version 7.00) to determine whether the observed differences were statistically significant. Changes were considered statistically significant when p value less than 0.05.

Bioinformatics Analysis

Reads Mapping and Coverage

All RNA-Seq data were mapped to the mm10 genome for mouse, and hg38 genome for human, using Tophat2 (2.1.1) [1], which was shown to be accurate alignment of transcriptomes in the presence of insertions, deletions and gene fusions. Then, duplicated reads for pair-end data were removed, but not single-end data by SAMtools (v1.5) [2]. All ChIP-Seq data were mapped to the mm10 genome for mouse by using Bowtie2 (v2-2.2.4) [3], an ultrafast and memory-efficient tool for aligning sequencing reads to long reference sequences. Then, we removed any duplicated reads for both pair-end and single-end data using SAMtools (v1.5) [2]. For all sequencing datasets, the bigwig files for visualization in Integrative Genomics Viewer (IGV) [4] were generated from BAM files by using "bamCoverage" from deepTools [5] with parameters "—ignoreDuplicates—normalizeUsingRPKM—skipNonCoveredRegions—binSize 50".

Peak Calling and Annotation

BAM files of mapping results were merged for the same sample using SAMtools and converted to BED format by using BEDTools [6]. Peaks of regulatory regions were called for each sample by using MACS (v 1.4.2) [7] from datasets of ChIP-Seq with parameters "-w -S -p 0.00001". The input signal was used as the control to call peaks for the ChIP-Seq dataset. The heatmap plot of signals centered on peaks and gene promoters was implicated by deepTools2 (v2.5.0) [8]. Peak annotation was performed by using HOMER (v4.9.1) [9] with default parameters. Motif analysis on peak regions was performed with HOMER function findMotifsGenome.pl with parameters "-size 50-mask".

Example 2—Acute Loss of WDR5 Impairs mESC Viability and Self-Renewal

Previous studies have reported that acute, short hairpin RNA (shRNA)-mediated knockdown of WDR5 in mESCs cultured in serum and leukemia inhibitory factor (LIF) leads to impaired mESC self-renewal without affecting cell apoptosis (Ang et al., 2011). Yet the role of the epigenetic regulator WDR5 in lineage specification, especially during mammalian retinal differentiation, remained elusive. To dissect the molecular function of WDR5 during retinal development, a knockin reporter line, Rx-GFP mESCs, which generate 60-80% Rx-GFP+ RLCs via 3-D organoid culture in 4-7d (Assawachananont et al., 2014; Decembrini et al., 2014; Eiraku et al., 2011) was used. Compared to undifferentiated mESCs, WDR5 mRNA expression in ESC-derived Rx-GFP+ RLCs and Rx-GFP-non-RLCs decreased only modestly (FIG. 1A), suggesting that WDR5 functions in maintaining both RLC and non-RLC populations.

To overcome the requirement of WDR5 for ESC self-renewal and to address the possibility that residual WDR5 function by incomplete knockdown by shRNA may mask phenotype characterization, an ESC-based rescue complementation system was devised. In the presence of doxycycline (Dox), these Rx-GFP ESC lines express human WDR5 (hWDR5); in the absence of Dox, no WDR5/Wdr5 is produced as the endogenous murine WDR5 (mWdr5) has been knocked out via a CRISPR/Cas9 strategy. These hwDR5$^{Dox}$;mwdr5$^{KO}$ ESC lines were generated in two steps as set out herein below.

Figure 7A:
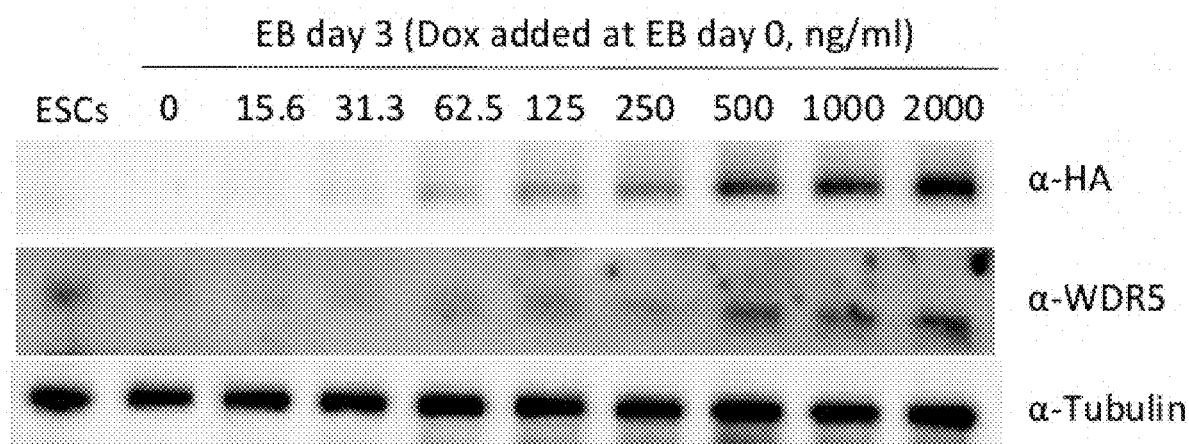
FIGS. 7A-7G. Derivation of hWDR5$^{Dox}$;mWdr5$^{KO}$ (i.e., mWdr5 KO) ESCs.
Figure 7B:
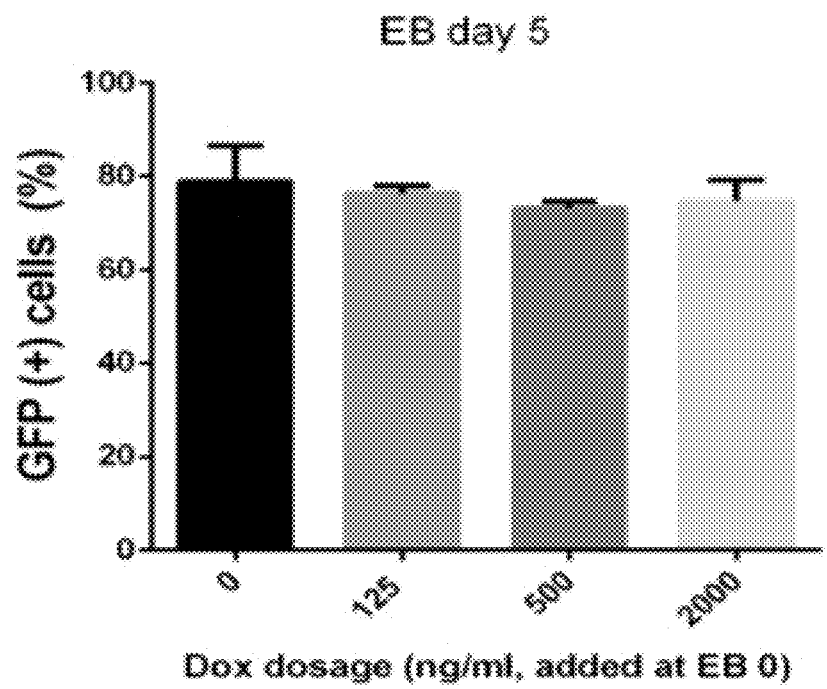

First, Rx-GFP ESCs were stably transfected with a Dox inducible Piggybac plasmid engineered to express full-length (FL) HA-tagged hWDR5Dox. FL hWDR5 shares 100% amino acid sequence homology with FL mWdr5. Indeed, HA-tagged hWDR5 was induced by Dox in a dose-dependent manner during RxGFP+ RLC organoid culture (FIG. 7A). Prior to CRISPR/Cas9-based mWdr5 gene editing, overexpression of hWDR5 did not affect RxGFP+ RLC differentiation (FIG. 7B). These data indicate that inducible hWDR5 expression, in the presence of intact, endogenous m WDR5, does not alter ESC differentiation to the retinal lineage.

Figure 1B:
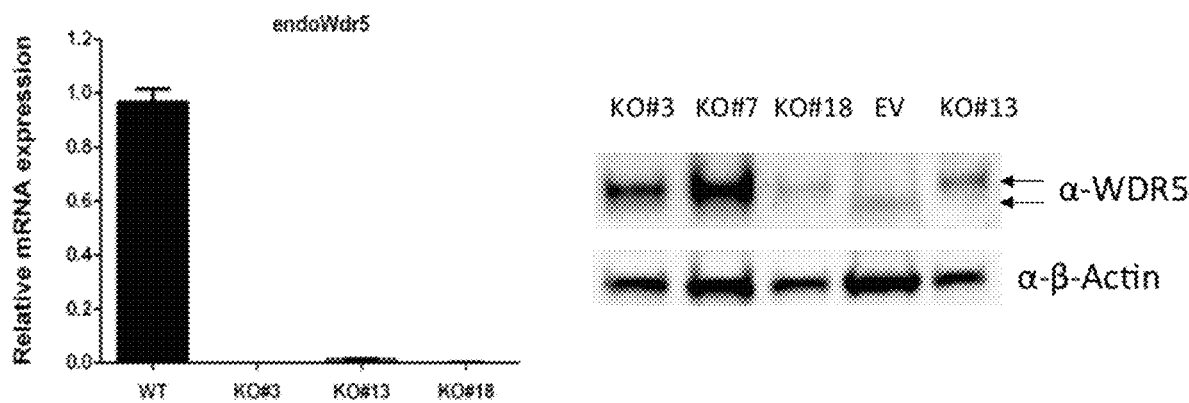
Figure 7C:
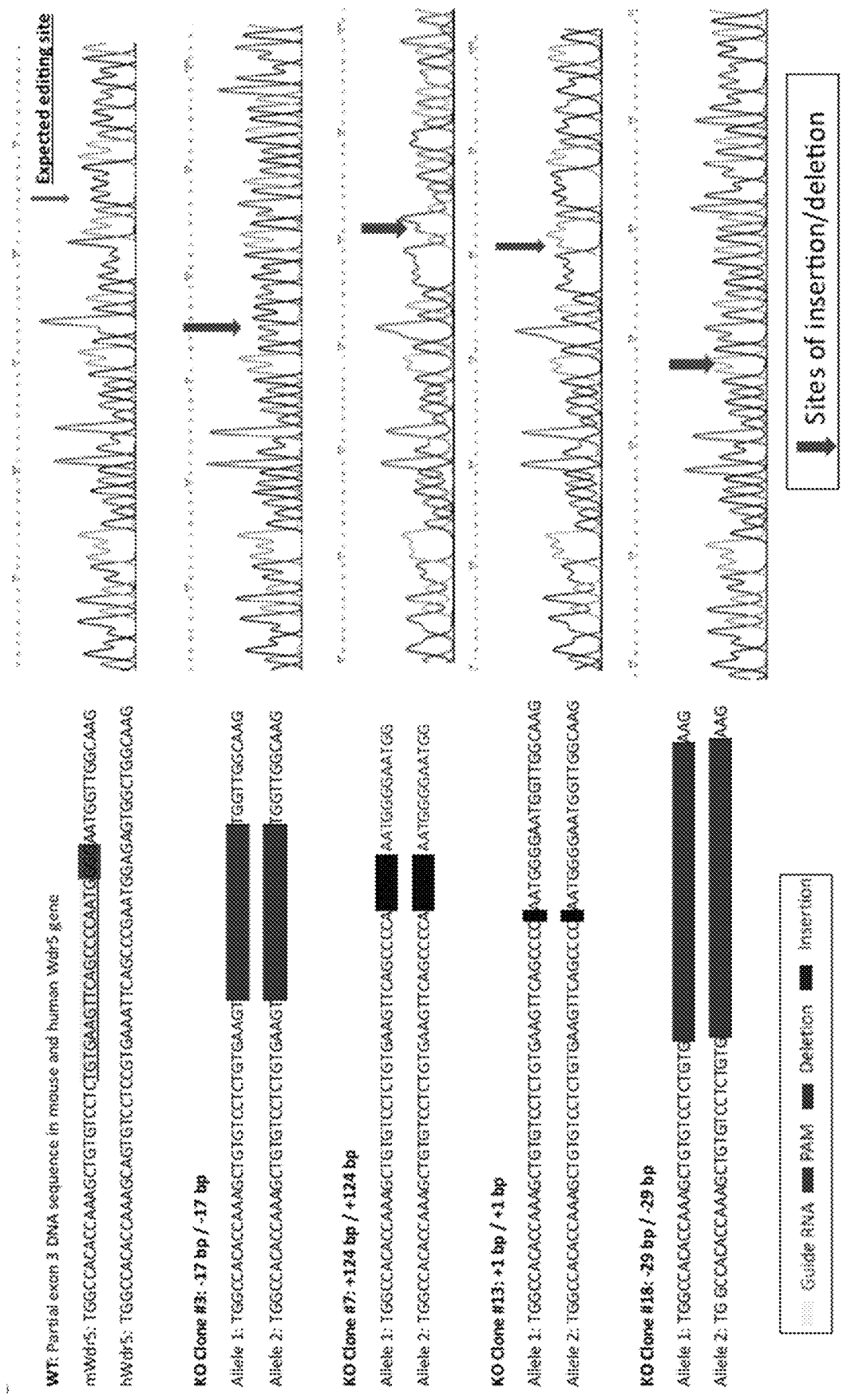
Figure 7D:
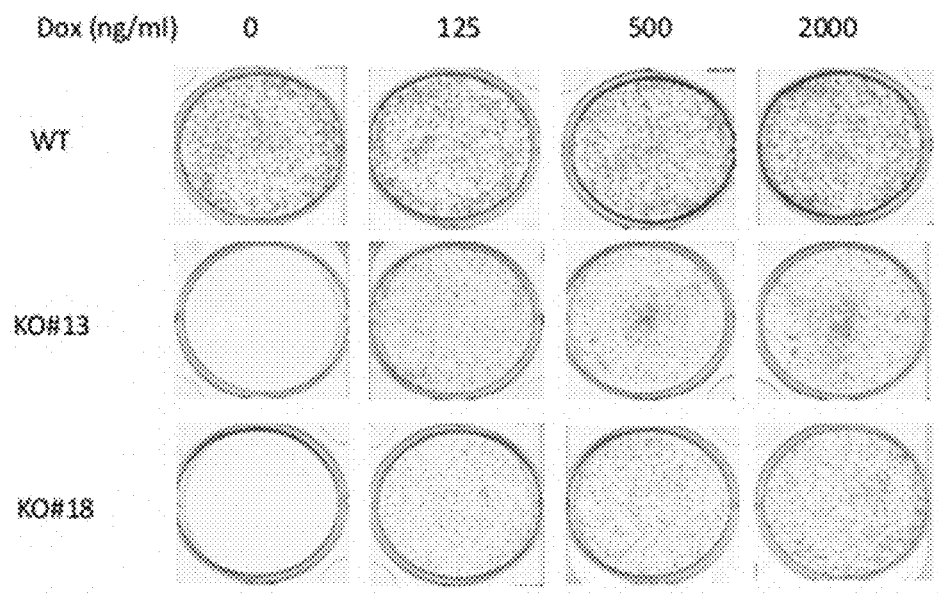

Second, a CRISPR/Cas9-based strategy to knockout (KO) endogenous mWdr5 in ESCs was used. Due to genomic DNA sequence differences between mouse and human mWdr5/hWDR5 exon 3, gRNAs edited only the endogenous m WDR5, leaving the donor HA-hWDR5 plasmid DNA intact. Following CRISPR/Cas9-mediated editing of mWDR5, hWDR5-expressing, single-cell derived ESC clones cultured with Dox were isolated and underwent Sanger sequencing to determine the type of gene editing that occurred at the mWdr5 locus. Four clones containing homozygous frameshift mutations were identified (FIG. 7C). For these Sanger sequenced, hWDR5$^{Dox}$;mWdr5$^{KO}$ ESC clones, deletion of endogenous m WDR5 was confirmed by quantitative real-time PCR and western blotting (FIG. 1B). Of the four clones, two uniquely edited hWDR5$^{Dox}$;mWdr5$^{KO}$ ESC clones (#3 and #7) expressed Dox-induced exogenous hWDR5 protein at levels higher than endogenous WDR5 protein, while two other clones (#13 and #18) induced hWDR5 protein at levels comparable to endogenous WDR5 (FIG. 1B). These four clones were used for all the experiments set out in the examples disclosed herein.

hWDR5$^{Dox}$;mWdr5$^{KO}$ ESCs cultured in Dox displayed the hallmarks of an undifferentiated state, including formation of alkaline phosphatase-positive domed colonies (FIG. 1C), and expression of core pluripotency factors Oct4 and Nanog at levels similar to wild-type (WT) controls (FIG. 1D). hWDR5Dox;mWdr5KO ESCs plated at clonal density in the absence of Dox led to a marked loss of viable ESC colonies. This loss of viable ESC colonies could be rescued by Dox treatment (FIG. 7D). These results establish that WDR5 is not only required for ESC self-renewal (Ang et al., 2011), but is also essential for cell viability.

Figure 7E:
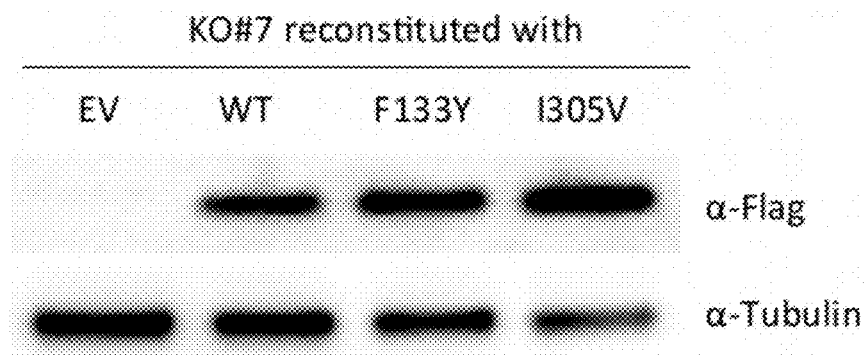
Figure 7F:
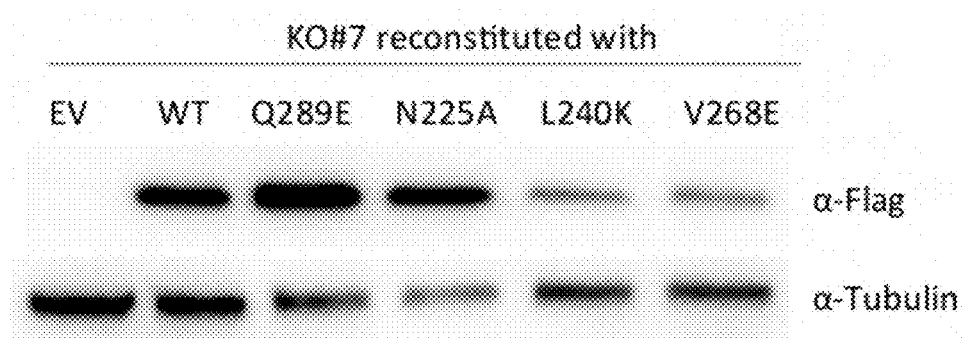
Figure 7G:
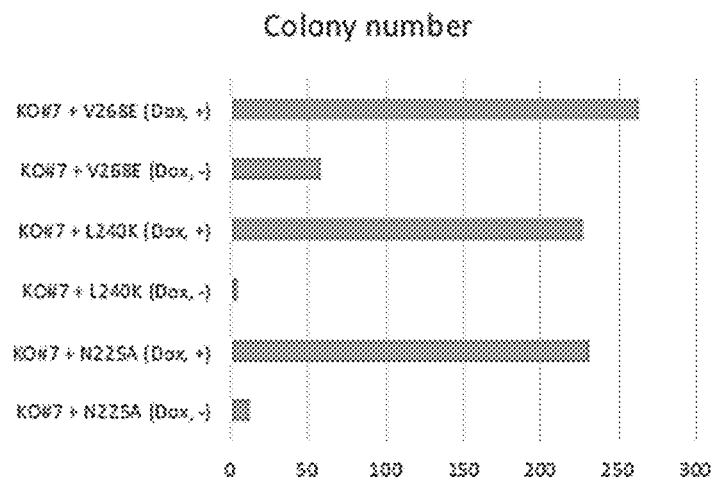

The best known function of WDR5 is to complex MLL1 and RBPP5 in order to regulate MLL1-mediated histone methyltransferase activity (Wysocka et al., 2005). To test whether MLL1 binding (via the Win motif) and RbBP5 binding surfaces of WDR5 protein are essential for ESC maintenance, WT or various mutant forms of WDR5 constructs were stably transfected into hWDR5Dox;mWdr5KO ESCs (FIG. 7E-F). Interestingly, expression of WT hWDR5 or hWDR5 with MLL win motif-binding mutants (F133Y or I305V) led to similar levels of rescue of Oct4+ ESC colonies in mWDR5 KO ESCs (FIG. 1E). When hWDR5 with RbBP5 binding surface mutants were expressed in mWdr5 KO ESCs, Oct4+ ESC colonies were observed with Q289E expression, but N225A, L240K and V268E mutant forms of hWDR5 could not maintain Oct4+ ESC colonies (FIG. 1E, FIG. 7F), even though N225A hWDR5 mutant protein is expressed at comparable levels to WT control (FIG. 7E) (Karatas et al., 2013; Patel et al., 2008; Thomas et al., 2015b). Together these data indicate that the complete loss of WDR5 results in impaired cell viability and defective self-renewal in ESCs.

Example 3—WDR5 Regulates Organoid-Based, Retinal Progenitor Cell Differentiation in a Dose- and Time-Dependent Manner Having established that WDR5 controls not only mESC self-renewal and viability, experiments were carried out to determine whether temporal fine-tuning of exogenous hWDR5 expression in mWDR5 KO ESCs could influence mESC differentiation to the retinal lineage.

Figure 2A:
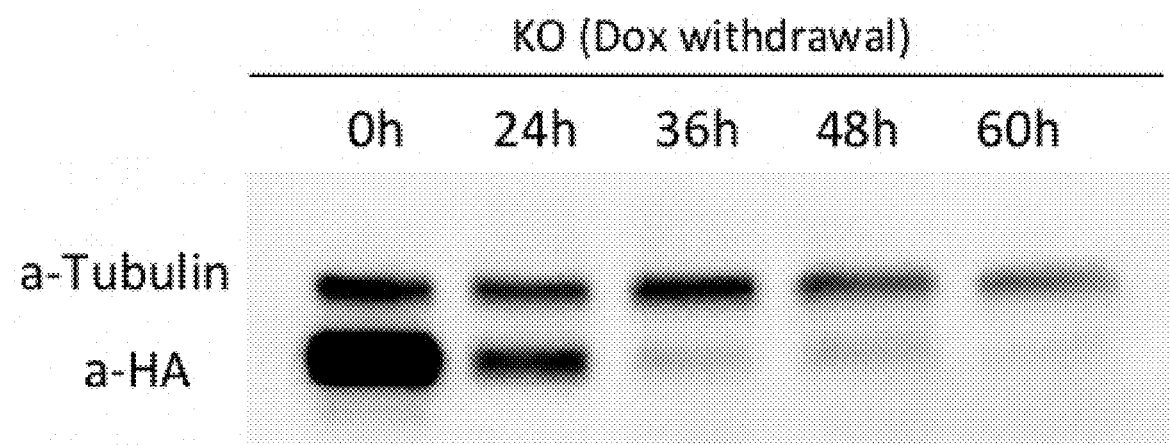
FIGS. 2A-2H. WDR5 regulates retinal progenitor cell fate transition in a dose- and time-dependent manner.

Dox removal at time 0 h (T0h), at which time dissociated ESCs are allowed to form organoids or embryoid bodies (EBs) upon RLC differentiation (Decembrini et al., 2014; Eiraku et al., 2011), led to significant reduction of HA-hWDR5 protein from T24h onwards (FIG. 2A), indicating tight control of exogenous hWDR5 in mWdr5 KO organoids in a time-dependent manner.

Figure 2B:
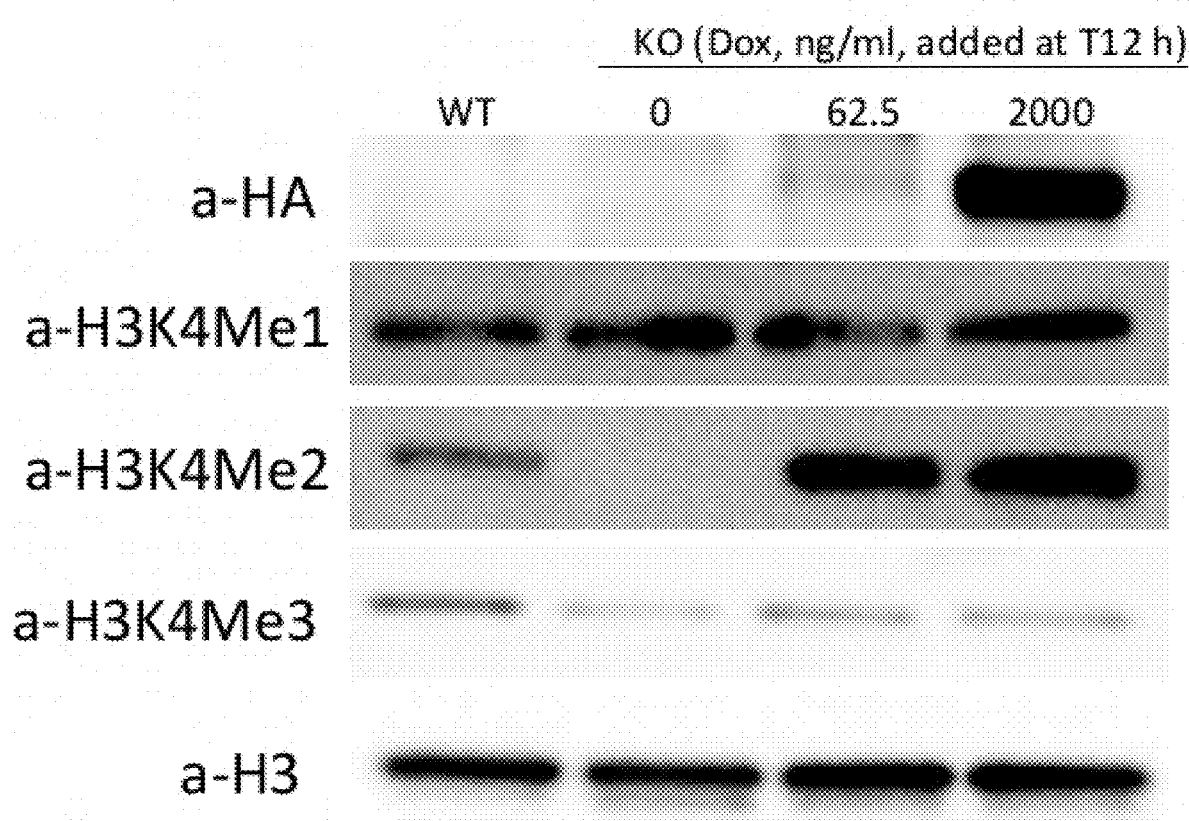

Removal of Dox during the retinal differentiation culture resulted in reduction of histone markers H3K4Me2 and H3K4Me3, but not H3K4Me1 (FIG. 2B), which is consistent with previous findings that Wdr5 regulates H3K4 modification (Ang et al., 2011). These data were further supported by induction of HA-hWDR5 by culture with Dox at 12 h after differentiation (hereafter termed as T12h), which led to increased H3K4me2 and H3K4me3 in mWdr5 KO organoids or EBs (FIG. 2B). Because WDR5 controls cell viability in undifferentiated ESCs described above, it is possible that any observed reduction in RLC differentiation from mWDR5 KO ESCs could be a secondary effect linked to cell lethality.

Figure 2C:
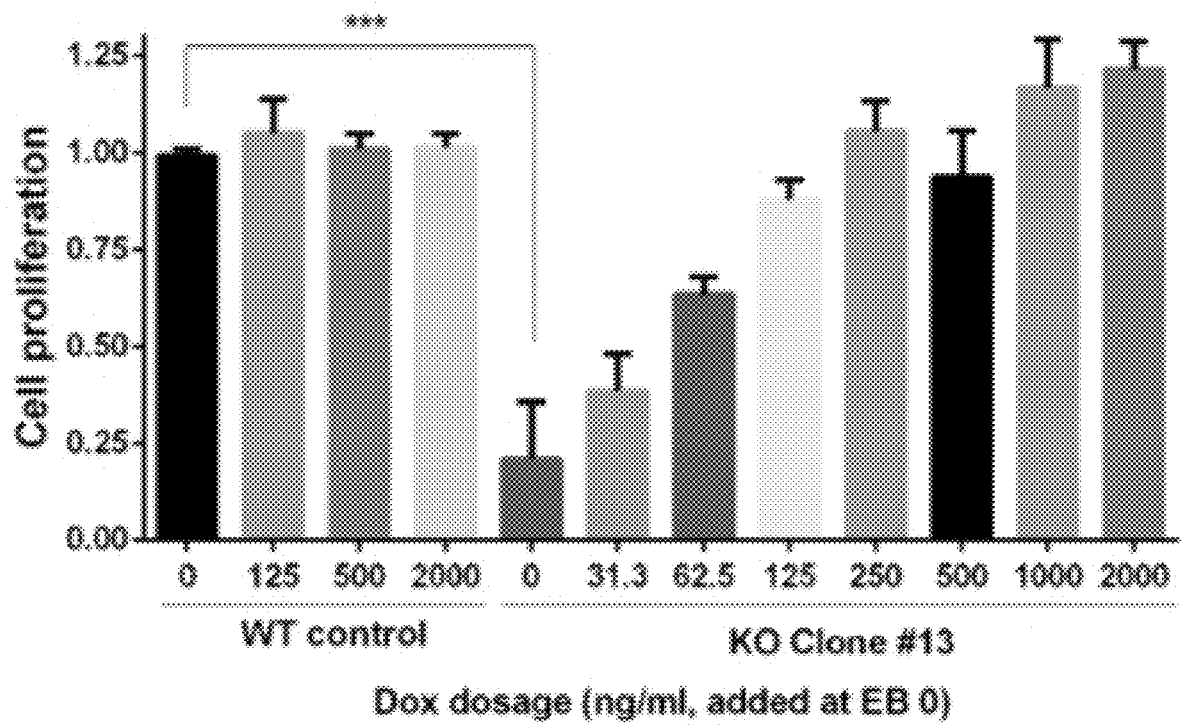
Figure 2D:
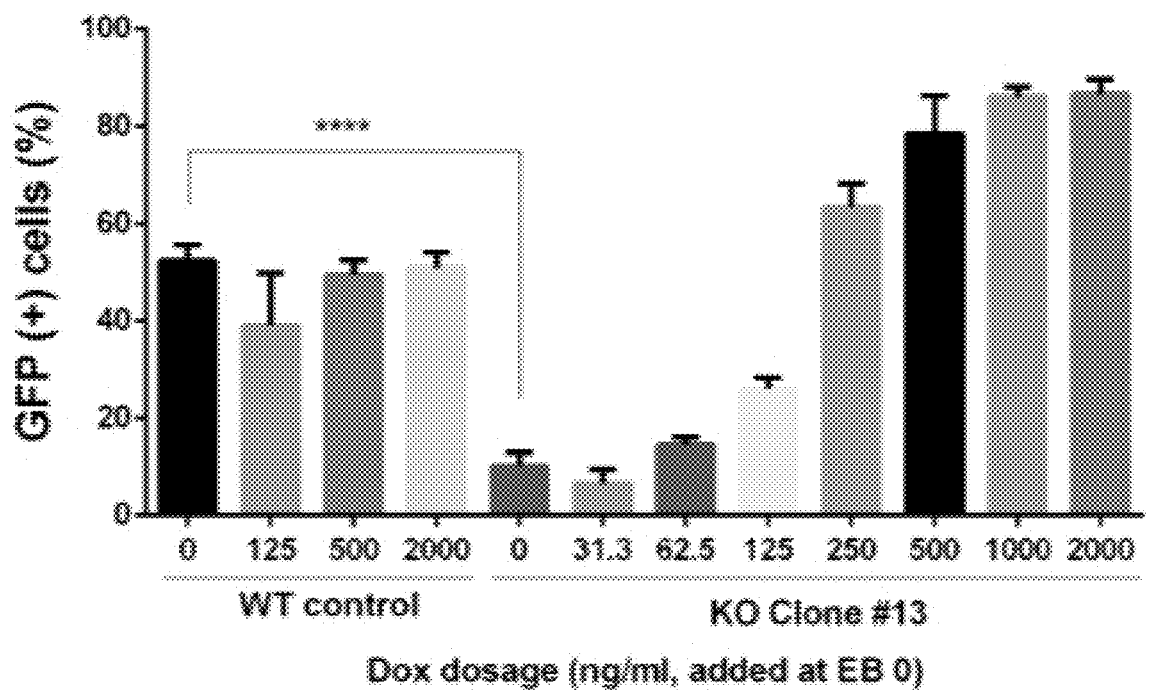

To account for this possibility, cell proliferation was monitored during differentiation and the proportion of Rx-GFP (+) RLCs formed from ESCs was assessed. Similar to observations in ESCs, it was observed that the loss of mWdr5 caused a severe reduction in proliferation in differentiating organoid cells at day 4 in retinal culture conditions. This proliferation defect in mWdr5 KO organoids was rescued in a dose-dependent manner by Dox treatment (added at T0h), which induced Wdr5 expression. This rescue effect reached a plateau at a Dox concentration of 250 ng/ml (FIG. 2C). Similarly, the proportion of Rx-GFP (+) RLCs formed from mWdr5 KO organoids was significantly reduced, but culture with Dox from T0h led to a high Rx-GFP(+) differentiation rate at day 5. In fact, the proportion of Rx-GFP (+) RLCs formed was comparable to the level of WT controls at a dose of 250 ng/ml and it reached a plateau at 500 ng/ml of Dox (FIG. 2D). The correlation between cell proliferation and RLC differentiation by Dox-induced exogenous hWDR5 suggests that cell proliferation is a prerequisite for RLC differentiation in mWdr5 KO organoids.

Figure 2E:
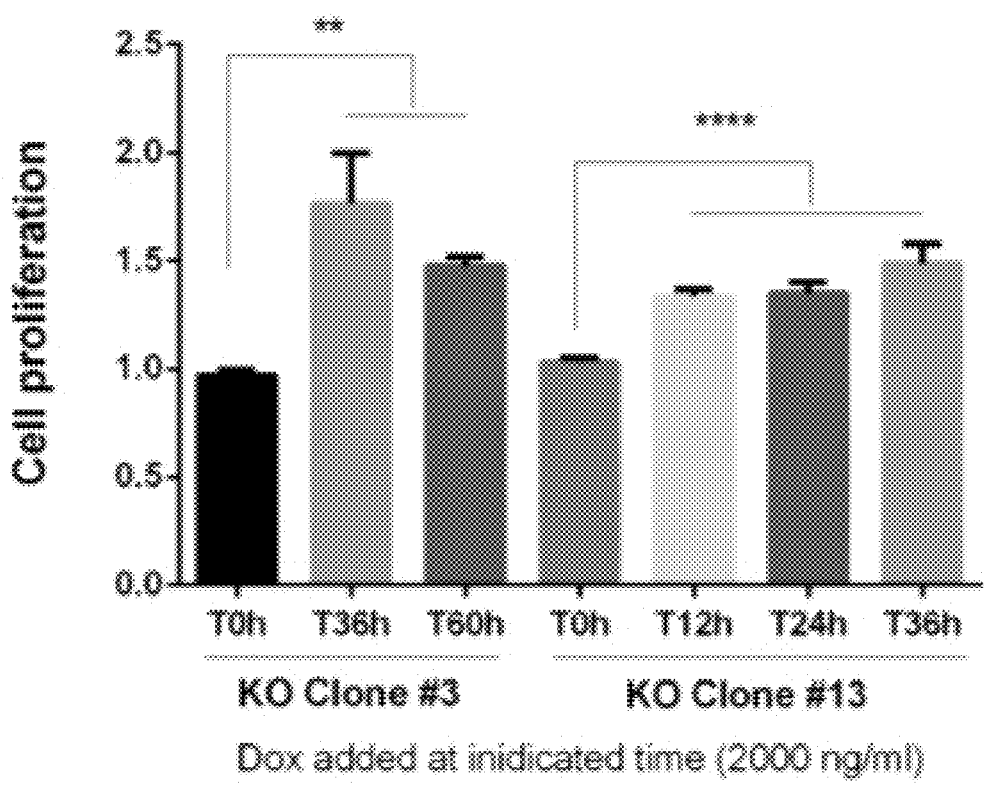

To identify a potential temporal window critical for exogenous hWDR5-mediated RLC differentiation, clonally distinct, differentiating hWDR5Dox;mWdr5KO organoids were pulsed with a single dose of Dox (2.0 µg/ml) at 12h intervals (control: Dox at T0h vs. no Dox at T0h, followed by Dox treatment at T12h, T24h, T36h, and the like). The addition of Dox to cultures up to 60h after differentiation was sufficient to support organoid growth (FIG. 2E).

Figure 2F:
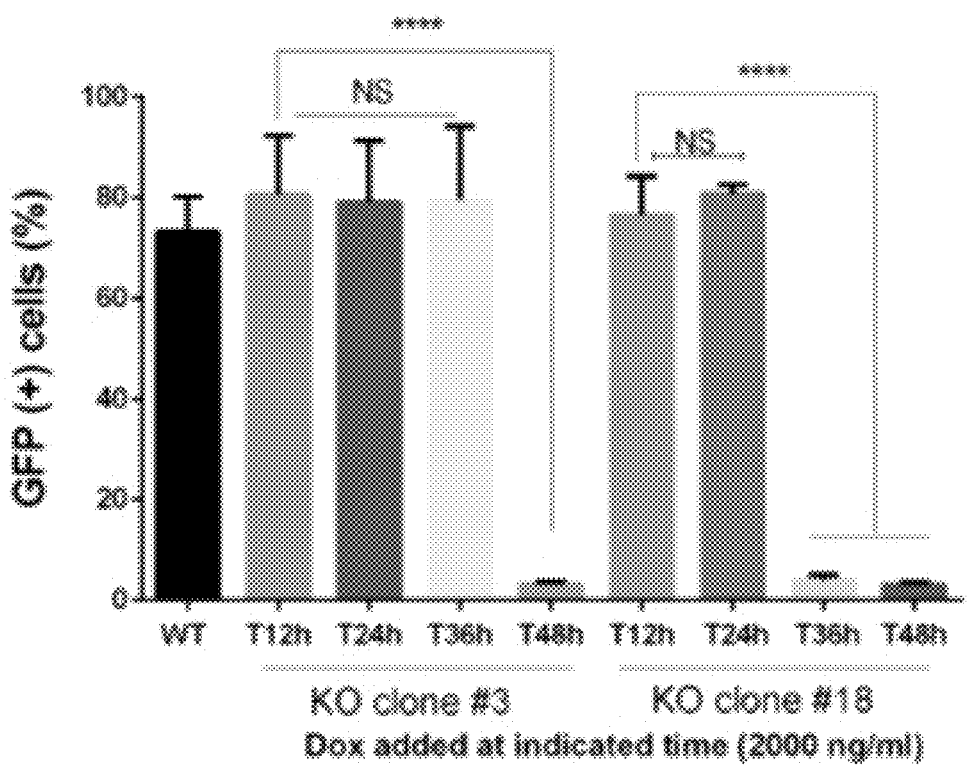
Figure 2G:
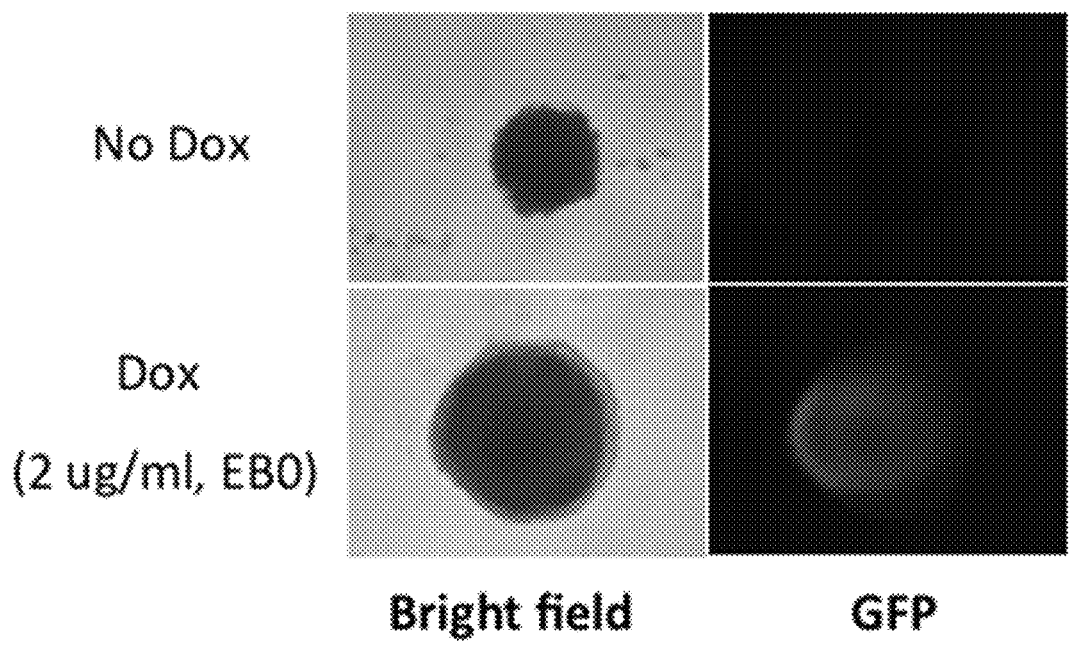
Figure 2H:
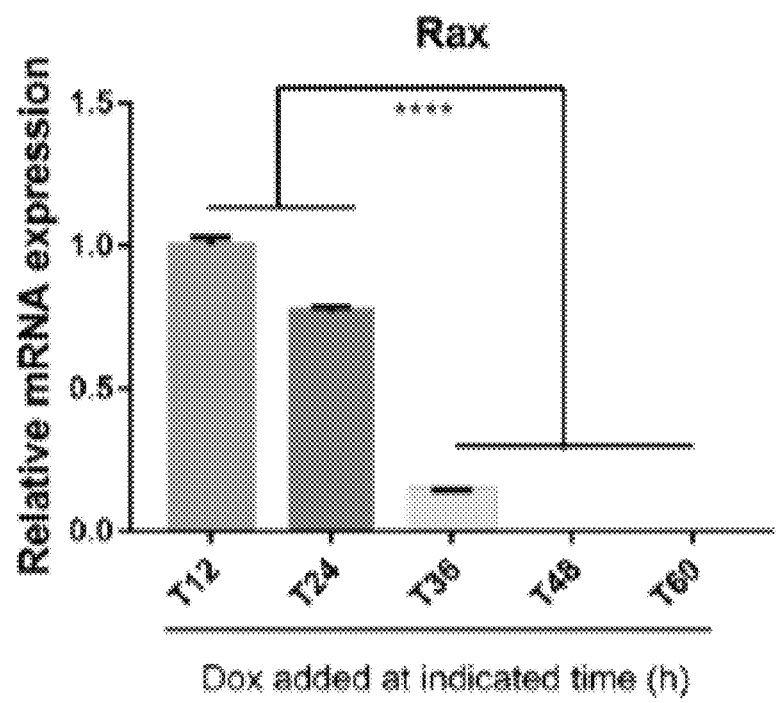
Figure 8A:
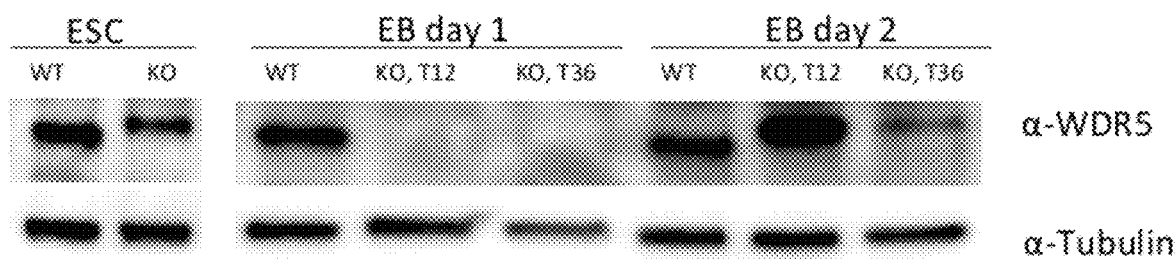
FIGS. 8A-8B. Dynamics of endogenous mWdr5 and Dox-inducible exogenous hWDR5 during ESC differentiation. hWDR5$^{Dox}$;mWdr5$^{KO}$ ESCs were maintained in Dox-containing media. Cells were maintained in Dox until it was removed upon differentiation, because endogenous WDR5 is knocked out in the cells, and the ESCs cannot survive without WDR5, absent for an extended period of time. Dox was removed upon differentiation and was added back to EBs at 12 h (T12h) or 36h (T36h) after differentiation. Cells were harvested at indicated time points for determining mWdr5 (lower band) or hWDR5 (higher band) expression via western blotting.
Figure 8B:
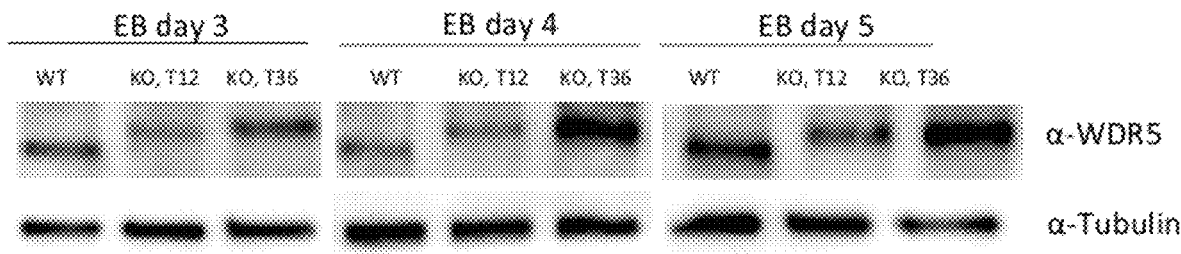

It was surprisingly found that the addition of Dox to cultures at T36h or later (or greater than 24h) resulted in defective Rx-GFP (+) RLC differentiation in mWdr5 KO EBs (FIG. 2F). Fluorescence microscopy of EBs (FIG. 2G) and RT-qPCR analysis of Rx mRNA expression (FIG. 2H) further confirmed that Dox-induced, exogenous hWDR5 expression supported RLC fate during early time points (addition of Dox at 0h or 12h after differentiation) in mWdr5 KO organoids. Western blotting revealed dynamic hWDR5 protein levels in mWdr5 KO organoids under early hWDR5 induction (T12h) conditions compared to WT endogenous controls (FIG. 8). These data indicate that RLC differentiation can proceed even in conditions in which WDR5 expression fluctuates during an early, critical differentiation phase (days 1-5 under T12h conditions). Collectively, these data demonstrate that the genetic Wdr5 dose controls proliferation and differentiation of ESCs in retinal culture conditions. Furthermore, Wdr5 spurs RLC fate at a critical, early phase of ESC differentiation.

Example 4—Early and Delayed Induction of hWDR5 in mWDR5 KO Organoids Result in Distinct Global Gene Expression Profiles Experimental results set out herein above identified a temporal window (a window after about 24 h up to about 60h after differentiation, termed as delayed or late induction) during which expression of exogenous hWDR5 following transient mWDR5 loss resulted in impaired retinal neuroectoderm differentiation while cell proliferation was not compromised.

Figure 3B:
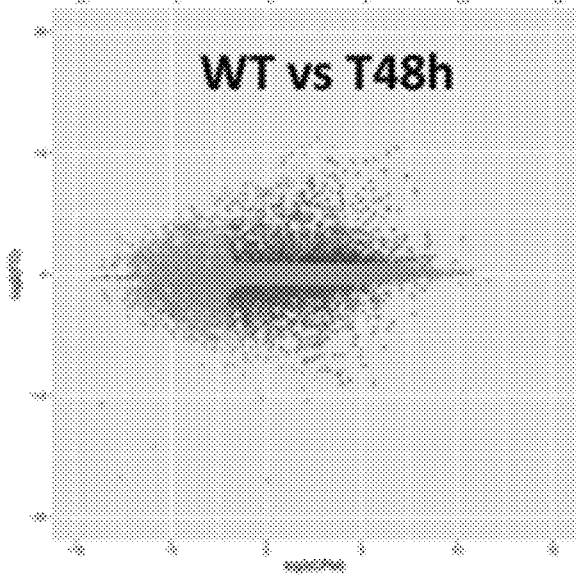
Figure 9A:
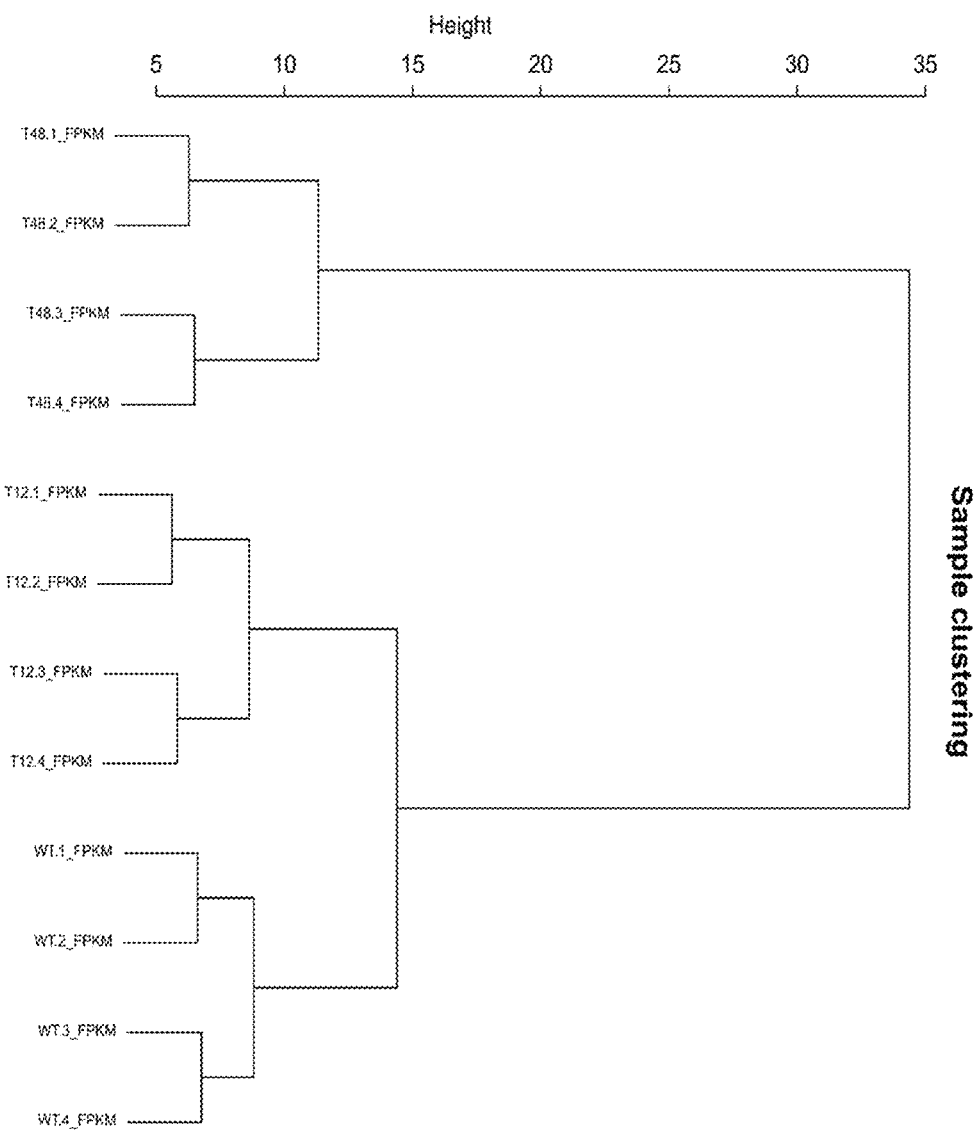
FIGS. 9A-9C. Retinal neuroectoderm and mesoderm specification by temporal induction of exogenous hWDR5 in hWDR5$^{Dox}$;mWdr5$^{KO}$ EBs is accompanied by distinct global transcription profiles.

To gain insights of what cell types form from mWDR5 KO organoids with late induction of exogenous hWDR5, EB day 6 (or organoid day 6) RNA was isolated from 3 groups, i.e., WT, mWDR5 KO organoids with early (T12h), or late (T48h) induction of exogenous hWDR5. RNAs from these three groups were subjected to RNA-sequencing (RNA-Seq) and bioinformatics analyses. Non-supervised clustering revealed that WT and T12h groups were most closely related (FIG. 9A), consistent with the observation that a high proportion of Rx-GFP (+) RLCs were formed in both conditions (FIG. 2F). In contrast, the T48h group was most distantly separated from WT and T12h groups (FIG. 9A). Volcano plots showed that WT and T12 groups had 593 differentially expressed genes using 2-fold difference as a cutoff (FIG. 3A), while WT and T48 groups displayed 2,753 genes with differential expression (FIG. 3B).

Figure 3C:
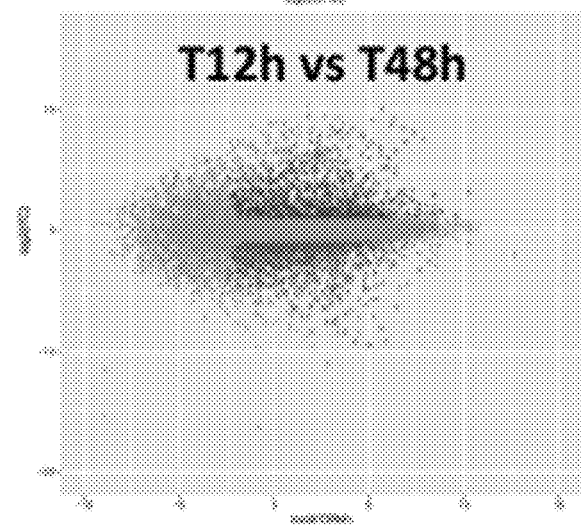
Figure 3D:
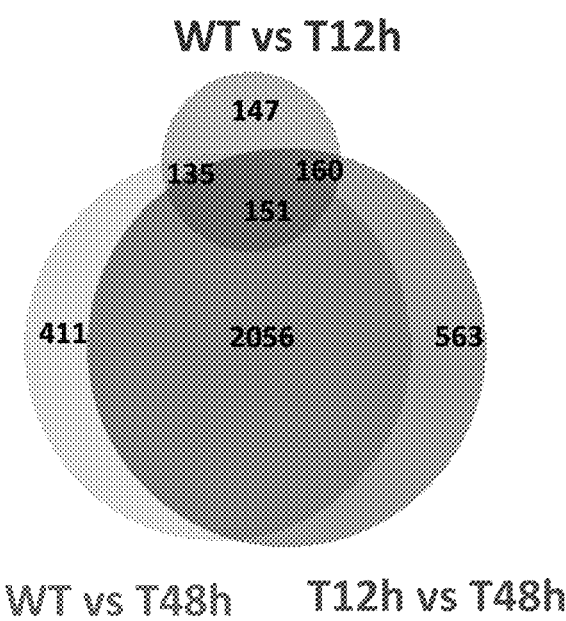
Figure 3E:
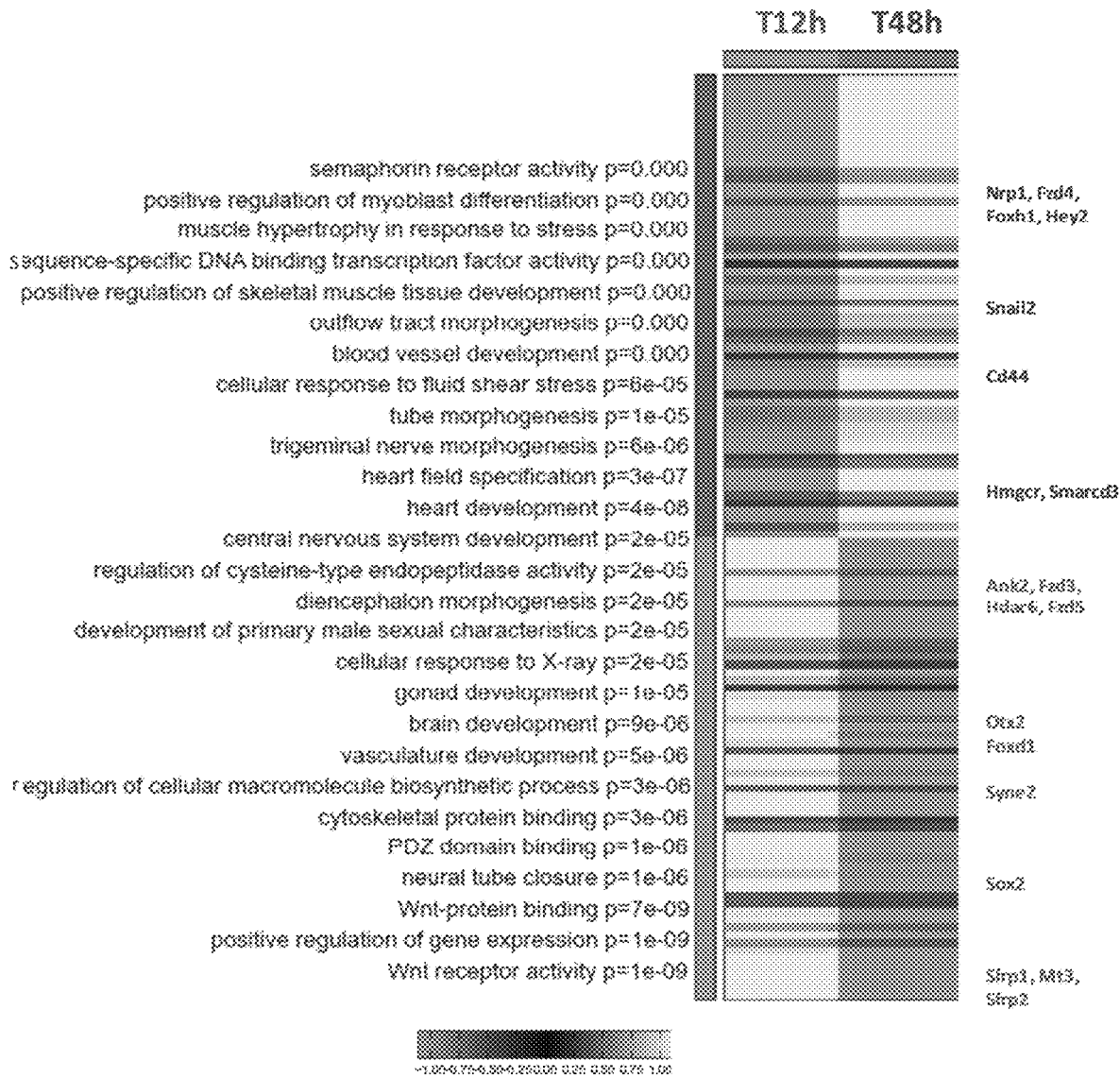
Figure 9B:
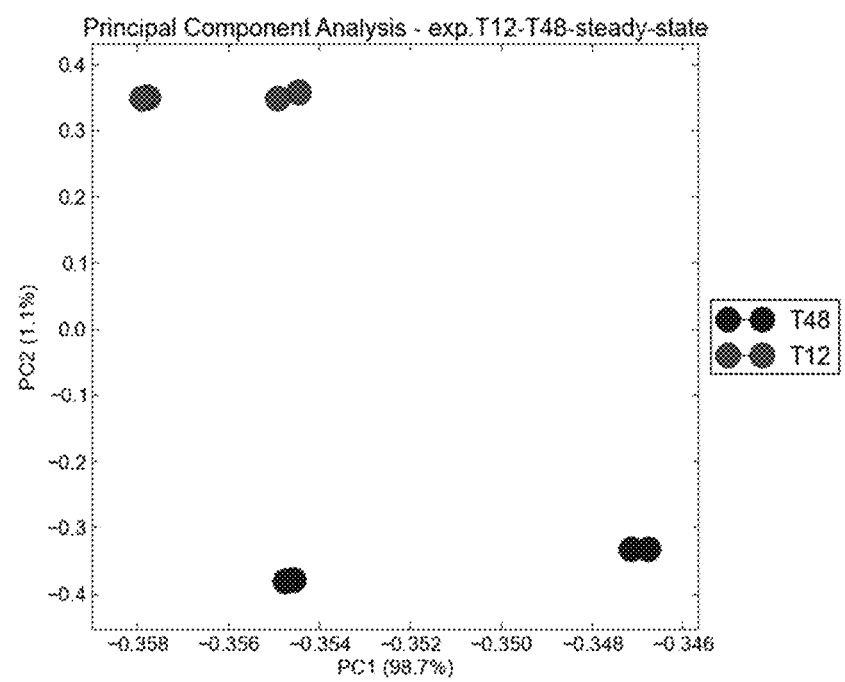
Figure 9C:
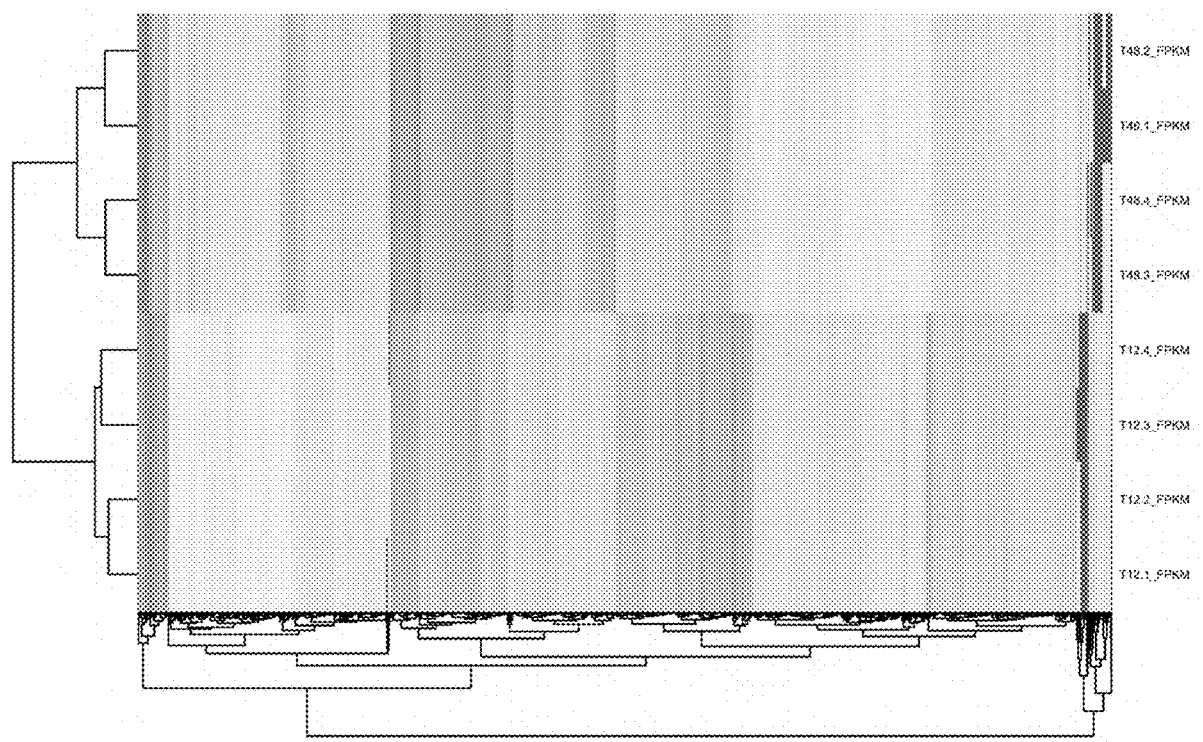

Similarly, comparison of T12 and T48 groups generated 2,930 genes with 2-fold, up- or down-regulation (FIG. 3C). The analysis revealed a largely overlapping set of differentially expressed genes (75-80%) between WT vs. T48h and T12h vs. T48h, further supporting the conclusion that gene expression profiles of WT and T12h groups were similar, and that both these groups (i.e. WT and T12h) harbored an RNA profile distinct from the T48h group (FIG. 3D). The data, represented by principal component and heatmap analyses, indicated that T12h and T48h groups were distinct from each other (FIG. 9B-C). Gene ontology analysis performed from the RNA-seq data in T12h vs. T48h showed that the T12h group highlighted processes related to central nervous system development as well as WNT-pathway regulation, while biological themes in the T48h group emphasized mesoderm development including heart, myoblast and blood vessel development (FIG. 3E).

Collectively, these genome-wide RNA-Seq data indicate that T12h early induction of exogenous hWDR5 in hWDR5$^{Dox}$;mWdr5$^{KO}$ organoids recapitulates default RLC-enriched, neuroectodermal formation, similar to that of WT control culture conditions. In contrast, delayed hWDR5 induction at T48h leads to a differentiation program favoring enhanced expression of mesoderm-related genes.

Example 5—Late Induction of WDR5 Skews ESC Differentiation from Retinal Neuroectoderm Toward Cardiac Mesoderm Since gene ontology analysis of RNA-Seq data from late (T48h) induction of hWDR5 in mWdr5 KO organoids indicated an overrepresented subset of genes responsible for mesoderm including heart and blood vessel development, experiments were undertaken to confirm that mesoderm-lineage cells were indeed generated under these conditions.

Figure 4A:
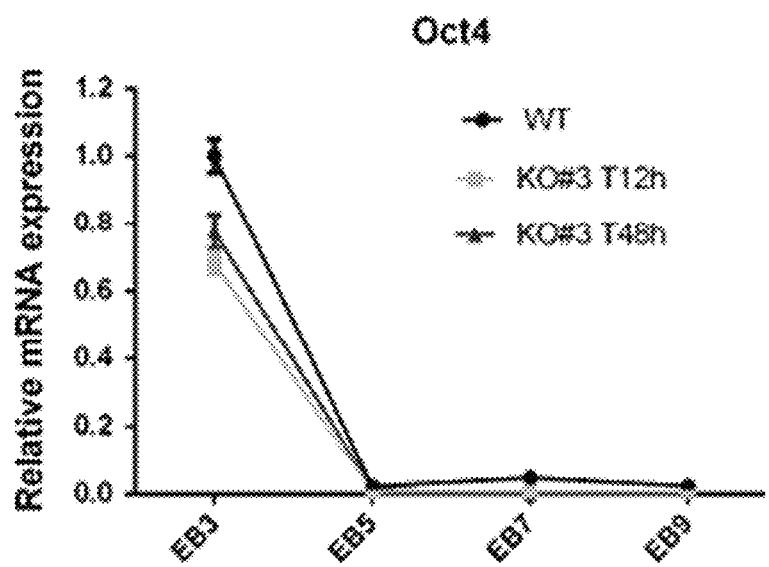
FIGS. 4A-4K. Late induction of hWDR5 skews ESC differentiation from retinal neuroectoderm to cardiac mesoderm.

First, RT-qPCR was used to analyze a variety of pluripotent and lineage-specific gene expression in differentiating organoids from days 2 to 9 in retinal culture conditions. Gradual silencing of the core pluripotent gene Oct4 indicated differentiation in all groups (FIG. 4A).

Figure 4B:
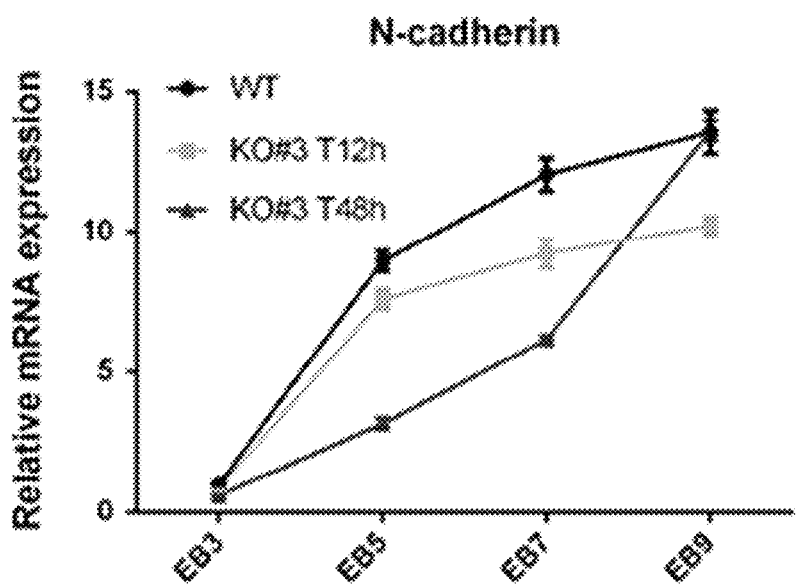
Figure 4C:
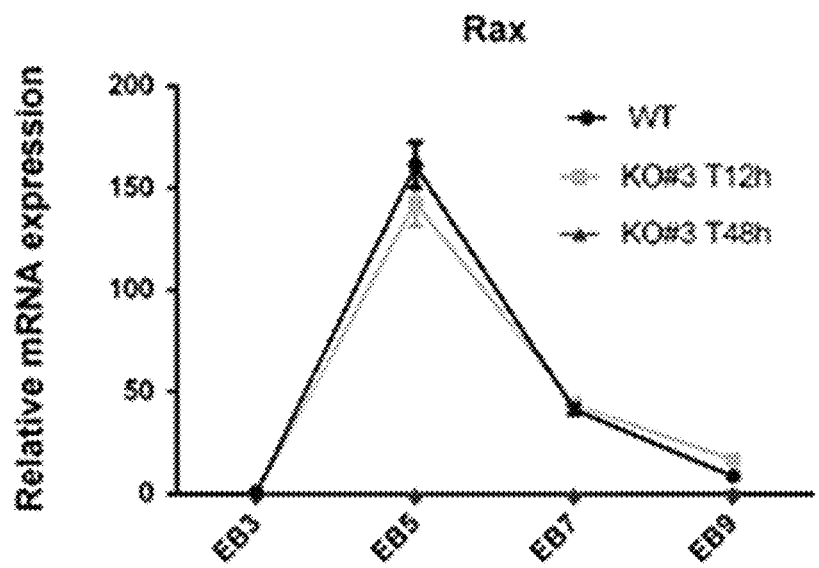

N-cadherin (Ncad) is a neuroepithelial marker for retinal organoids (Eiraku et al., 2011), and is also upregulated during epithelial-to-mesenchymal transition (EMT) during spontaneous ESC differentiation (Honda et al., 2006). Ncad expression was induced in all groups, and reached higher levels at EB5 in WT and T12h conditions compared to T48h, though this difference was not present at EB9 (FIG. 4B). In contrast, Rax/Rx expression increased rapidly, peaking at EB5, and decreasing by EB9 in WT and T12h groups, indicating RLC differentiation (FIG. 4C). In T48h conditions, however, Rax/Rx expression was barely detected even though culture conditions favoring retinal differentiation (FIG. 4C).

Figure 4D:
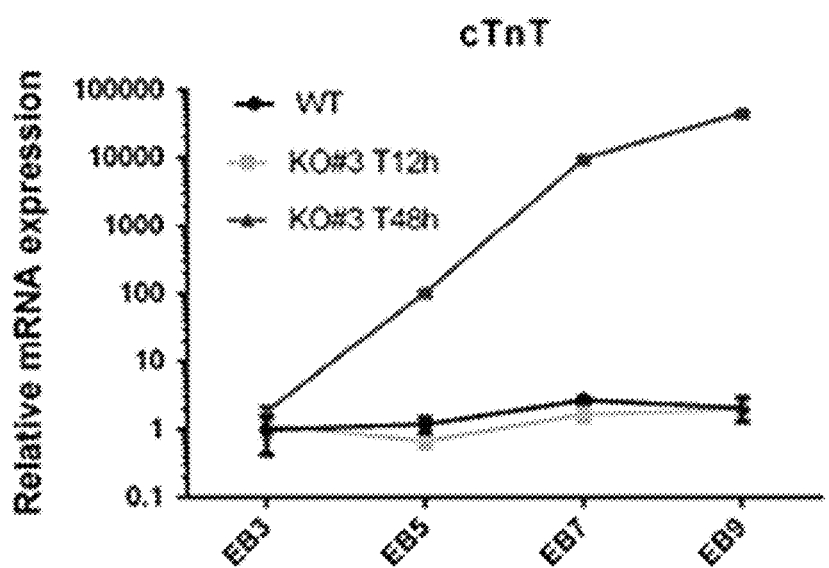
Figure 10A:
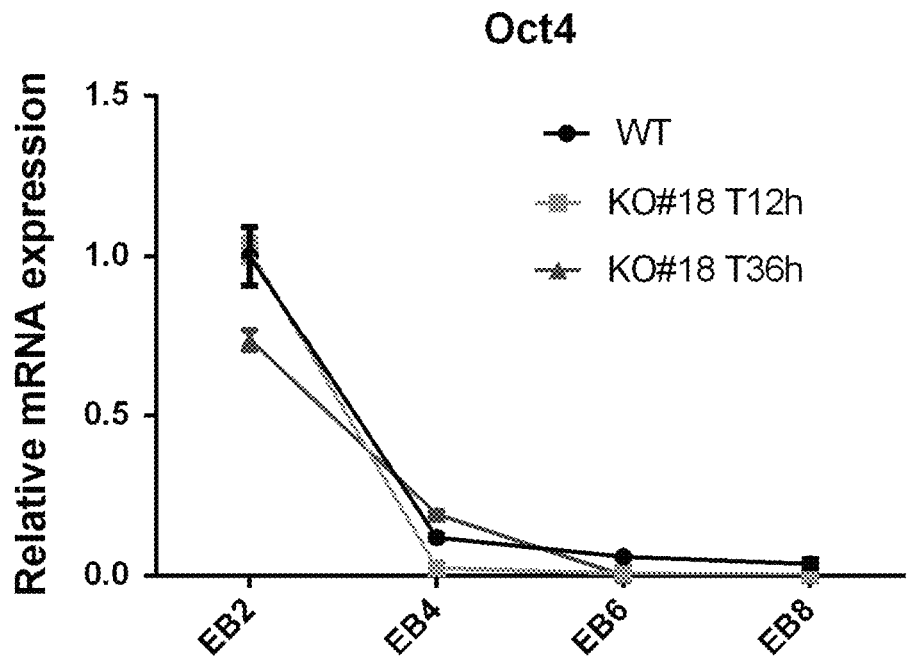
FIGS. 10A-10Q. Early and late induction of exogenous hWdr5 in hWDR5$^{Dox}$;mWdr5$^{KO}$ (i.e., mWdr5 KO) ESCs upon differentiation dictate different cell fate.
Figure 10B:
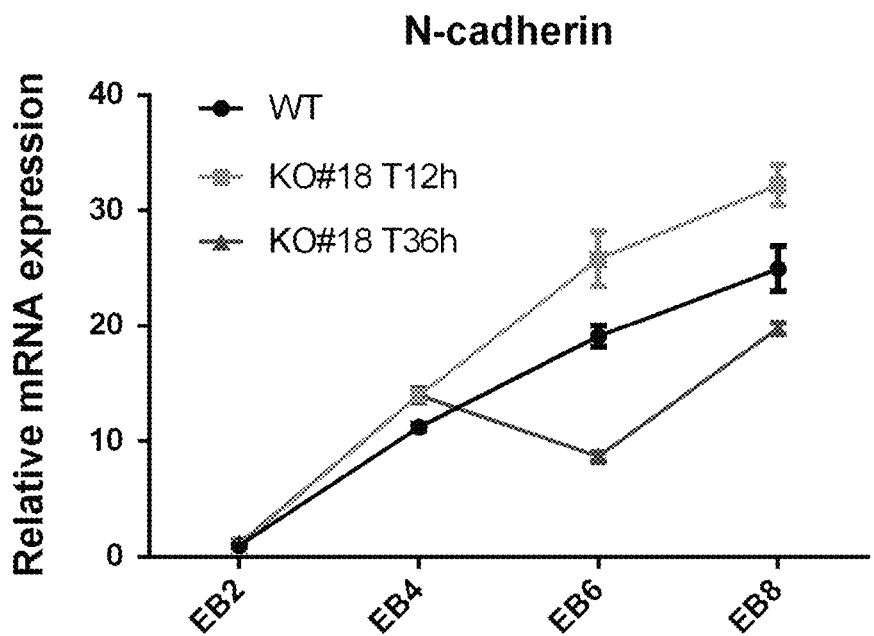
Figure 10C:
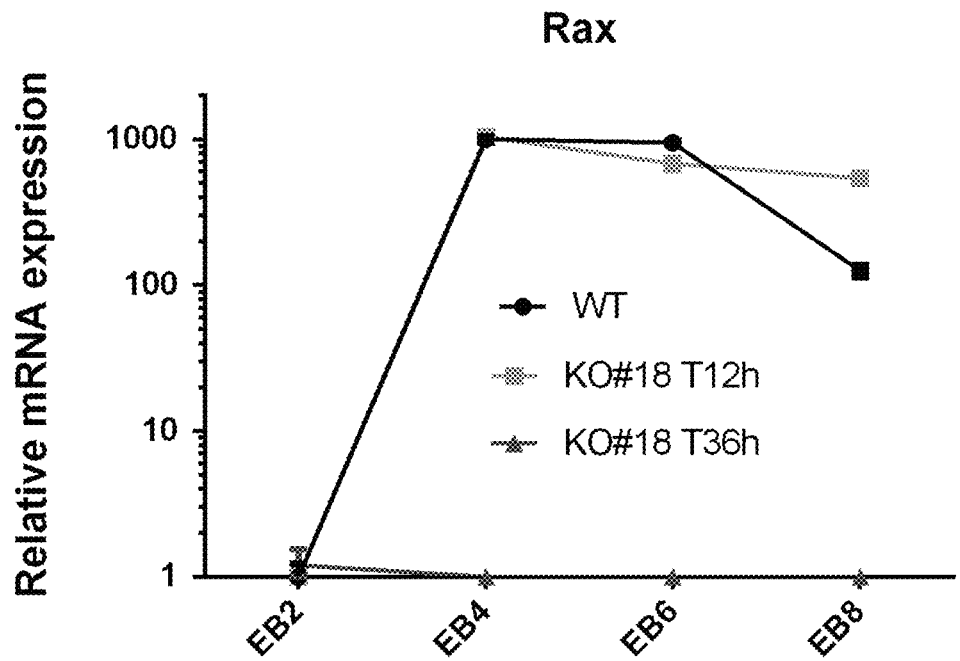
Figure 10D:
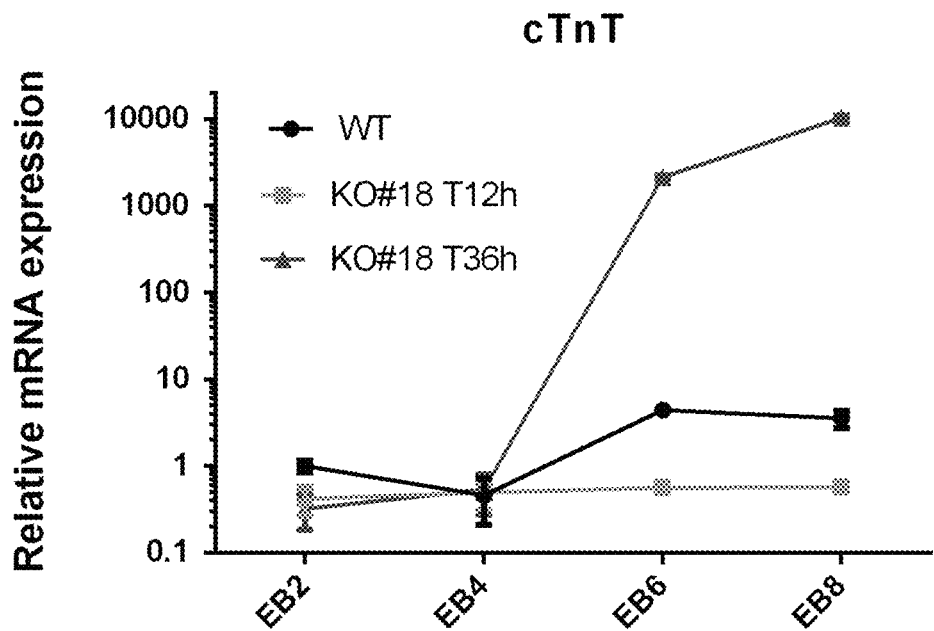
Figure 10E:
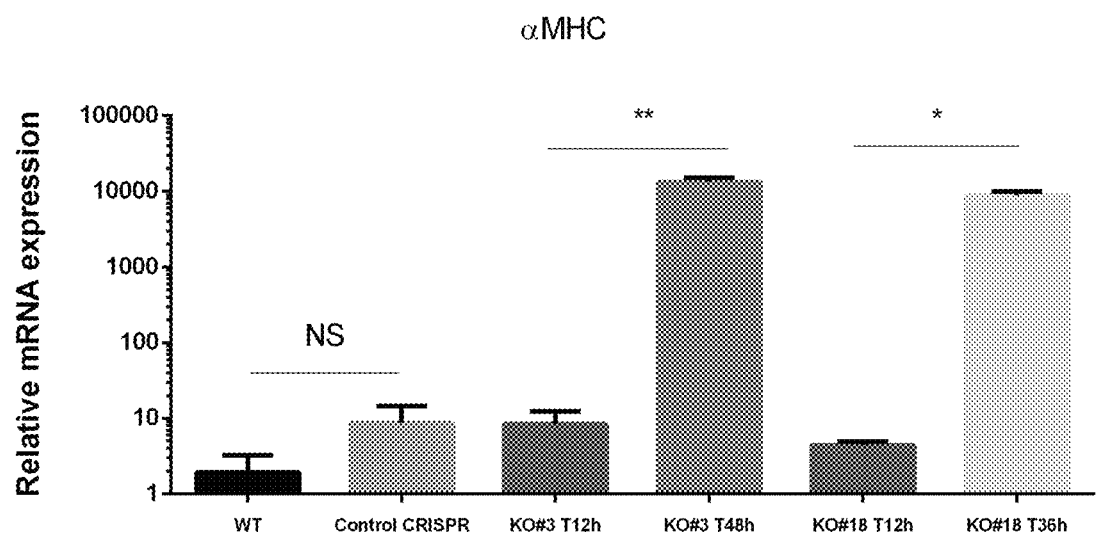
(FIGS. 10E, 10F and 10G) Induction of cardiomyocyte differentiation (EB day 6) by late induction of exogenous hWDR5 in two independently-edited mWdr5 KO ES clones were further subjected to RT-qPCR analysis of cardiomyocyte markers α-MHC (FIG. 10E), β-MHC (FIG. 10F) and Myocd (FIG. 10G).
Figure 10F:
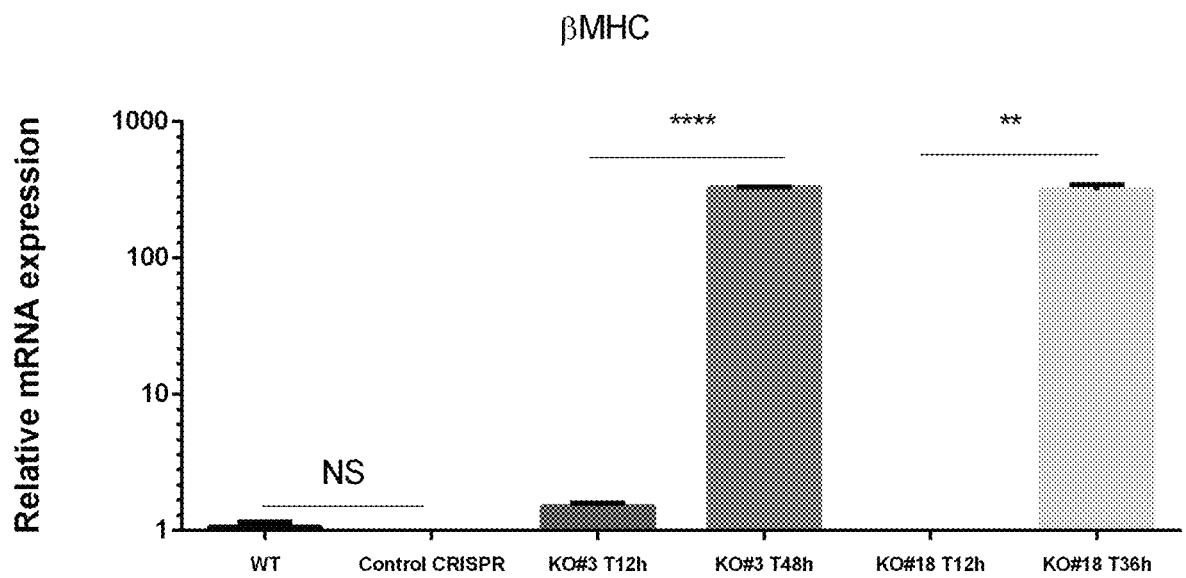
Figure 10G:
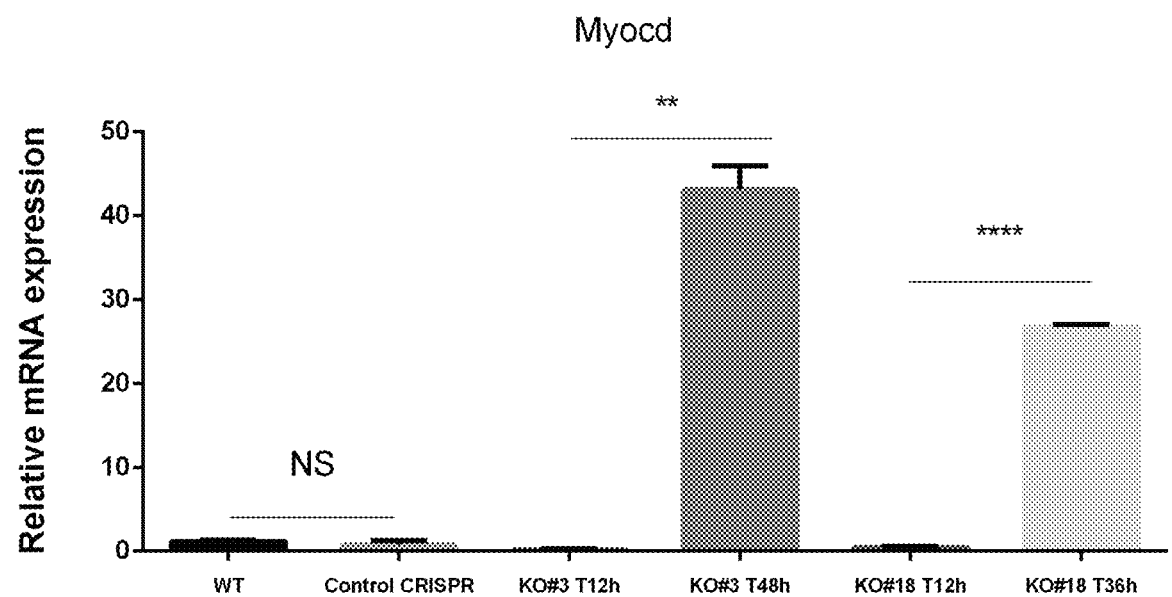

These RT-qPCR data remain consistent with earlier flow cytometry findings showing impaired Rx-GFP+ RLC differentiation when hWDR5 expression was reintroduced at T48h (FIG. 2F). Strong induction (up to 10,000-fold) of the cardiomyocyte specific marker cardiac troponin T (cTnT) was observed in T48h from day 5 to 9, in contrast, cTnT expression was not induced in WT or T12h conditions (FIG. 4D). De novo induction of cTnT by late induction (T36h) of hWDR5 was also observed in another independent hWDR5$^{Dox}$;mWdr5$^{KO}$ clone (FIG. 10D). Other cardiomyocyte markers, such as alpha and beta-isoforms of myosin heavy chain (aMHC/Myc6 and βMHC/Myh7), and myocardin (Myocd) mRNA, were invariably and robustly induced at EB6 by late induction of hWDR5, but not in control groups (FIG. 10E-G).

Second, morphological evidence for cardiomyocyte differentiation was observed. Virtually all hWDR5$^{Dox}$;mWdr5$^{KO}$ organoids with late induction of hWDR5 visibly contracted by days 8-9, but not in control groups.

Figures 4E, 4F, 4G:
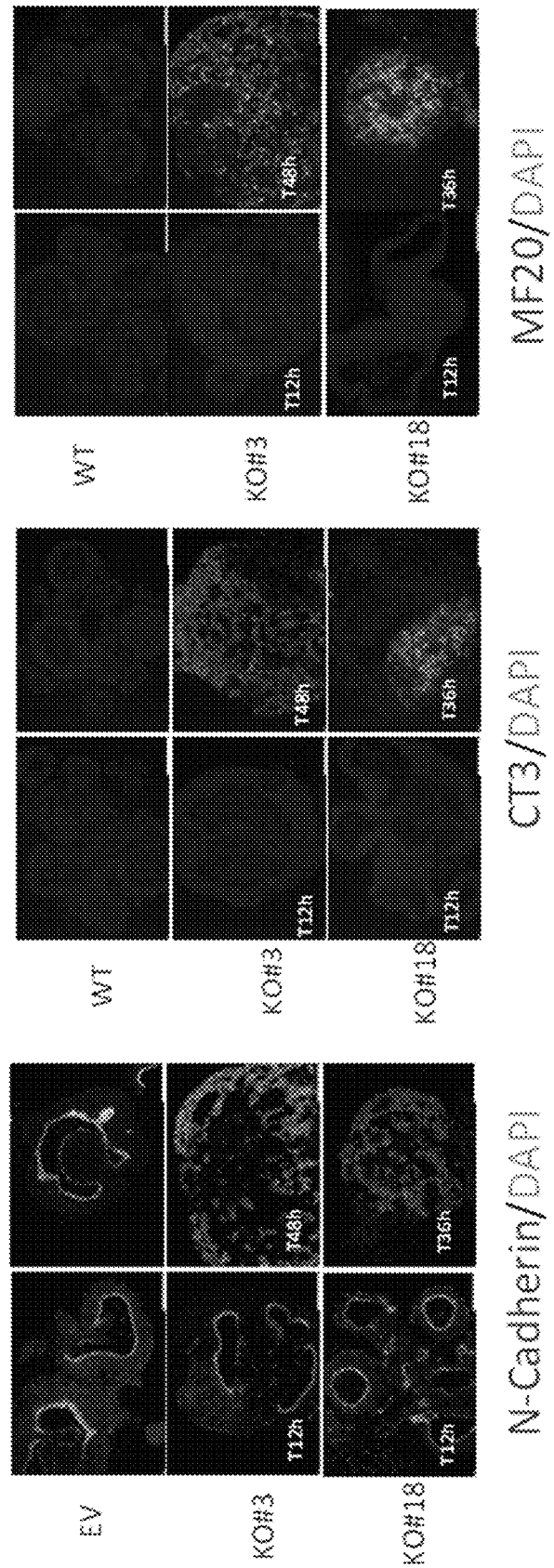
Figure 4H:
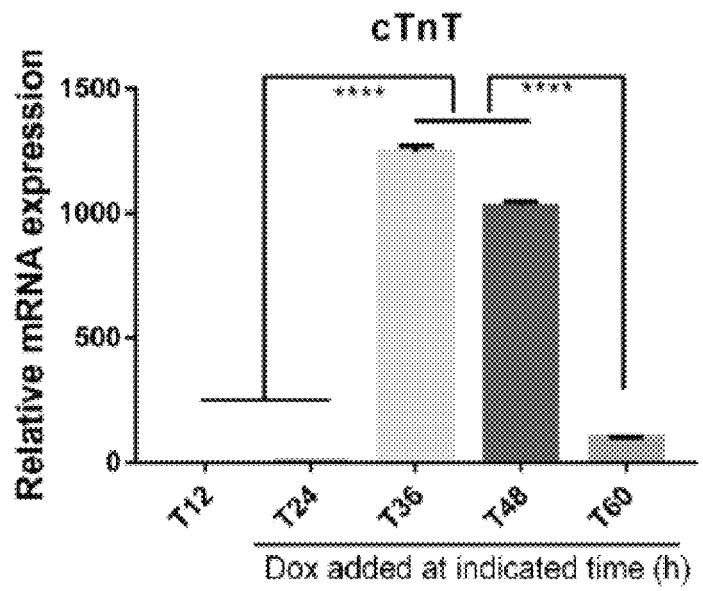
Figure 4I:
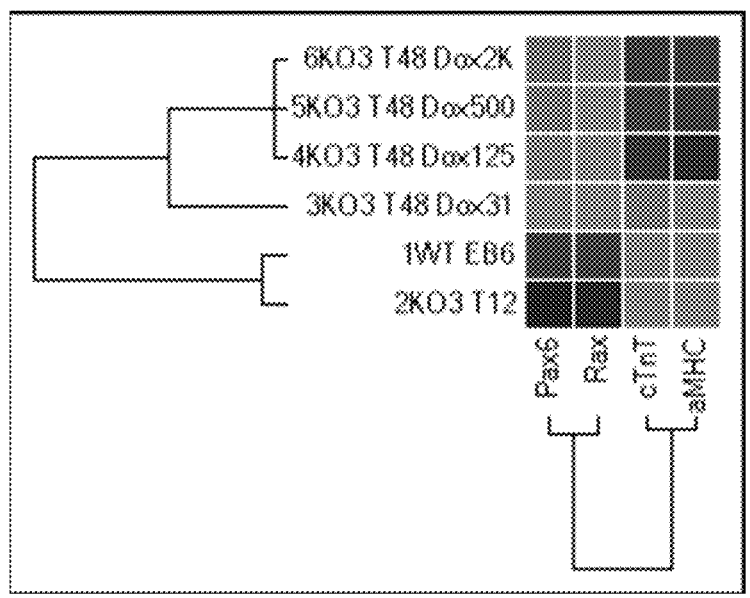
Figure 4J:
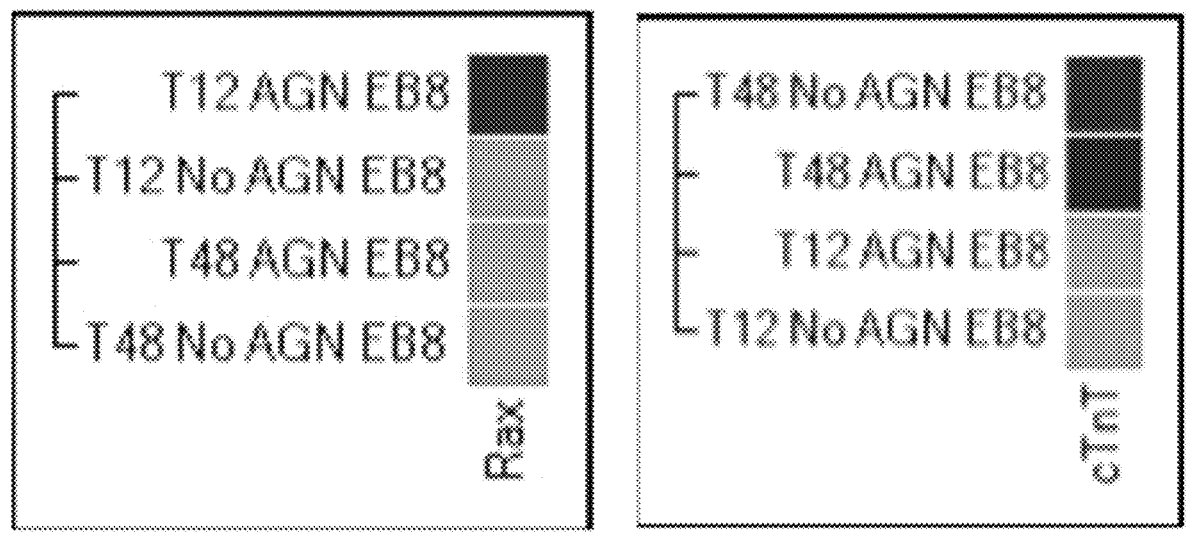
Figure 10H:
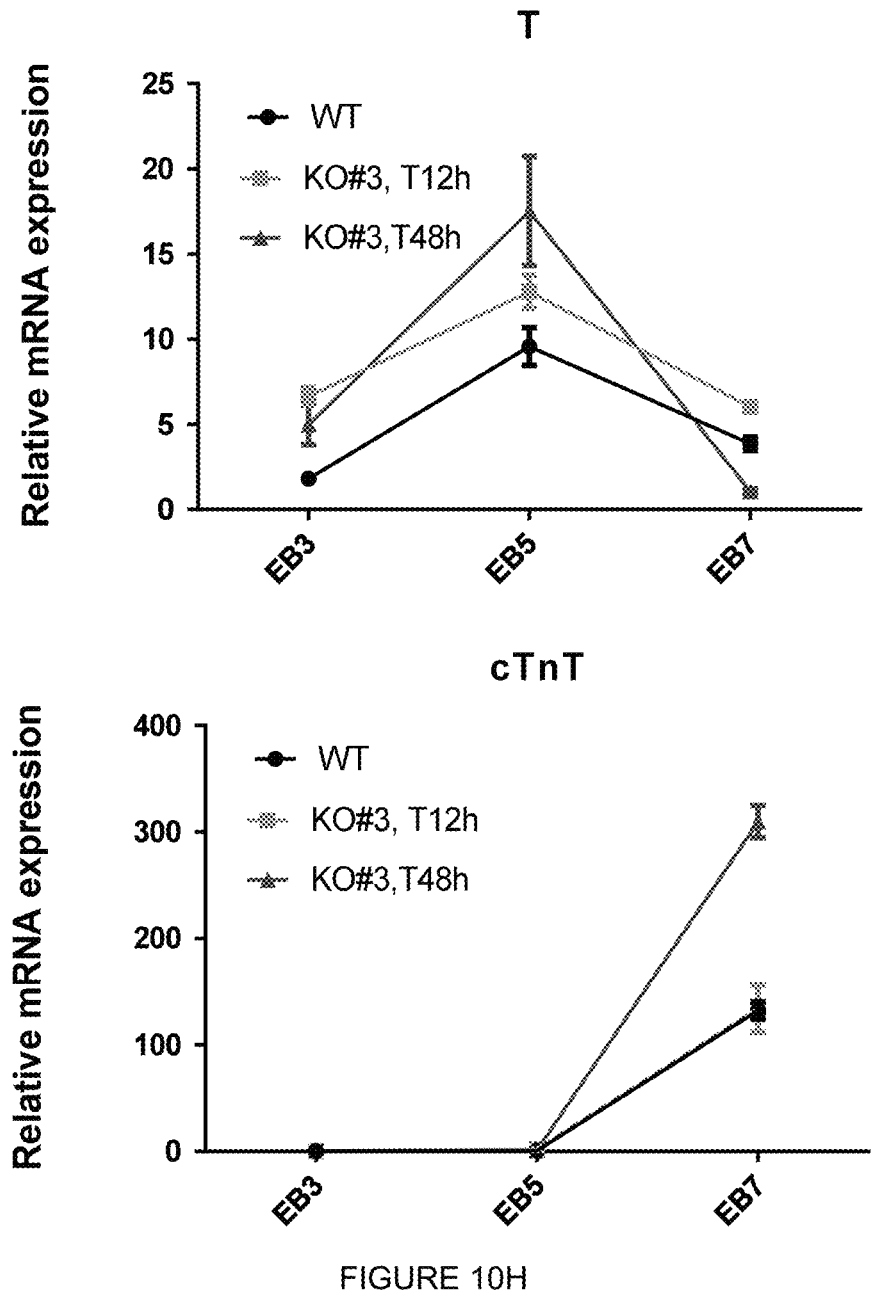
(FIG. 10H) RT-qPCR analysis of T (left panel) and cTnT expression (right panel) in day 8 WT and mWdr5 KO EBs in mesoderm-permissive differentiation conditions (replacement of 10% knockout serum replacement in SFEB methods with 10% fetal calf serum).
Figure 10I:
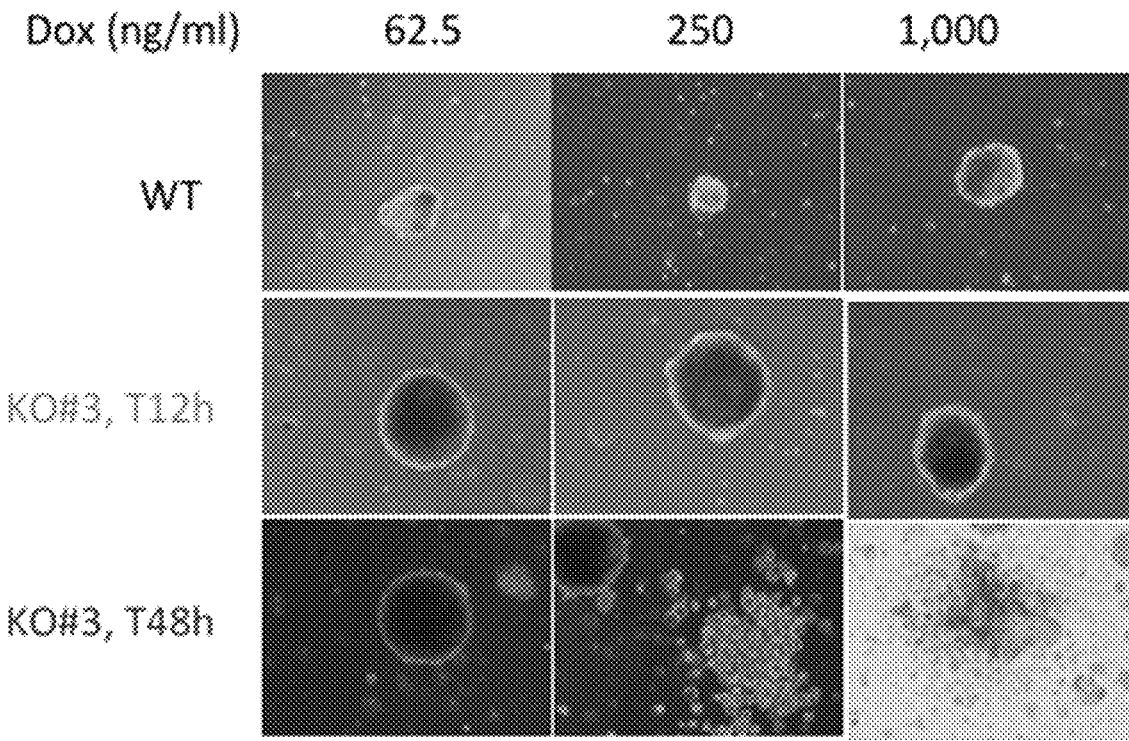
(FIGS. 10I and 10J) Hematopoietic lineage cells derived from day 6 EBs were evaluated by methylcellulose-based colony forming unit (CFU) assay. 1.5λ10^5 cells from day 6 EB was transferred into retinal differentiation culture conditions and seeded on methylcellulose in the presence of IL-3, GM-CSF, SCF and different doses of Dox. The representative pictures of resultant secondary EBs and CFU was recorded (FIG. 10I) and counted at day 9 after secondary differentiation (FIG. 10J).
Figure 10J:
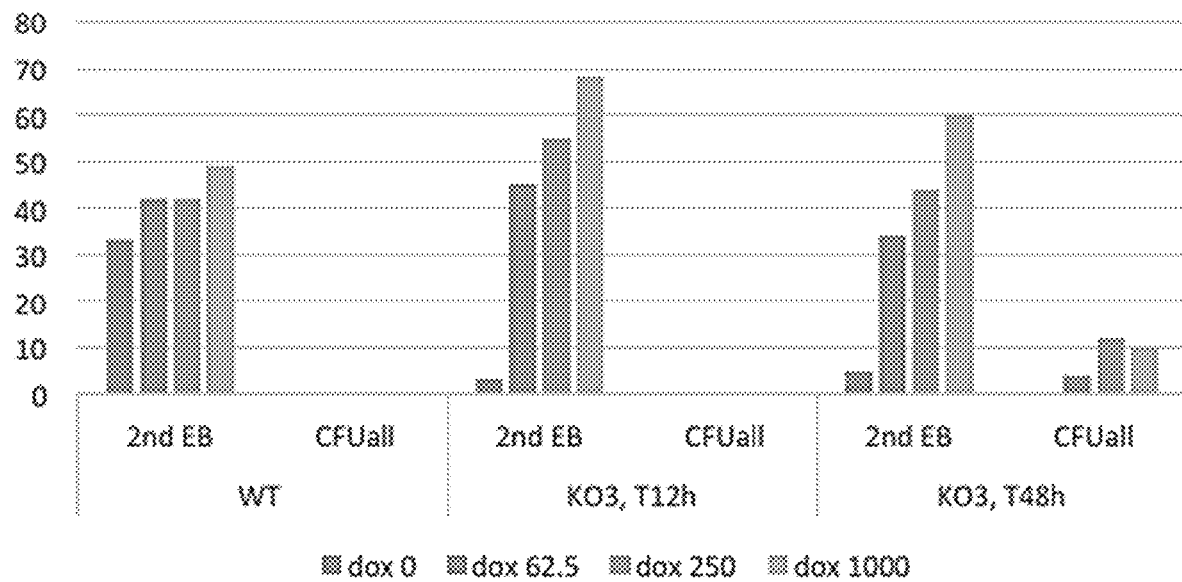

Third, immunohistochemistry (IHC) was used to assay for cardiomyocyte-specific proteins in T48h conditions. Polarized distribution of Ncad in WT and T12 organoids—with the apical surface inside—indicated retinal neuroepithelium differentiation (Eiraku et al., 2011). In contrast to the polarized pattern of Ncad expression observed in Rx-GFP RLCs generated in WT and T12h conditions, Ncad was broadly distributed within the cytoplasm of cells that arose in T36h or T48h conditions, which was reminiscent of cardiomyocyte differentiation (Honda et al., 2006) and confirmed in two independent hWDR5$^{Dox}$;mWdr5$^{KO}$ clones (FIG. 4E). Contractile organoids in T36 or T48h groups showed robust staining for cTnT (CT3 antibody, FIG. 4F) and myosin heavy chain 1e (Myhle, MF20 antibody, FIG. 4G), which were consistent with cardiomyocyte differentiation. Neither cTnT nor Myh1e were detected in WT and T12h conditions. To further confirm that cardiomyocyte differentiation in hWDR5$^{Dox}$;mWdr5$^{KO}$ organoids was dependent on WDR5, time and dose response experiments to exogenous hWDR5 were carried out. Treatment of hWDR5$^{Dox}$;mWdr5$^{KO}$ organoids with Dox at different timepoints revealed that hWDR5 induction at 36h to 48h was the optimal time window for maximal cTnT expression (FIG. 4H). However, addition of Dox at T60h remarkably reduced cTnT induction although cell proliferation was not compromised at this time point (FIG. 2E). At T48h, Dox concentrations up to 125 ng/ml induced cTnT and aMHC expression (FIG. 4I), indicating cardiomyocyte differentiation was WDR5 dose-dependent. To exclude the possibility that T48h-induced cardiomyocyte differentiation is dependent on the particular retinal organoid based differentiation platform used, alternate differentiation conditions were used. Indeed, the induction of cTnT was observed even with removal of the retinoic acid receptor antagonist AGN193109 (AGN), which stimulates retinal differentiation (FIG. 4J) (Assawachananont et al., 2014), or by using the Matrigel-free SFEB differentiation method (FIG. 4K) (Osakada et al., 2009). In fetal bovine serum-containing culture conditions that favor mesoderm differentiation and suppress ectoderm formation, cTnT induction in T48h conditions was 3-fold higher than WT and T12h settings (FIG. 10H). The data indicate that cardiomyocyte differentiation by late induction of hWDR5 is not simply a consequence of skewed or default ESC differentiation. Rather, late induction of hWDR5 directly stimulates cardiomyocyte differentiation in a dose- and time-dependent manner.

Figure 4K:
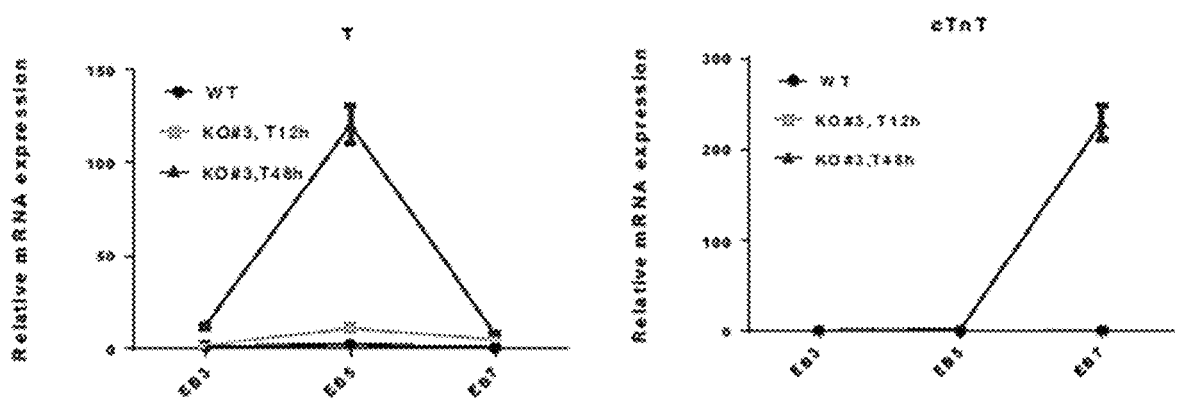

To address whether cell types other than those of the cardiomyocyte-lineage form in the T48h group, hematopoietic culture conditions were tested. Such culture conditions were tested because cardiomyocytes and hematopoietic cells share a common mesoderm ancestor, i.e., Flk1+ hemangioblast cells, which emerge during early ESC differentiation (Kouskoff et al., 2005). Re-seeding of day 6 or day 9 EBs (organoids) in semi-solid methylcellulose media favoring hematopoietic lineage differentiation indeed generated typical colony forming units of granulocyte, erythrocyte, monocyte and macrophage (CFU-GEMM) progenitors in T48h conditions (FIG. 10I-L). In contrast, secondary organoids, but not CFU-GEMMs, were observed in WT and T12h groups, which is consistent with induction of mesoderm early differentiating master regulator T in T48h group, but not WT and T12h groups (FIG. 4K). Collectively, these data indicate that late hWDR5 induction promotes differentiation of mesoderm lineage cells from ESCs capable of hematopoietic, as well as cardiac lineage cell differentiation.

Figure 10K:
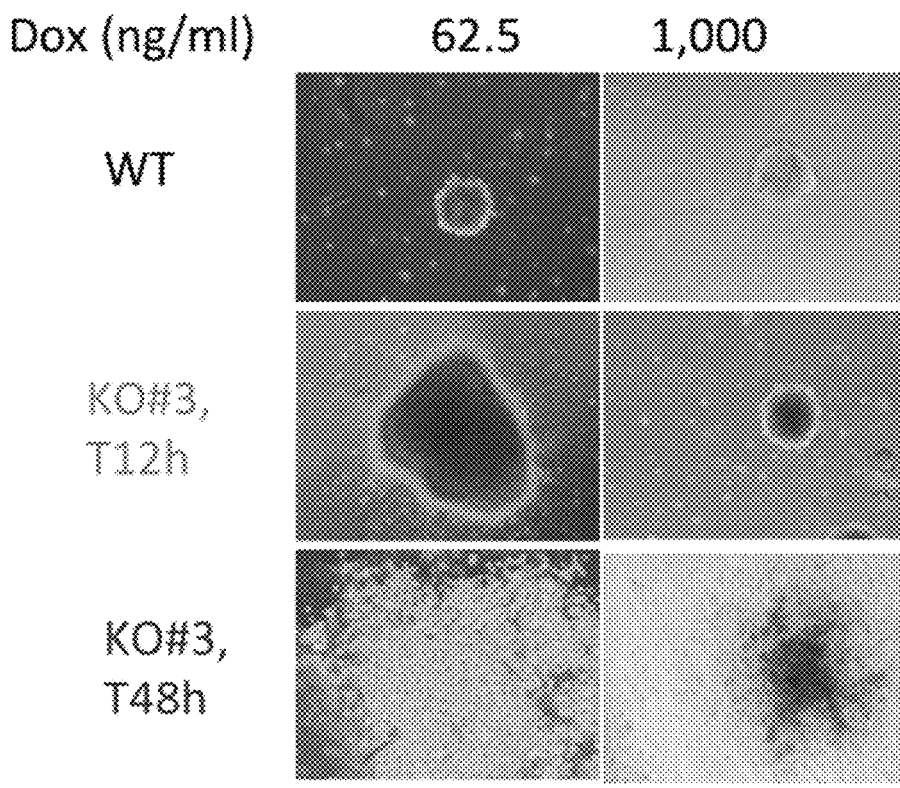
(FIGS. 10K and 10L) Replated day 9 EBs in WT and mWdr5 KO EBs with early (T12h) or late (T48h) induction of hWDR5 were tested for hematopoietic lineage cell formation using the same methods described in I and J.
Figure 10L:
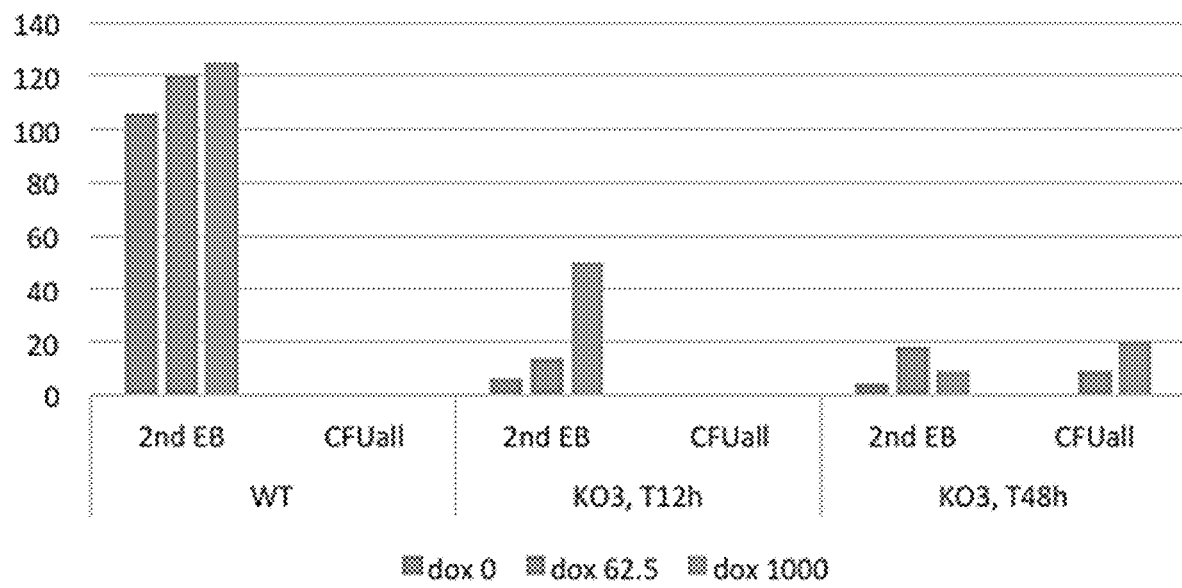
Figure 10M:
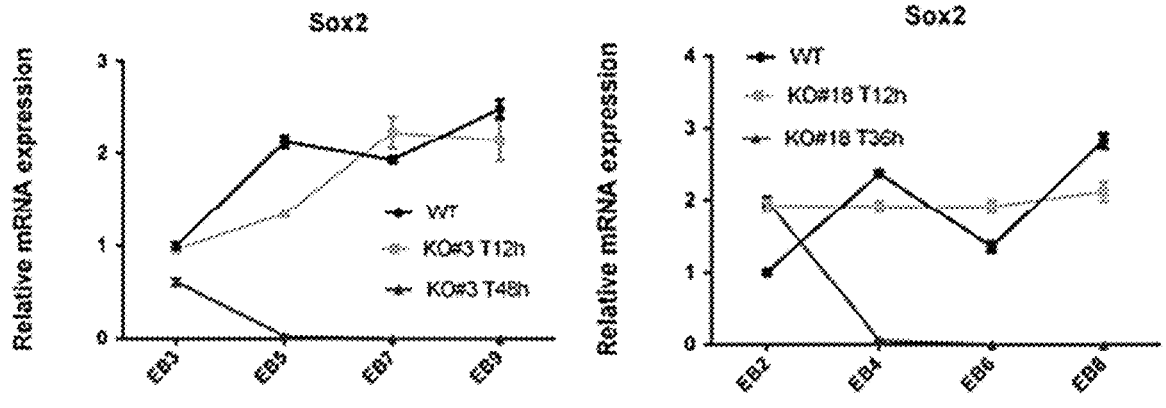
Figure 10N:
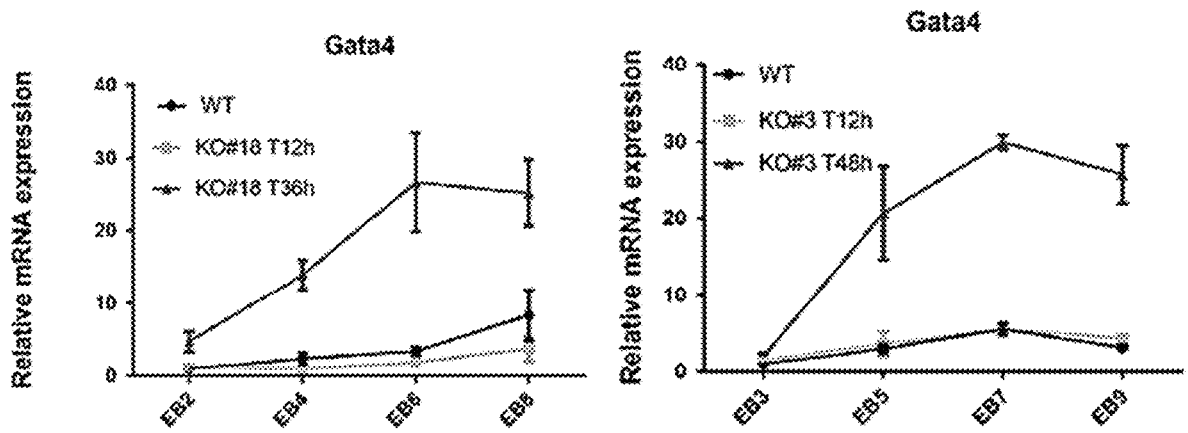
Figure 10O:
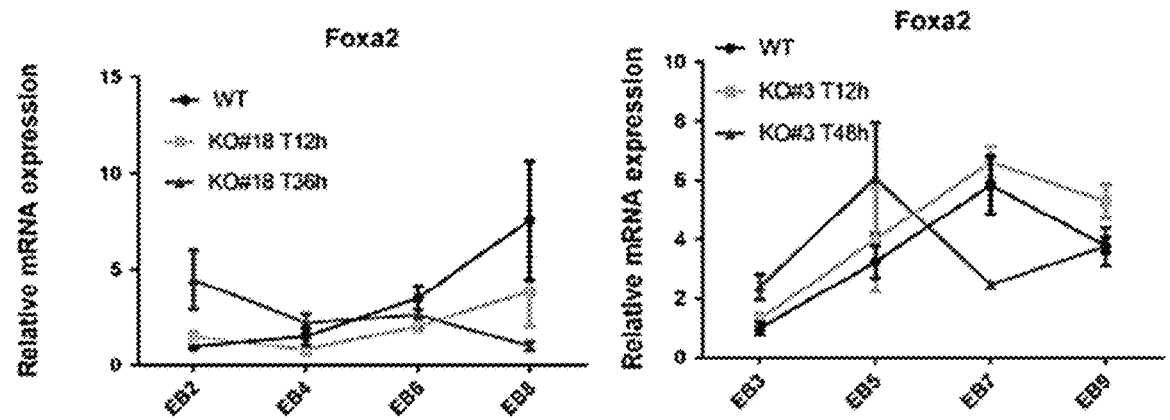
Figure 10P:
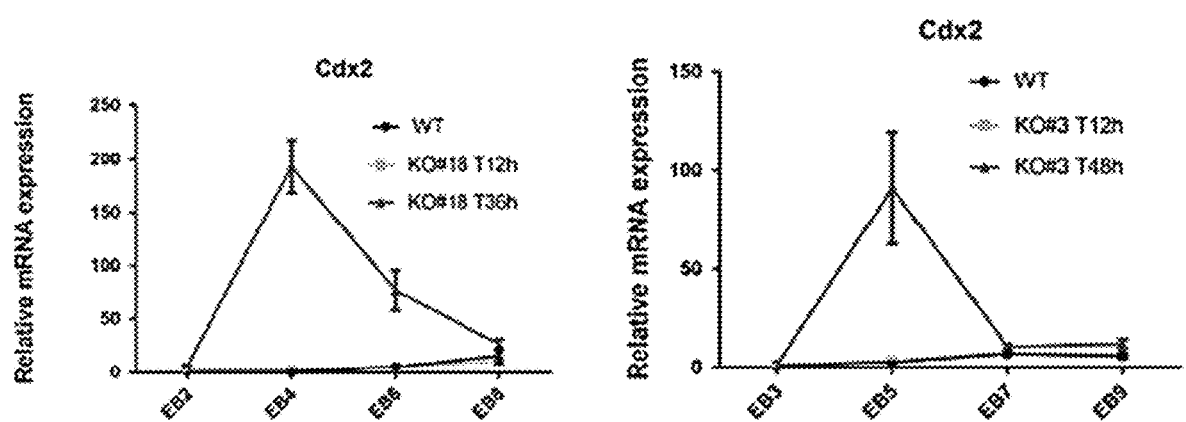
Figure 10Q:
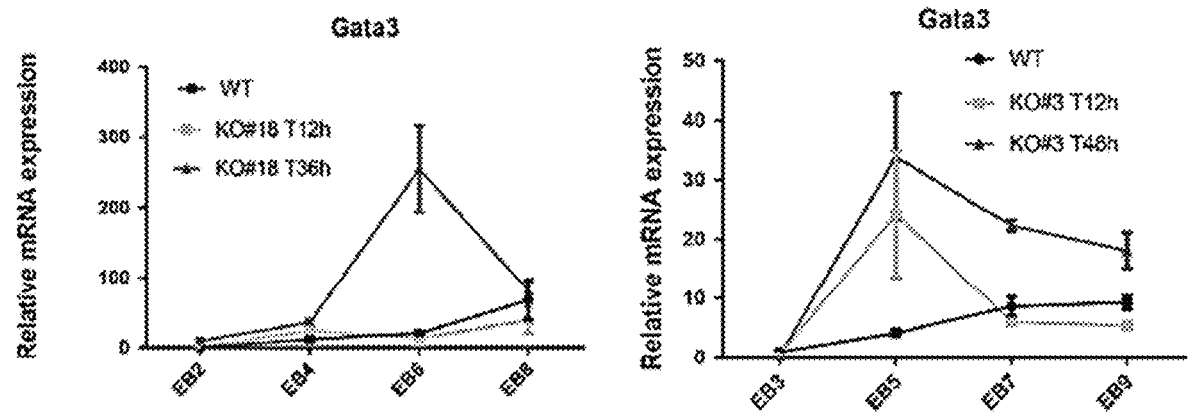

Having established a temporal-specific role for WDR5 in regulating retinal neuroectoderm and mesoderm differentiation, experiments were carried out to test whether a significant proportion of endoderm-lineage cells emerge in a WDR5-regulated manner. Analysis of RNA-Seq data indicated that transcripts associated with endoderm (Gata4 and Gata6) and trophectoderm (Cdx2 and Gata3) differentiation were upregulated in T48h group to a greater degree than in WT and T12 conditions (data not shown). RT-qPCR analysis revealed that Gata4 peaked ~30 fold at EB day 6 to 7 in T36h or T48h group, while WT and T12h groups had no significant induction of Gata4 during 8-9 days of EB differentiation (FIG. 10N). However, WDR5-dependent regulation of the endoderm marker Foxa2 or its significant upregulation was not found in the culture conditions used (FIG. 10O), suggesting that Gata4(+) upregulation without Foxa2 induction could represent formation of lateral mesoderm (Rojas et al., 2005). Interestingly, trophectoderm markers Cdx2 or Gata3 mRNA were transiently induced about 100-200-fold in T36h or T48h group, but not in WT and T12h controls (FIG. 10 P-Q). These results are consistent with a previous report (Ang et al., 2011). Collectively, the data indicate that mesoderm lineage cells, such as cardiomyocytes, are the predominant cell type that form from hWDR5$^{Dox}$;mWdr5$^{KO}$ organoids during late induction of hWDR5 in retinal culture conditions.

Example 6—WDR5 Regulates Overlapping and Distinct Direct Target Genes Associated with Retinal Neuroectoderm and Cardiac Mesodermal Fate Choice After establishing that WDR5 plays a temporal role in regulating differentiation of ESC toward retinal neuroectoderm versus cardiac mesoderm, experiments were undertaken to identify the direct genetic targets of WDR5 that may contribute to its underlying activity on influencing ESC fate choice. ChIP-Seq with an anti-HA antibody was used to identify HA-hWDR5 DNA binding sites in hWDR5$^{Dox}$; mWdr5$^{KO}$ organoids under T12h and T48h conditions (EB day 6). As set out above, T12h conditions favor ESC differentiation toward a relatively homogenous population of retinal neuroectoderm [80% Rx-GFP (+) RLCs, FIG. 2F], while T48h conditions coax a mixed population of cells, which contain cardiac lineage cell-enriched mesoderm (FIG. 4F-G).

Figure 5A:
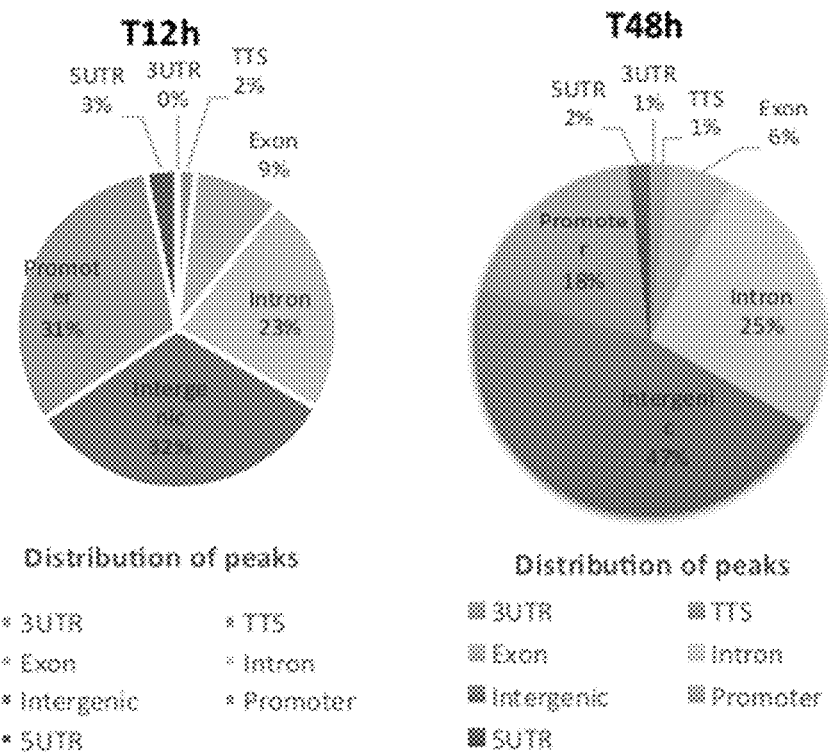
FIGS. 5A-5E. WDR5 regulates overlapping and distinct direct target genes linked to retinal neuroectoderm and cardiac mesodermal fate choice.
Figure 5B:
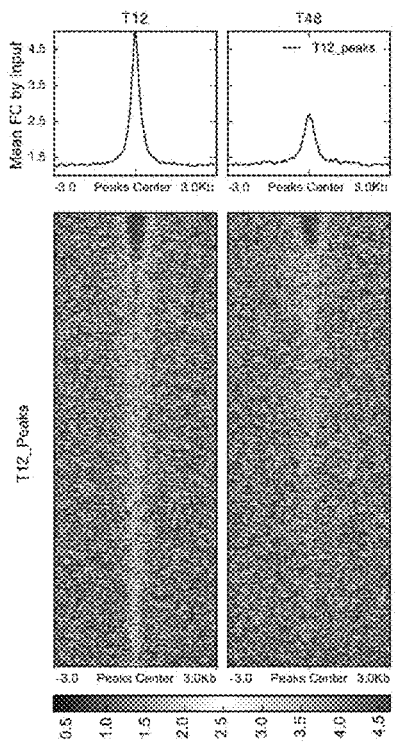
Figure 5C:
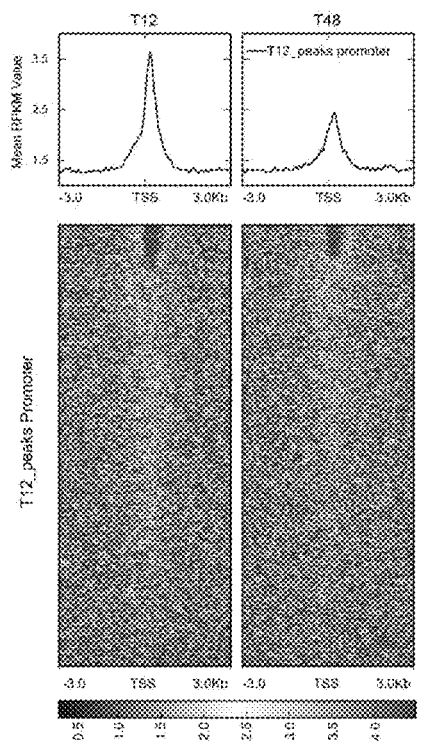

It was discovered that in T12h retinal neuroectoderm, HA-hWDR5 largely bound intergenic (32%) and promoter (31%) regions, as well as introns (23%) and exons (9%). Fewer than 5% of HA-hWDR5 binding sites were observed at 5' and 3'UTRs and transcription termination sites (TTS) (FIG. 5A). In T48h organoids, which contain cardiac lineage cells and other cell types, HA-hWDR5 binding at intergenic sites was most common (47%), followed by promoter (18%), intron (25%), exon (6%) and less than 5% binding at 5' and 3'UTRs and TTS (FIG. 5A). Analyses of HA-hWDR5-bound peak centers (FIG. 5B) and promoters (FIG. 5C) from ChIP-Seq indicate that WDR5 genomic targets in T12h and T48h groups were dynamic and T48h peaks partially overlapped with T12h. Motif analysis of HA-hWDR5-bound targets in T12h conditions revealed de novo DNA binding sequences (FIG. 5F). The top, co-occurring motif associated with WDR5 binding in T12h conditions was c-MYC. Interestingly, this consensus sequence, i.e., CACGTG, comprises the same E-box motif enriched at MYC and WDR5 binding sites in human embryonic kidney cells (293T cells) (Thomas et al., 2015b).

Figure 5D:
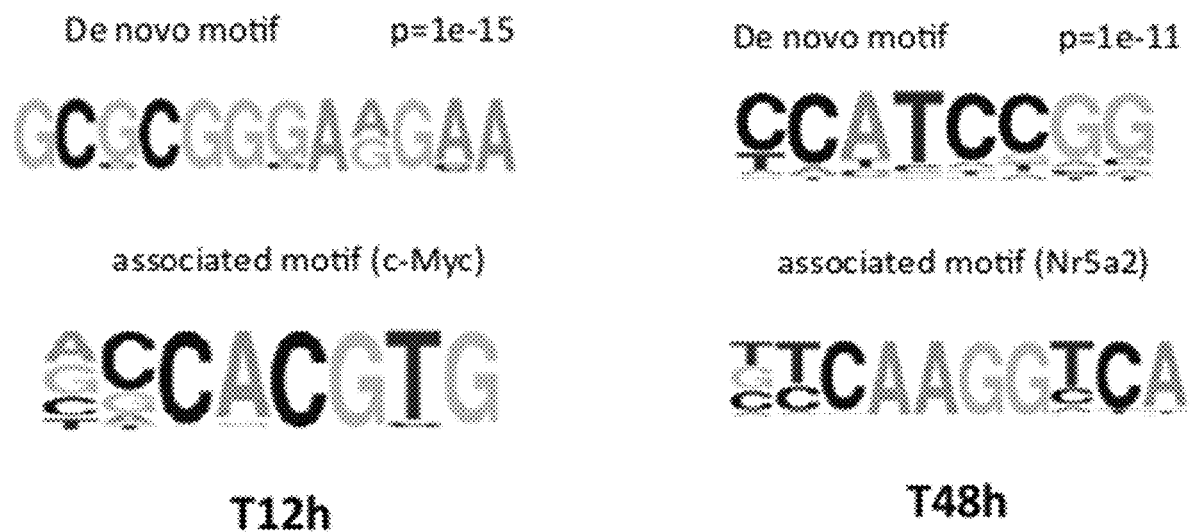
Figure 5E:
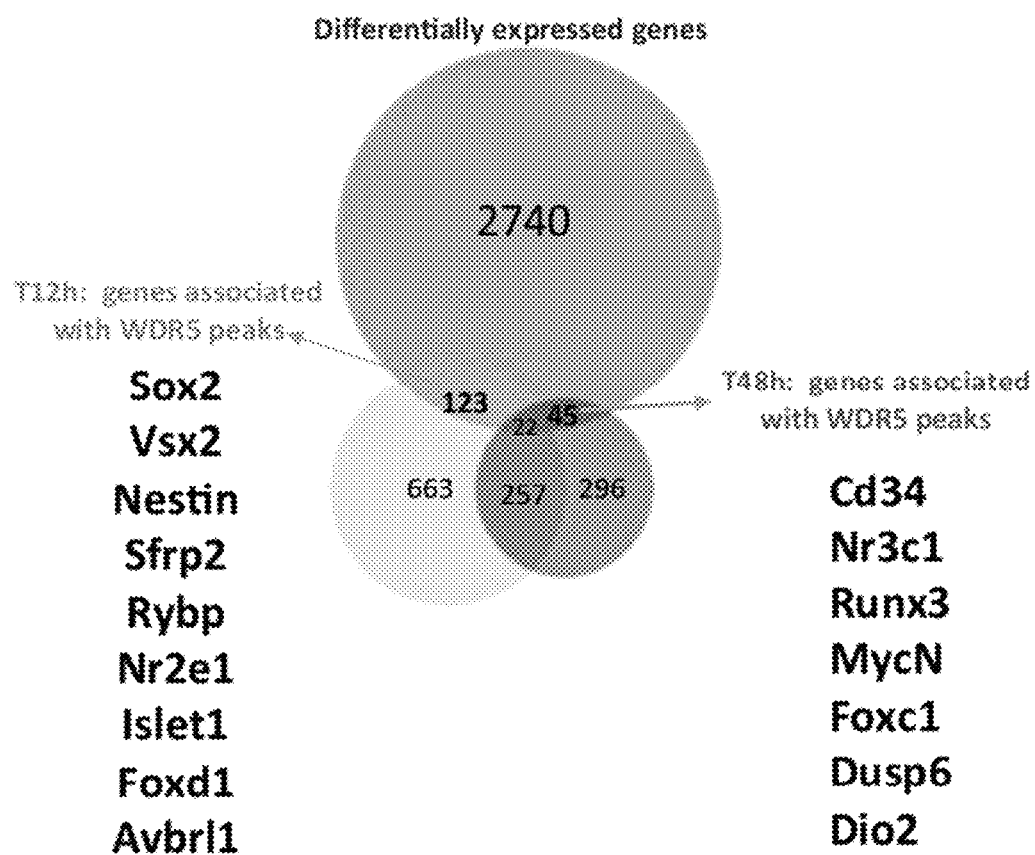

In T48h conditions, WDR5 binding was associated with a de novo motif that was distinct from that identified in T12h conditions (FIG. 5D). In T48h conditions, WDR5-bound motifs overlapped most closely with Nr5a2 consensus sequences (FIG. 5G). ChIP-Seq and RNA-Seq datasets from T12h and T48h conditions were integrated to identify potential WDR5 direct target genes, i.e. HA-hWDR5-bound genomic targets (ChIP-seq), that were associated with at least a 2-fold differential expression of corresponding transcripts (RNA-Seq). Of 123 WDR5-direct target genes in the T12h conditions, and 45 genes in T48h conditions, it was found that 22 genes overlapped in both conditions (FIG. 5H). Genes essential for retinal neuroectodermal differentiation, such as Sox2, Chx10/Vsx2, Nestin, Sfrp2, Rybp, Nr2e1, Islet1, Foxd1 and Avbrl1, were direct WDR5-target genes in T12h conditions. Cd34, Nr3c1, Runx3, MycN, Foxc1, Dusp6 and Dio2 were among the 45 direct target genes in T48h conditions. WDR5-direct target genes shared in both T12h and T48h conditions included Efcab12, Esrrb, Pou3f2/Brn2, and ribosome related genes (Rpl and Rps family).

Collectively, these data demonstrate that WDR5 regulates overlapping and distinct direct target genes, which may contribute to distinct transcriptional outputs that lead to neuroectoderm versus mesoderm fates.

Figure 6A:
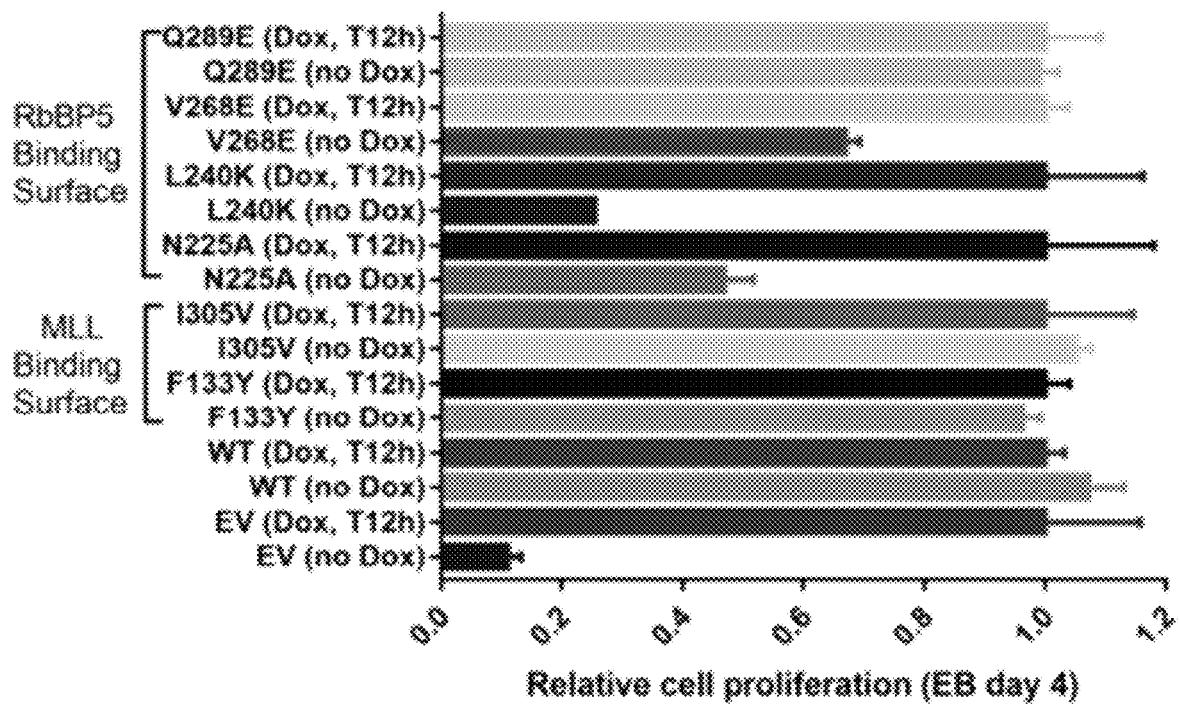
FIGS. 6A-6E. Inhibition of the WDR5-RBBP5 interaction reduces retinal lineage cell differentiation.
Figure 6B:
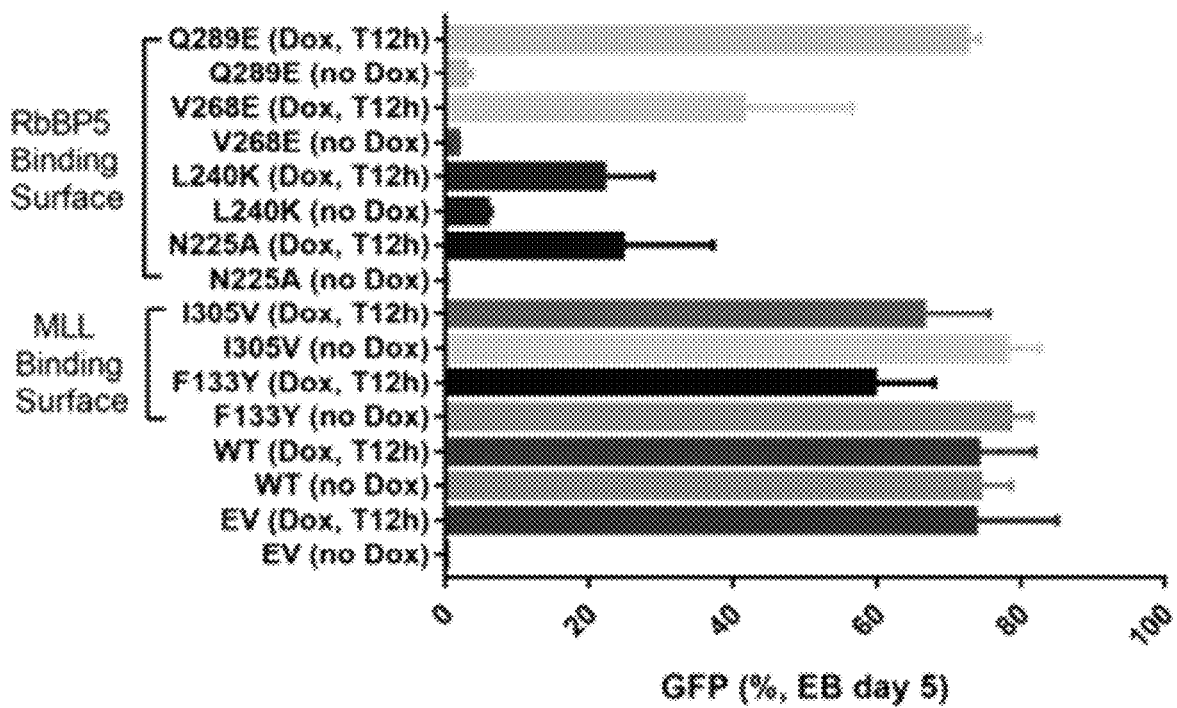
Figure 6C:
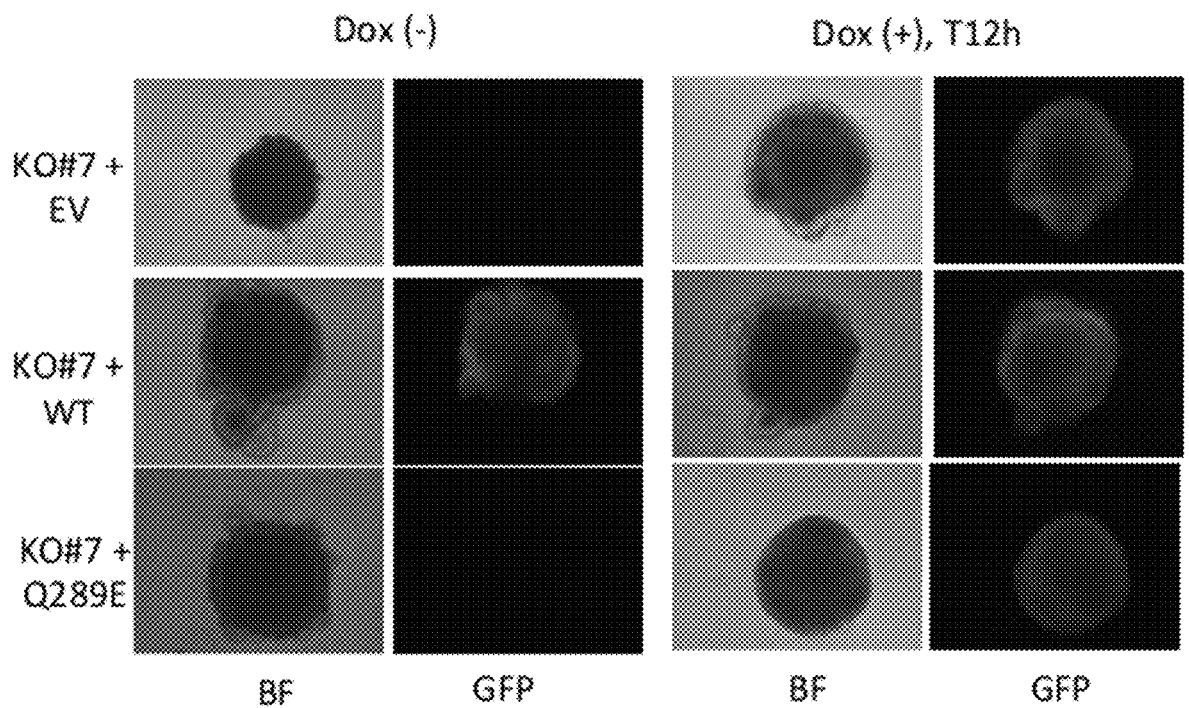
Figure 6D:
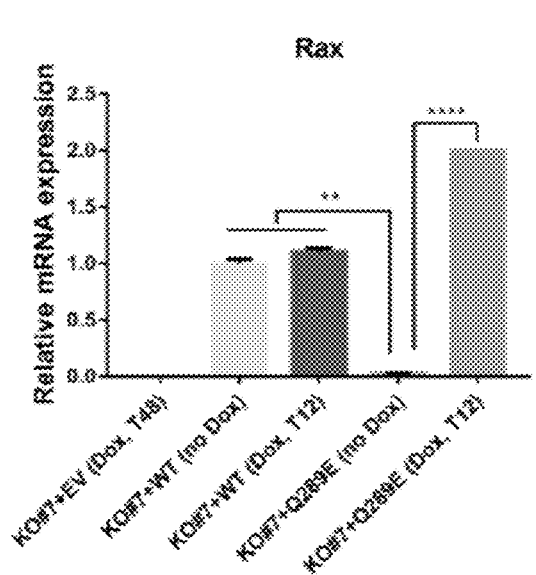
Figure 11A:
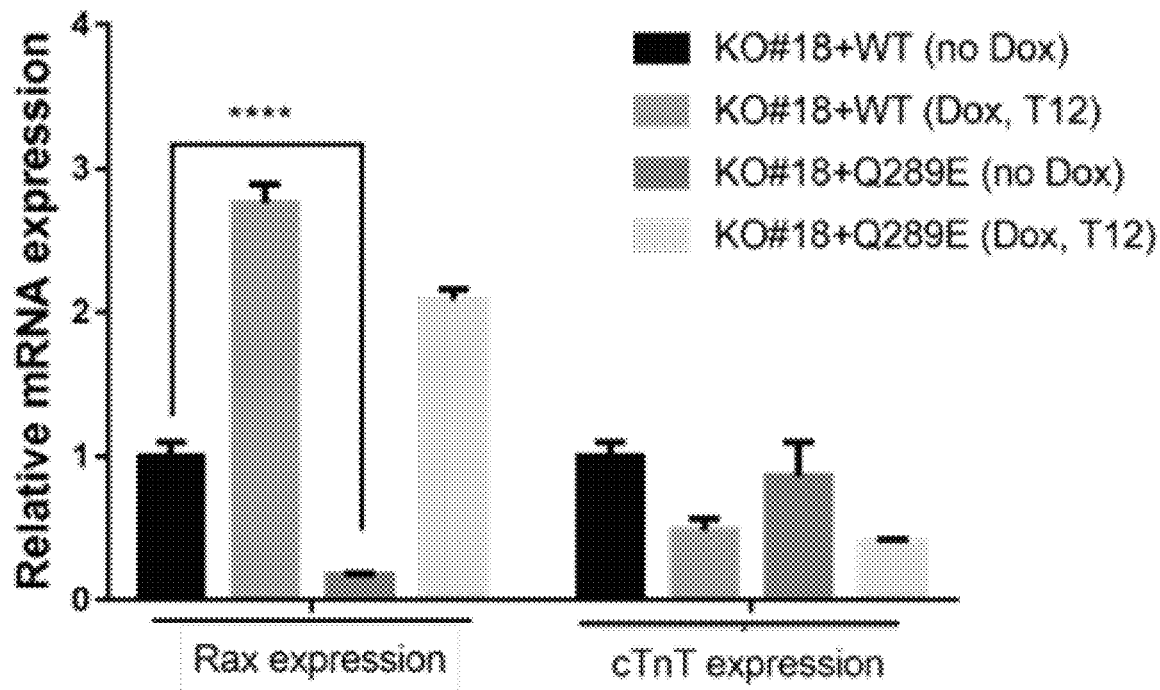
FIGS. 11A-11C. hWDR5 induction following expression of WDR5-RBBP5 binding mutants partially rescues impaired retinal neuroectoderm differentiation in hwDR5$^{Dox}$;mwdr5$^{KO}$ KO EBs.
Figure 11B:
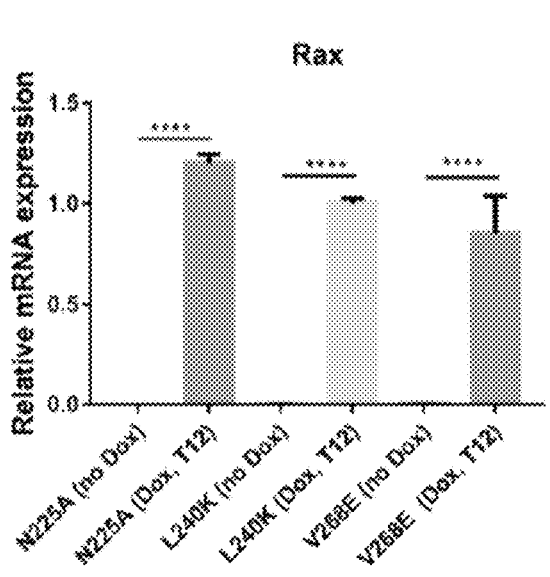

Example 7—a Critical WDR5-RbBP5 Interaction Surface Mediates ESC Differentiation Toward the Retinal Neuroectoderm Fate Because E-box motifs focus WDR5 and Myc proteins to common genomic targets in RxGFP(+) RLCs in T12h culture conditions, and since WDR5 harbors a common binding surface (typically named as RBBP5 binding surface) through which it directly interacts with RBBP5, MYC and KANSL2 through protein-protein interactions, experiments were carried out to determine whether retinal neuroectoderm differentiation is regulated by this unique WDR5 binding surface (Odho et al., 2010; Thomas et al., 2015b). To this end, hWDR5$^{Dox}$;mwdr5$^{KO}$ ESC lines, which constitutively express hWDR5 interaction mutants (Mut) that disrupt WDR5 binding with RBBP5, MYC, and/or KANSL2; i.e., hWDR5$^{Mut}$; hwDR5$^{Dox}$;mwdr5$^{KO}$ ESCs, were generated.

hWDR5$^{Mut}$; hwDR5$^{Dox}$;mwdr5$^{KO}$ organoids expressing hWDR5$^{N225A}$, hwDR5$^{L240K}$; or hWDR5$^{V268E}$ in retinal differentiation culture conditions showed impaired proliferation, when compared to control ESC-derived organoids expressing either inducible hWDR5 (+Dox) or constitutive hWDR5 expression (−Dox) (FIG. 6A). Interestingly, hWDR5$^{Q289E}$ expressing differentiating organoids demonstrated similar levels of proliferation as control organoids (FIG. 6A). In addition to the observed proliferation defects, hWDR5$^{Mut}$; hWDR5$^{Dox}$; mWdr5$^{KO}$ organoids expressing hWDR5$^{N225A}$, hWDR5$^{L240K}$, or hWDR5$^{V268E}$ showed defective Rx-GFP (+) RLC differentiation (FIG. 6B). The impaired retinal differentiation could not be fully rescued with inducible WT hWDR5 (+Dox at T12h) indicating a dominant negative effect of these mutants. Unlike the other mutants, defective retinal differentiation in hWDR5$^{Q289E}$-expressing organoids could be fully rescued with inducible WT hWDR5 (+Dox at T12h), which indicated that this mutant does not act in a dominant negative fashion (FIG. 6B-C). RT-qPCR analyses further supported the hWDR5$^{Mut}$ findings above (FIG. 6D, FIG. 11A-B). In contrast, hWDR5$^{Mut}$; hwDR5$^{Dox}$; mWdr5$^{KO}$ organoids expressing hWDR5 forms which contain mutations in the Win-motif, and as a result cannot bind MII1 (i.e., hWDR5$^{F133Y}$ or hWDR5$^{B305V}$) did not harbor defects in proliferation or RLC differentiation (FIG. 6A-B). These data indicate that the WDR5-RBBP5, WDR5-MYC, and/or WDR5-KANSL2 interaction surface is essential for proper retinal neuroectoderm differentiation, and that the WDR5-MLL1 interaction is dispensable in this context.

Figure 6E:
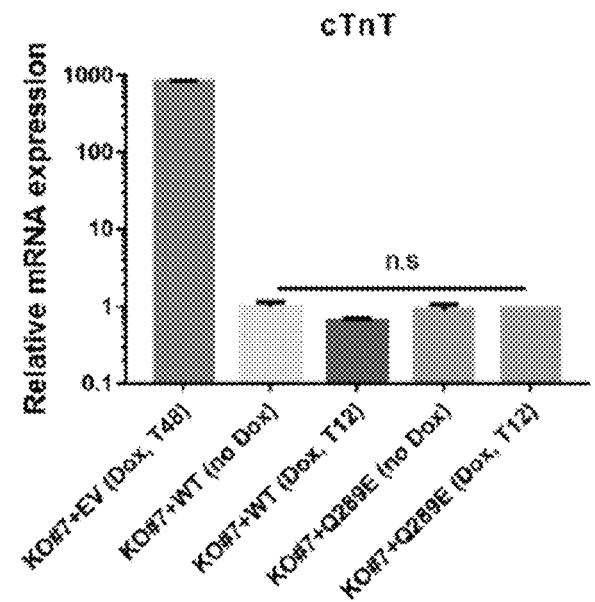
Figure 11C:
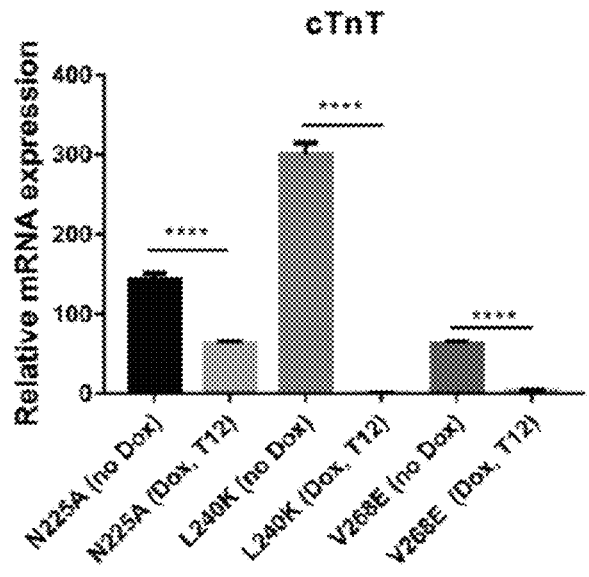

Given earlier results, which showed that late WT hWDR5 induction led to a switch of ESC differentiation from retinal neuroectoderm to cardiac mesoderm-enriched tissues, experiments were carried out to determine whether disruption of the WDR5-RBBP5, WDR5-MYC, and/or WDR5-KANSL2 interaction surface might mechanistically contribute to this effect. Indeed, it was found that hWDR5$^{Mut}$; hwDR5$^{Dox}$; mWDR5$^{KO}$ organoids expressing hWDR5$^{N225A}$, hWDR5$^{L240K}$, or hWDR5$^{V268E}$ showed increased cardiomyocyte-specific cTnT expression (FIG. 11C); and the resulting organoids spontaneously contracted. cTnT was reduced, and RLC-specific Rx/Rax expression increased by "rescue" of these hwDR5$^{Mut}$; hwDR5$^{Dox}$; mWdr5$^{KO}$ organoids with inducible hWDR5 (+Dox at T12h) (FIG. 11B-C). In these unique, mixed tissue-organoids, retinal neuroectoderm emerged opposite contractile cardiomyocyte mesoderm. Thus, these organoids comprised both retinal lineage cells and cardiac lineage cells. Similarly, reintroduction of inducible hWDR5 (+Dox at T12h) in two independent hWDR5$^{Q289E}$; hWDR5$^{Dox}$;mwdr5$^{KO}$ organoids restored Rx/Rax expression (FIG. 6D, FIG. 11A). It was observed, however, that cardiac mesoderm differentiation is not simply a "default" consequence arising from disruption of the WDR5-RBBP5, WDR5-MYC, and/or WDR5-KANSL2 interaction surface, as hWDR5$^{Q289E}$; hwDR5$^{Dox}$; mwdr5$^{KO}$ organoids became neither Rx/Rax(+) retinal neuroectoderm nor cTnT+ cardiac mesoderm (FIG. 6D-E; FIG. 11A).

These data indicate that the WDR5-RBBP5, WDR5-MYC, and/or WDR5-KANSL2 interaction surface potently drives retinal neuroectoderm differentiation, and to a limited extent, inhibits cardiac mesoderm formation.

Collectively, these studies establish a novel role for WDR5 in regulating neuroectoderm and mesoderm cell fate determination. WDR5 acts as a "temporal rheostat" that controls cell fate: when unperturbed or overexpressed, WDR5 promotes cell proliferation and retinal neuroectoderm formation. As this rheostat is adjusted by transient suppression of WDR5 for 36-48h, and then toggled by re-expression of WDR5, retinal neuroectoderm conversion is blocked. Instead, differentiation skews toward mesoderm differentiation, as noted by formation of contractile cardiomyocytes. Mechanistically, this rheostat function depends on a protein-protein interaction between WDR5 and RBBP5, WDR5 and MYC, and/or WDR5 and KANSL2.

These experiments define a direct, causal, and temporal role for WDR5 in cell fate determination of retinal neuroectoderm and mesoderm differentiation, even in neuroectoderm-permissive culture conditions. In suspension culture of ESC-derived EB (organoid) aggregates without serum (SFEB method), neuroectoderm forms largely without concomitant induction of mesoderm and endoderm tissues (Watanabe et al., 2005). Using this culture system, it was found that WDR5 is a powerful inducer of differentiation without serum or exogenous cytokines such as BMP4, Activin A or VEGF, which are typically required to induce ESC differentiation to mesoderm (Kokkinopoulos et al., 2016).

These experiments provide foundational insights by elucidating WDR5-related motifs and genomic targets that potentially control early retinal neuroectoderm versus mesoderm differentiation. The experiments identify direct target genes, such as Sox2, Vsx2, Nestin and Sfrp2 (Gonzalez-Rodriguez et al., 2010), known to play classic roles during retinogenesis but were previously not known to interact with WDR5. WDR5 targets the epigenetic regulator Rybp (Ring1 and Yy1 Binding Protein), which is essential for neural differentiation from ESCs, as well as retinal development in vivo (Kovacs et al., 2016; Pirity et al., 2007). Rybp controls H2AK119 mono-ubiquitylation at polycomb (PcG) group targets in mESCs (Rose et al., 2016).

ChIP-Seq of ESC-derived retinal neuroectoderm revealed that WDR5 preferentially binds canonical sequences shared by Myc, i.e. E-box motifs. That Myc and WDR5 share genomic targets in the genome of ESC-derived RLCs is consistent with the recent report that demonstrated recruitment of WDR5 and Myc to particular genes that control a variety of biological processes, including tumorigenesis (Dingar et al., 2015; Thomas et al., 2015b).

During WDR5-mediated formation of mesoderm, it was found that WDR5 preferentially binds a consensus motif shared with the nuclear receptor Nr5a2. Indeed, mesoderm fails to form in mice with Nr5a2 deletion (Labelle-Dumais et al., 2006).

It also was uncovered herein that WDR5-RBBP5, WDR5-MYC, and/or WDR5-KANSL2 protein-protein interaction controls retinal neuroectoderm differentiation. Within WDR5, L240 and N225 form polar contacts with RBBP5, MYC, and/or KANSL2, and residues at Q289 and V268 mediate hydrophobic interactions with RBBP5, MYC, and/or KANSL2. By reconstitution of WDR5 with RBBP5, MYC, and/or KANSL2 binding mutants, the specific residues at these interaction surfaces that are required for proper retinal neuroectoderm differentiation were identified. The functional significance imparted by the WDR5-RBBP5, WDR5-MYC, and/or WDR5-KANSL2 interaction in cell fate determination is supported by the fact that shRNA-mediated RBBP5 depletion impairs ESC-to-neuroectoderm formation in both monolayer and (EB) suspension cultures containing retinoic acid (Jiang et al., 2011).

Experimental results show that ubiquitously expressed proteins like WDR5 harbor temporal and tissue-specific functions and function as rheostats of cell fate. The disclosure shows that stem cell-derived, organoid-based complementation system combines CRISPR/Cas9-based editing with inducible genetic rescue and uncouples basal functions like cell survival from temporal and tissue-specific roles in ubiquitous proteins like WDR5. When combined with genome-wide analyses, identification of de novo and transcription factor-associated motifs (FIG. 5D) offer fundamental insights into how broadly expressed proteins temporally tailor their activities based on cell type.

The disclosure provides experimental methods and cells which may provide insights into human developmental disorders. For instance, the microphthalmia-related conditions, CHARGE and Kabuki Syndromes, are caused by mutations in CHD7 and KMT2D, respectively. Both CHD7 and KMT2D interact with WDR5 and RBBP5 (Schulz et al., 2014). CHARGE syndrome also features cardiac defects, and recently, a de novo mutation in WDR5 (p.Lys7G1n) has also been linked to a variety of human congenital heart diseases (Zaidi et al., 2013). The methods and cells described herein could be used to interrogate the role of the WDR5-RBBP5, WDR5-MYC, and/or WDR5-KANSL2 interaction in microphthalmia and congenital heart diseases and syndromes using both mouse and human ESC-based models.

The disclosure elucidates a targetable protein-protein interface that can modulate ESC fate from retinal neuroectoderm to mesoderm. This platform could be used to better characterize a poorly understood, unique cell type, the bipotent neuro-mesoderm progenitor (NMP). The disclosure shows that constitutive expression of hWDR5 mutants that abrogate WDR5-RBBP5, WDR5-MYC, and/or WDR5-KANSL2 binding, followed by upregulation of hWDR5, to led ESC-derived, single, mixed organoids in which Rx+ RLC retinal neuroepithelium forms in one region and cardiomyocytes contract in another. Indeed, single cell RNA-seq of 6-month old, ESC-derived human neuroectoderm organoids cultured in serum-free conditions revealed the presence of both retinal and mesodermal precursors (Quadrato et al., 2017).

Sox2(+) Brachyury(+) double positive cells are NMPs, and coordinate Sox2 and Brachyury activity controls NMP differentiation toward both spinal cord and paraxial skeletal musculature fates (Koch et al., 2017). We observed induction of both Sox2 and Brachyury at day 3 in T48 conditions, but not in WT and T12 conditions. (FIG. 10K-L). Single-cell analyses of T48h or mixed organoids containing Sox2 and Brachyury-reporter cells may shed light on NMP differentiation and whether they may contribute to CNS tissues beyond the spinal cord, such as Rx+ RLCs. Additionally, the WDR5-RBBP5, WDR5-MYC, and/or WDR5-KANSL2 interaction can be exploited to deterministically generate retinal neuroectoderm and contractile cardiomyocytes within a single organoid. This disclosure provides an initial step toward future generation of more mature organoids with decreased hypoxia-related cell death. The disclosure provides experimental evidence that the WDR5-RBBP5, WDR5-MYC, and/or WDR5-KANSL2 interface is highly amenable for small molecule modulation that is useful for stem cell and organoid-based research and regenerative medicine applications.

The disclosure has described various embodiments found or proposed to comprise specific modes for the practice of the invention. Various modifications and variations of the described disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the methods of the disclosure that are obvious to those skilled in the relevant fields are intended to be within the scope of the following claims.

The disclosure has described various amino acid and nucleic acid sequences, which are provided herein below in Table 2.

TABLE 2

SEQUENCE TABLE

| SEQ ID NO: | SEQUENCE |
|---|---|
| 1-wt WDR5 amino acid sequence | MATEEKKPETEAARAQPTPSSSATQSKPTPVKPNYALKFTLAGHTKAVSSVKFSPNGEWLASSSADKLIKIWGA YDGKFEKTISGHKLGISDVAWSSDSNLLVSASDDKTLKIWDVSSGKCLKTLKGHSNYVFCCNFNPQSNLIVSGS FDESVRIWDVKTGKCLKTLPAHSDPVSAVHFNRDGSLIVSSSYDGLCRIWDTASGQCLKTLIDDDNPPVSFVKF SPNGKYILAATLDNTLKLWDYSKGKCLKTYTGHKNEKYCIFANFSVTGGKWIVSGSEDNLVYIWNLQTKEIVQK LQGHTDVVISTACHPTENIIASAALENDKTIKLWKSDC |
| 2 | DDLDVV |
| 3 | LDVV |
| 4 | EEVDVT |
| 5 | EVDVT |
| 6 | VDVT |
| 7 | EEIDVV |
| 8 | IDVV |
| 9-wt WDR5 nucleotide sequence | atggcgacggaggagaagaagcccgagaccgaggccgccagagcacagccaaccccttcgtcatccgccactca gagcaagcctacacctgtgaagccaaactatgctctaaagttcacccttgctggccacaccaaagcagtgtcct ccgtgaaattcagcccgaatggagagtggctggcaagttcatctgctgataaacttattaaaatttggggcgcg tatgatgggaaatttgagaaaaccatatctggtcacaagctgggaatatccgatgtagcctggtcgtcagattc taaccttcttgtttctgcctcagatgacaaaaccttgaagatatgggacgtgagctcgggcaagtgtctgaaaa ccctgaagggacacagtaattatgtcttttgctgcaacttcaatccccagtccaaccttattgtctcaggatcc tttgacgaaagcgtgaggatatgggatgtgaaaacagggaagtgcctcaagactttgccagctcactcggatcc agtctcggccgttcatttaatcgtgatggatccttgatagtttcaagtagctatgatggtctctgtcgcatct gggacaccgcctcaggccagtgcctgaagacgctcatcgatgacgacaaccccccgtgtcttttgtgaagttc tccccgaacggcaaatacatcctggccgccacgctggacaacactctgaagctctgggactacagcaaggggaa gtgcctgaagacgtacactggccacaagaatgagaaatactgcatatttgccaatttctctgttactggtggga agtggattgtgtctggctcagaggataaccttgtttacatctggaaccttcagacgaaagagattgtacagaaa ctacaaggccacacagatgtcgtgatctcaacagcttgtcacccaacagaaaacatcatcgcctctgctgcgct agaaaatgacaaaacaattaaactgtggaagagtgactgctaa |
| 10-WDR5 mutant F133Y | atggcgacggaggagaagaagcccgagaccgaggccgccagagcacagccaaccccttcgtcatccgccactca gagcaagcctacacctgtgaagccaaactatgctctaaagttcacccttgctggccacaccaaagcagtgtcct ccgtgaaattcagcccgaatggagagtggctggcaagttcatctgctgataaacttattaaaatttggggcgcg tatgatgggaaatttgagaaaaccatatctggtcacaagctgggaatatccgatgtagcctggtcgtcagattc taaccttcttgtttctgcctcagatgacaaaaccttgaagatatgggacgtgagctcgggcaagtgtctgaaaa ccctgaagggacacagtaattatgtcttttgctgcaacttcaatccccagtccaaccttattgtctcaggatcc tttgacgaaagcgtgaggatatgggatgtgaaaacagggaagtgcctcaagactttgccagctcactcggatcc agtctcggccgttcatttaatcgtgatggatccttgatagtttcaagtagctatgatggtctctgtcgcatct gggacaccgcctcaggccagtgcctgaagacgctcatcgatgacgacaaccccccgtgtcttttgtgaagttc tccccgaacggcaaatacatcctggccgccacgctggacaacactctgaagctctgggactacagcaaggggaa gtgcctgaagacgtacactggccacaagaatgagaaatactgcatatttgccaatttctctgttactggtggga agtggattgtgtctggctcagaggataaccttgtttacatctggaaccttgagacgaaagagattgtacagaaa ctacaaggccacacagatgtcgtgatctcaacagcttgtcacccaacagaaaacatcatcgcctctgctgcgct agaaaatgacaaaacaattaaactgtggaagagtgactgctaa |
| 11- WDR5 mutant N225A | atggcgacggaggagaagaagcccgagaccgaggccgccagagcacagccaaccccttcgtcatccgccactca gagcaagcctacacctgtgaagccaaactatgctctaaagttcacccttgctggccacaccaaagcagtgtcct ccgtgaaattcagcccgaatggagagtggctggcaagttcatctgctgataaacttattaaaatttggggcgcg tatgatgggaaatttgagaaaaccatatctggtcacaagctgggaatatccgatgtagcctggtcgtcagattc taaccttcttgtttctgcctcagatgacaaaaccttgaagatatgggacgtgagctcgggcaagtgtctgaaaa ccctgaagggacacagtaattatgtcttttgctgcaacttcaatccccagtccaaccttattgtctcaggatcc tttgacgaaagcgtgaggatatgggatgtgaaaacagggaagtgcctcaagactttgccagctcactcggatcc agtctcggccgttcatttaatcgtgatggatccttgatagtttcaagtagctatgatggtctctgtcgcatct gggacaccgcctcaggccagtgcctgaagacgctcatcgatgacgacaaccccccgtgtcttttgtgaagttc tcccctgcaggcaaatacatcctggccgccacgctggacaacactctgaagctctgggactacagcaaggggaa |

TABLE 2-continued

SEQUENCE TABLE

| SEQ ID NO: | SEQUENCE |
|---|---|
| | gtgcctgaagacgtacactggccacaagaatgagaaatactgcatatttgccaatttctctgttactggtggga agtggattgtgtctggctcagaggataaccttgtttacatctggaaccttcagacgaaagagattgtacagaaa ctacaaggccacacagatgtcgtgatctcaacagcttgtcacccaacagaaaacatcatcgcctctgctgcgct agaaaatgacaaaacaattaaactgtggaagagtgactgctaa |
| 12-WDR5 mutant L240K | atggcgacggaggagaagaagcccgagaccgaggccgccagagcacagccaaccccttcgtcatccgccactca gagcaagcctacacctgtgaagccaaactatgctctaaagttcacccttgctggccacaccaaagcagtgtcct ccgtgaaattcagcccgaatggagagtggctggcaagttcatctgctgataaacttattaaaatttggggcgcg tatgatgggaaatttgagaaaaccatatctggtcacaagctgggaatatccgatgtagcctggtcgtcagattc taaccttcttgtttctgcctcagatgacaaaaccttgaagatatgggacgtgagctcgggcaagtgtctgaaaa ccctgaagggacacagtaattatgtctttgctgcaacttcaatccccagtccaaccttattgtctcaggatcc tttgacgaaagcgtgaggatatgggatgtgaaaacagggaagtgcctcaagactttgccagctcactcggatcc agtctcggccgttcattttaatcgtgatggatccttgatagtttcaagtagctatgatggtctctgtcgcatct gggacaccgcctcaggccagtgcctgaagacgctcatcgatgacgacaaccccccgtgtcttttgtgaagttc tccccgaacggcaaatacatcctggccgccacgctggacaacactctgaagaaatgggactacagcaaggggaa gtgcctgaagacgtacactggccacaagaatgagaaatactgcatatttgccaatttctctgttactggtggga agtggattgtgtctggctcagaggataaccttgtttacatctggaaccttcagacgaaagagattgtacagaaa ctacaaggccacacagatgtcgtgatctcaacagcttgtcacccaacagaaaacatcatcgcctctgctgcgct agaaaatgacaaaacaattaaactgtggaagagtgactgctaa |
| 13-WDR5 mutant V268E | atggcgacggaggagaagaagcccgagaccgaggccgccagagcacagccaaccccttcgtcatccgccactca gagcaagcctacacctgtgaagccaaactatgctctaaagttcacccttgctggccacaccaaagcagtgtcct ccgtgaaattcagcccgaatggagagtggctggcaagttcatctgctgataaacttattaaaatttggggcgcg tatgatgggaaatttgagaaaaccatatctggtcacaagctgggaatatccgatgtagcctggtcgtcagattc taaccttcttgtttctgcctcagatgacaaaaccttgaagatatgggacgtgagctcgggcaagtgtctgaaaa ccctgaagggacacagtaattatgtctttgctgcaacttcaatccccagtccaaccttattgtctcaggatcc tttgacgaaagcgtgaggatatgggatgtgaaaacagggaagtgcctcaagactttgccagctcactcggatcc agtctcggccgttcattttaatcgtgatggatccttgatagtttcaagtagctatgatggtctctgtcgcatct gggacaccgcctcaggccagtgcctgaagacgctcatcgatgacgacaaccccccgtgtcttttgtgaagttc tccccgaacggcaaatacatcctggccgccacgctggacaacactctgaagctctgggactacagcaaggggaa gtgcctgaagacgtacactggccacaagaatgagaaatactgcatatttgccaatttctctgaaccggtggga agtggattgtgtctggctcagaggataaccttgtttacatctggaaccttcagacgaaagagattgtacagaaa ctacaaggccacacagatgtcgtgatctcaacagcttgtcacccaacagaaaacatcatcgcctctgctgcgct agaaaatgacaaaacaattaaactgtggaagagtgactgctaa |
| 14-WDR5 mutant Q289E | atggcgacggaggagaagaagcccgagaccgaggccgccagagcacagccaaccccttcgtcatccgccactca gagcaagcctacacctgtgaagccaaactatgctctaaagttcacccttgctggccacaccaaagcagtgtcct ccgtgaaattcagcccgaatggagagtggctggcaagttcatctgctgataaacttattaaaatttggggcgcg tatgatgggaaatttgagaaaaccatatctggtcacaagctgggaatatccgatgtagcctggtcgtcagattc taaccttcttgtttctgcctcagatgacaaaaccttgaagatatgggacgtgagctcgggcaagtgtctgaaaa ccctgaagggacacagtaattatgtctttgctgcaacttcaatccccagtccaaccttattgtctcaggatcc tttgacgaaagcgtgaggatatgggatgtgaaaacagggaagtgcctcaagactttgccagctcactcggatcc agtctcggccgttcattttaatcgtgatggatccttgatagtttcaagtagctatgatggtctctgtcgcatct gggacaccgcctcaggccagtgcctgaagacgctcatcgatgacgacaaccccccgtgtcttttgtgaagttc tccccgaacggcaaatacatcctggccgccacgctggacaacactctgaagctctgggactacagcaaggggaa gtgcctgaagacgtacactggccacaagaatgagaaatactgcatatttgccaatttctctgttactggtggga agtggattgtgtctggctcagaggataaccttgtttacatctggaaccttcagacgaaagagattgtacagaaa ctacaaggccacacagatgtcgtggtctcaacagcttgtcacccaacagaaaacatcatcgcctctgctgcgct agaaaatgacaaaacaattaaactgtggaagagtgactgctaa |
| 15-WDR5 mutant I305V | atggcgacggaggagaagaagcccgagaccgaggccgccagagcacagccaaccccttcgtcatccgccactca gagcaagcctacacctgtgaagccaaactatgctctaaagttcacccttgctggccacaccaaagcagtgtcct ccgtgaaattcagcccgaatggagagtggctggcaagttcatctgctgataaacttattaaaatttggggcgcg tatgatgggaaatttgagaaaaccatatctggtcacaagctgggaatatccgatgtagcctggtcgtcagattc taaccttcttgtttctgcctcagatgacaaaaccttgaagatatgggacgtgagctcgggcaagtgtctgaaaa ccctgaagggacacagtaattatgtctttgctgcaacttcaatccccagtccaaccttattgtctcaggatcc tttgacgaaagcgtgaggatatgggatgtgaaaacagggaagtgcctcaagactttgccagctcactcggatcc agtctcggccgttcattttaatcgtgatggatccttgatagtttcaagtagctatgatggtctctgtcgcatct gggacaccgcctcaggccagtgcctgaagacgctcatcgatgacgacaaccccccgtgtcttttgtgaagttc tccccgaacggcaaatacatcctggccgccacgctggacaacactctgaagctctgggactacagcaaggggaa gtgcctgaagacgtacactggccacaagaatgagaaatactgcatatttgccaatttctctgttactggtggga agtggattgtgtctggctcagaggataaccttgtttacatctggaaccttcagacgaaagagattgtacagaaa ctacaaggccacacagatgtcgtggtctcaacagcttgtcacccaacagaaaacatcatcgcctctgctgcgct agaaaatgacaaaacaattaaactgtggaagagtgactgctaa |
| 16-mWdr5 guide RNA sequence | tgtgaagttcagcccccaatg |

REFERENCES

Ang, Y. S., Tsai, S. Y., Lee, D. F., Monk, J., Su, J., Ratnakumar, K., Ding, J., Ge, Y., Darr, H., Chang, B., et al. (2011). Wdr5 mediates self-renewal and reprogramming via the embryonic stem cell core transcriptional network. Cell 145, 183-197.

Assawachananont, J., Mandai, M., Okamoto, S., Yamada, C., Eiraku, M., Yonemura, S., Sasai, Y., and Takahashi, M. (2014). Transplantation of embryonic and induced pluripotent stem cell-derived 3D retinal sheets into retinal degenerative mice. Stem Cell Reports 2, 662-674.

Bruce, S. J., Gardiner, B. B., Burke, L. J., Gongora, M. M., Grimmond, S. M., and Perkins, A. C. (2007). Dynamic transcription programs during ES cell differentiation towards mesoderm in serum versus serum-freeBMP4 culture. BMC Genomics 8, 365.

Cao, F., Townsend, E. C., Karatas, H., Xu, J., Li, L., Lee, S., Liu, L., Chen, Y., Ouillette, P., Zhu, J., et al. (2014). Targeting MLL1 H3K4 methyltransferase activity in mixed-lineage leukemia. Mol Cell 53, 247-261.

Carugo, A., Genovese, G., Seth, S., Nezi, L., Rose, J. L., Bossi, D., Cicalese, A., Shah, P. K., Viale, A., Pettazzoni, P. F., et al. (2016). In Vivo Functional Platform Targeting Patient-Derived Xenografts Identifies WDR5-Myc Association as a Critical Determinant of Pancreatic Cancer. Cell Rep 16, 133-147.

Chantada, G. L., Qaddoumi, I., Canturk, S., Khetan, V., Ma, Z., Kimani, K., Yeniad, B., Sultan, I., Sitorus, R. S., Tacyildiz, N., et al. (2011). Strategies to manage retinoblastoma in developing countries. Pediatr Blood Cancer 56, 341-348.

Decembrini, S., Koch, U., Radtke, F., Moulin, A., and Arsenijevic, Y. (2014). Derivation of traceable and transplantable photoreceptors from mouse embryonic stem cells. Stem Cell Reports 2, 853-865.

Dias, J., Van Nguyen, N., Georgiev, P., Gaub, A., Brettschneider, J., Cusack, S., Kadlec, J., and Akhtar, A. (2014). Structural analysis of the KANSL1/WDR5/KANSL2 complex reveals that WDR5 is required for efficient assembly and chromatin targeting of the NSL complex. Genes Dev 28, 929-942.

Dingar, D., Kalkat, M., Chan, P. K., Srikumar, T., Bailey, S. D., Tu, W. B., Coyaud, E., Ponzielli, R., Kolyar, M., Jurisica, I., et al. (2015). BioID identifies novel c-MYC interacting partners in cultured cells and xenograft tumors. J Proteomics 118, 95-111.

Dou, Y., Milne, T. A., Ruthenburg, A. J., Lee, S., Lee, J. W., Verdine, G. L., Allis, C. D., and Roeder, R. G. (2006). Regulation of MLL1 H3K4 methyltransferase activity by its core components. Nat Struct Mol Biol 13, 713-719.

Dou, Y., Milne, T. A., Tackett, A. J., Smith, E. R., Fukuda, A., Wysocka, J., Allis, C. D., Chait, B. T., Hess, J. L., and Roeder, R. G. (2005). Physical association and coordinate function of the H3 K4 methyltransferase MLL1 and the H4 K16 acetyltransferase MOF. Cell 121, 873-885.

Ee, L. S., McCannell, K. N., Tang, Y., Fernandes, N., Hardy, W. R., Green, M. R., Chu, F., and Fazzio, T. G. (2017). An Embryonic Stem Cell-Specific NuRD Complex Functions through Interaction with WDR5. Stem cell reports 8, 1488-1496.

Eiraku, M., Takata, N., Ishibashi, H., Kawada, M., Sakakura, E., Okuda, S., Sekiguchi, K., Adachi, T., and Sasai, Y. (2011). Self-organizing optic-cup morphogenesis in three-dimensional culture. Nature 472, 51-56.

Gonzalez-Rodriguez, J., Pelcastre, E. L., Tovilla-Canales, J. L., Garcia-Ortiz, J. E., Amato-Almanza, M., Villanueva-Mendoza, C., Espinosa-Mattar, Z., and Zenteno, J. C. (2010). Mutational screening of CHX10, GDF6, OTX2, RAX and SOX2 genes in 50 unrelated microphthalmia-anophthalmia-coloboma (MAC) spectrum cases. Br J Ophthalmol 94, 1100-1104.

Gori, F., Friedman, L. G., and Demay, M. B. (2006). Wdr5, a WD-40 protein, regulates osteoblast differentiation during embryonic bone development. Dev Biol 295, 498-506.

Heinz S, Benner C, Spann N, Bertolino E, Lin Y C, Laslo P, Cheng J X, Murre C, Singh H, Glass C K: Simple Combinations of Lineage-Determining Transcription Factors Prime cis-Regulatory Elements Required for Macrophage and B Cell Identities. Mol Cell 2010, 38(4):576-589.

Heng, J. C., Feng, B., Han, J., Jiang, J., Kraus, P., Ng, J. H., Orlov, Y. L., Huss, M., Yang, L., Lufkin, T., et al. (2010). The nuclear receptor Nr5a2 can replace Oct4 in the reprogramming of murine somatic cells to pluripotent cells. Cell stem cell 6, 167-174.

Honda, M., Kurisaki, A., Ohnuma, K., Okochi, H., Hamazaki, T. S., and Asashima, M. (2006). N-cadherin is a useful marker for the progenitor of cardiomyocytes differentiated from mouse ES cells in serum-free condition. Biochem Biophys Res Commun 351, 877-882.

Hubert, A., Henderson, J. M., Ross, K. G., Cowles, M. W., Tones, J., and Zayas, R. M. (2013). Epigenetic regulation of planarian stem cells by the SET1/MLL family of histone methyltransferases. Epigenetics 8, 79-91.

Jiang, H., Shukla, A., Wang, X., Chen, W. Y., Bernstein, B. E., and Roeder, R. G. (2011). Role for Dpy-30 in ES cell-fate specification by regulation of H3K4 methylation within bivalent domains. Cell 144, 513-525.

Karatas, H., Townsend, E. C., Cao, F., Chen, Y., Bernard, D., Liu, L., Lei, M., Dou, Y., and Wang, S. (2013). High-affinity, small-molecule peptidomimetic inhibitors of MLL1/WDR5 protein-protein interaction. J Am Chem Soc 135, 669-682.

Kim D, Pertea G, Trapnell C, Pimentel H, Kelley R, Salzberg SL: TopHat2: accurate alignment of transcriptomes in the presence of insertions, deletions and gene fusions. Genome Biol 2013, 14(4):R36.

Koch, F., Scholze, M., Wittler, L., Schifferl, D., Sudheer, S., Grote, P., Timmermann, B., Macura, K., and Herrmann, B. G. (2017). Antagonistic Activities of Sox2 and Brachyury Control the Fate Choice of Neuro-Mesodermal Progenitors. Developmental cell 42, 514-526 e517.

Kokkinopoulos, I., Ishida, H., Saba, R., Coppen, S., Suzuki, K., and Yashiro, K. (2016). Cardiomyocyte differentiation from mouse embryonic stem cells using a simple and defined protocol. Developmental dynamics: an official publication of the American Association of Anatomists 245, 157-165.

Kouskoff, V., Lacaud, G., Schwantz, S., Fehling, H. J., and Keller, G. (2005). Sequential development of hematopoietic and cardiac mesoderm during embryonic stem cell differentiation. Proc Natl Acad Sci USA 102, 13170-13175.

Kovacs, G., Szabo, V., and Pirity, M. K. (2016). Absence of Rybp Compromises Neural Differentiation of Embryonic Stem Cells. Stem cells international 2016, 4034620.

Labelle-Dumais, C., Jacob-Wagner, M., Pare, J. F., Belanger, L., and Dufort, D. (2006). Nuclear receptor NR5A2 is required for proper primitive streak morphogenesis. Developmental dynamics: an official publication of the American Association of Anatomists 235, 3359-3369.

Langmead B, Salzberg SL: Fast gapped-read alignment with Bowtie 2. Nat Methods 2012, 9(4):357-359.

Li H, Handsaker B, Wysoker A, Fennell T, Ruan J, Homer N, Marth G, Abecasis G, Durbin R, Proc GPD: The Sequence Alignment/Map format and SAMtools. Bioinformatics 2009, 25(16):2078-2079.

Li, X., Li, L., Pandey, R., Byun, J. S., Gardner, K., Qin, Z., and Dou, Y. (2012). The histone acetyltransferase MOF is a key regulator of the embryonic stem cell core transcriptional network. Cell Stem Cell 11, 163-178.

Li, X., Yue, X., Pastor, W. A., Lin, L., Georges, R., Chavez, L., Evans, S. M., and Rao, A. (2016). Tet proteins influence the balance between neuroectodermal and mesodermal fate choice by inhibiting Wnt signaling. Proc Natl Acad Sci USA 113, E8267-E8276.

Mandai, M., Watanabe, A., Kurimoto, Y., Hirami, Y., Morinaga, C., Daimon, T., Fujihara, M., Akimaru, H., Sakai, N., Shibata, Y., et al. (2017). Autologous Induced Stem-Cell-Derived Retinal Cells for Macular Degeneration. N Engl J Med 376, 1038-1046.

Merkle, F. T., Ghosh, S., Kamitaki, N., Mitchell, J., Avior, Y., Mello, C., Kashin, S., Mekhoubad, S., Ric, D., Charlton, M., et al. (2017). Human pluripotent stem cells recurrently acquire and expand dominant negative P53 mutations. Nature 545, 229-233.

Nakano, T., Ando, S., Takata, N., Kawada, M., Muguruma, K., Sekiguchi, K., Saito, K., Yonemura, S., Eiraku, M., and Sasai, Y. (2012). Self-formation of optic cups and storable stratified neural retina from human ESCs. Cell Stem Cell 10, 771-785.

Odho, Z., Southall, S. M., and Wilson, J. R. (2010). Characterization of a novel WDR5-binding site that recruits RbBP5 through a conserved motif to enhance methylation of histone H3 lysine 4 by mixed lineage leukemia protein-1. J Biol Chem 285, 32967-32976.

Osakada, F., Ikeda, H., Sasai, Y., and Takahashi, M. (2009). Stepwise differentiation of pluripotent stem cells into retinal cells. Nat Protoc 4, 811-824.

Patel, A., Dharmarajan, V., and Cosgrove, M. S. (2008). Structure of WDR5 bound to mixed lineage leukemia protein-1 peptide. J Biol Chem 283, 32158-32161.

Perera, A., Eisen, D., Wagner, M., Laube, S. K., Kunzel, A. F., Koch, S., Steinbacher, J., Schulze, E., Splith, V., Mittermeier, N., et al. (2015). TET3 is recruited by REST for context-specific hydroxymethylation and induction of gene expression. Cell Rep 11, 283-294.

Pirity, M. K., Wang, W. L., Wolf, L. V., Tamm, E. R., Schreiber-Agus, N., and Cvekl, A. (2007). Rybp, a polycomb complex-associated protein, is required for mouse eye development. BMC developmental biology 7, 39.

Quadrato, G., Nguyen, T., Macosko, E. Z., Sherwood, J. L., Min Yang, S., Berger, D. R., Maria, N., Scholvin, J., Goldman, M., Kinney, J. P., et al. (2017). Cell diversity and network dynamics in photosensitive human brain organoids. Nature 545, 48-53.

Quinlan A R, Hall I M: BEDTools: a flexible suite of utilities for comparing genomic features. Bioinformatics 2010, 26(6):841-842.

Ramirez F, Dundar F, Diehl S, Gruning B A, Manke T: deepTools: a flexible platform for exploring deep-sequencing data. Nucleic Acids Res 2014, 42(W1):W187-W191.

Ramirez F, Ryan D P, Gruning B, Bhardwaj V, Kilpert F, Richter A S, Heyne S, Dundar F, Manke T: deepTools2: a next generation web server for deep-sequencing data analysis. Nucleic Acids Res 2016, 44(W1):W160-165.

Rao, R. C., Dedania, V. S., and Johnson, M. W. (2017). Stem cells for retinal disease: a perspective on the promise and perils. Am J Ophthalmol.

Rao, R. C., and Dou, Y. (2015). Hijacked in cancer: the KMT2 (MLL) family of methyltransferases. Nat Rev Cancer 15, 334-346.

Rojas, A., De Val, S., Heidt, A. B., Xu, S. M., Bristow, J., and Black, B. L. (2005). Gata4 expression in lateral mesoderm is downstream of BMP4 and is activated directly by Forkhead and GATA transcription factors through a distal enhancer element. Development 132, 3405-3417.

Rose, N. R., King, H. W., Blackledge, N. P., Fursova, N. A., Ember, K. J., Fischer, R., Kessler, B. M., and Klose, R. J. (2016). RYBP stimulates PRC1 to shape chromatin-based communication between Polycomb repressive complexes. eLife 5.

Schulz, Y., Freese, L., Manz, J., Zoll, B., Volter, C., Brockmann, K., Bogershausen, N., Becker, J., Wollnik, B., and Pauli, S. (2014). CHARGE and Kabuki syndromes: a phenotypic and molecular link. Human molecular genetics 23, 4396-4405.

Schwartz, S. D., Hubschman, J. P., Heilwell, G., Franco-Cardenas, V., Pan, C. K., Ostrick, R. M., Mickunas, E., Gay, R., Klimanskaya, I., and Lanza, R. (2012). Embryonic stem cell trials for macular degeneration: a preliminary report. Lancet 379, 713-720.

Schwartz, S. D., Regillo, C. D., Lam, B. L., Eliott, D., Rosenfeld, P. J., Gregori, N. Z., Hubschman, J. P., Davis, J. L., Heilwell, G., Spirn, M., et al. (2015). Human embryonic stem cell-derived retinal pigment epithelium in patients with age-related macular degeneration and Stargardt's macular dystrophy: follow-up of two open-label phase 1/2 studies. Lancet 385, 509-516.

Thomas, L. R., Foshage, A. M., Weissmiller, A. M., and Tansey, W. P. (2015a). The MYC-WDR5 Nexus and Cancer. Cancer Res 75, 4012-4015.

Thomas, L. R., Wang, Q., Grieb, B. C., Phan, J., Foshage, A. M., Sun, Q., Olejniczak, E. T., Clark, T., Dey, S., Lorey, S., et al. (2015b). Interaction with WDR5 promotes target gene recognition and tumorigenesis by MYC. Mol Cell 58, 440-452.

Thorvaldsdottir H, Robinson J T, Mesirov J P: Integrative Genomics Viewer (IGV): high-performance genomics data visualization and exploration. Brief Bioinform 2013, 14(2):178-192.

Wang, F., Han, J., Wang, L., Jing, Y., Zhu, Z., Hui, D., Wang, Z., Wang, Y., Dong, Y., and Tan, T. (2017). CCCTC-Binding Factor Transcriptionally Targets Wdr5 to Mediate Somatic Cell Reprogramming. Stem cells and development 26, 743-750.

Watanabe, K., Kamiya, D., Nishiyama, A., Katayama, T., Nozaki, S., Kawasaki, H., Watanabe, Y., Mizuseki, K., and Sasai, Y. (2005). Directed differentiation of telencephalic precursors from embryonic stem cells. Nature neuroscience 8, 288-296.

Wysocka, J., Swigut, T., Milne, T. A., Dou, Y., Zhang, X., Burlingame, A. L., Roeder, R. G., Brivanlou, A. H., and Allis, C. D. (2005). WDR5 associates with histone H3 methylated at K4 and is essential for H3 K4 methylation and vertebrate development. Cell 121, 859-872.

Yang, Y. W., Flynn, R. A., Chen, Y., Qu, K., Wan, B., Wang, K. C., Lei, M., and Chang, H. Y. (2014). Essential role of lncRNA binding for WDR5 maintenance of active chromatin and embryonic stem cell pluripotency. Elife 3, e02046.

Zaidi, S., Choi, M., Wakimoto, H., Ma, L., Jiang, J., Overton, J. D., Romano-Adesman, A., Bjornson, R. D., Breitbart, R. E., Brown, K. K., et al. (2013). De novo mutations in histone-modifying genes in congenital heart disease. Nature 498, 220-223.

Zhang Y, Liu T, Meyer C A, Eeckhoute J, Johnson D S, Bernstein B E, Nusbaum C, Myers R M, Brown M, Li W et al: Model-based analysis of ChIP-Seq (MACS). Genome Biol 2008, 9(9):R137.

Each of the references cited herein is hereby incorporated by reference in its entirety or in relevant part, as would be apparent from the context of the citation.

From the disclosure herein it will be appreciated that, although specific embodiments of the disclosure have been described herein for purposes of illustration, various modifications may be made without deviating from the spirit and scope of the disclosure.

What is claimed is:

1. A method for producing in culture a mesodermal lineage cell from an embryonic stem cell, wherein the embryonic stem cell comprises recombinant WD repeat domain 5 (WDR5) protein and wherein endogenous wdr5 gene expression in the embryonic stem cell is knocked out, the method comprising:
   a) transfecting the embryonic stem cell, wherein endogenous wdr5 gene expression is knocked out with a recombinant wdr5 gene and expressing recombinant WDR5 protein in the embryonic stem cell;
   b) disrupting interaction of recombinant WDR5 protein with retinoblastoma-binding protein 5 (RBBP5), MYC, or KAT8 Regulatory NSL Complex Subunit 2 (KANSL2) protein in the embryonic stem cell for a period of time greater than 24 hours and less than 60 hours by inhibiting expression of recombinant WDR5 protein by the embryonic stem cell by using an inducible gene expression system, and
   c) removing the disruption of the interaction of recombinant WDR5 protein with RBBP5, MYC, or KANSL2 in the embryonic stem cell to allow the mesodermal lineage cell to differentiate from the embryonic stem cell.

2. The method of claim 1, wherein inhibiting expression of recombinant WDR5 protein comprises:
   i) introducing a polynucleotide encoding a recombinant WDR5 protein under control of a transactivator protein into the embryonic stem cell; and
   ii) limiting the expression of the recombinant WDR5 protein in the embryonic stem cell by controlling the transactivator protein.

3. The method of claim 1, wherein the removing step comprises turning on the expression of the transactivator protein allowing expression of the recombinant WDR5 protein in the embryonic stem cell.

4. The method of claim 1, wherein the period of time starts when the embryonic stem cell is allowed to begin differentiation.

5. The method of claim 1, wherein the period of time is about 36 to about 48 hours.

* * * * *